United States Patent
Havranek et al.

(10) Patent No.: US 10,852,305 B2
(45) Date of Patent: *Dec. 1, 2020

(54) MOLECULES AND METHODS FOR ITERATIVE POLYPEPTIDE ANALYSIS AND PROCESSING

(71) Applicant: Washington University, St. Louis, MO (US)

(72) Inventors: James J. Havranek, Clayton, MO (US); Benjamin Borgo, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/907,813

(22) Filed: Jun. 22, 2020

(65) Prior Publication Data

US 2020/0319200 A1    Oct. 8, 2020

Related U.S. Application Data

(60) Continuation of application No. 15/255,433, filed on Sep. 2, 2016, which is a division of application No. 14/211,448, filed on Mar. 14, 2014, now Pat. No. 9,435,810.

(60) Provisional application No. 61/798,705, filed on Mar. 15, 2013.

(51) Int. Cl.
| | |
|---|---|
| *C12N 9/50* | (2006.01) |
| *C12Q 1/34* | (2006.01) |
| *C12N 9/64* | (2006.01) |
| *G01N 33/68* | (2006.01) |
| *C12N 9/52* | (2006.01) |
| *C12N 9/48* | (2006.01) |
| *C12N 9/00* | (2006.01) |

(52) U.S. Cl.
CPC ......... *G01N 33/6824* (2013.01); *C12N 9/485* (2013.01); *C12N 9/52* (2013.01); *C12N 9/641* (2013.01); *C12N 9/93* (2013.01); *C12Y 304/11018* (2013.01); *C12Y 601/0101* (2013.01); *C12Y 601/0102* (2013.01); *C12Y 601/01021* (2013.01)

(58) Field of Classification Search
CPC ....... C12N 9/50; C12N 9/641; G01N 33/6824
See application file for complete search history.

(56) References Cited

U.S. PATENT DOCUMENTS

| | | | |
|---|---|---|---|
| 7,611,834 B2 | 11/2009 | Chhabra et al. | |
| 8,340,951 B2 | 12/2012 | Baker et al. | |
| 2004/0005582 A1 | 1/2004 | Shipwash | |
| 2007/0218503 A1 | 9/2007 | Mitra | |

FOREIGN PATENT DOCUMENTS

WO    2010/065531 A1    6/2010

OTHER PUBLICATIONS

Notice to File Missing Parts of Nonprovisional Application, issued Apr. 1, 2014, in U.S. Appl. No. 14/211,448, 2 pages.
Preliminary Amendment A filed Apr. 30, 2014, in U.S. Appl. No. 14/211,448, 6 pages.
Notice to Comply, issued May 13, 2015, in U.S. Appl. No. 14/211,448, 3 pages.
Preliminary Amendment B filed Jun. 15, 2015, in U.S. Appl. No. 14/211,448, 7 pages.
Office Action (Restriction Requirement) dated Dec. 22, 2015, in U.S. Appl. No. 14/211,448, 7 pages.
Amendment C filed Feb. 22, 2016, in U.S. Appl. No. 14/211,448, 7 pages.
Examiner's Interview Summary dated Feb. 19, 2016, in U.S. Appl. No. 14/211,448, 3 pages.
Amendment D filed Apr. 26, 2016, in U.S. Appl. No. 14/211,448, 6 pages.
Notice of Allowance dated May 4, 2016, in U.S. Appl. No. 14/211,448, 17 pages.
Notice to File Missing Parts of Nonprovisional Application issued Sep. 13, 2016, in U.S. Appl. No. 15/255,433, 2 pages.
Preliminary Amendment A filed Nov. 14, 2016, in U.S. Appl. No. 15/255,433, 8 pages.
Office Action (Restriction Requirement) dated Jun. 26, 2019, in U.S. Appl. No. 15/255,433, 7 pages.
Preliminary Amendment B and Response to Restriction Requirement filed Dec. 23, 2019, in U.S. Appl. No. 15/255,433, 9 pages.
Non-Final Office Action dated Feb. 20, 2020, in U.S. Appl. No. 15/255,433, 16 pages.
Anderson, N.L., et al., The Human Plasma Proteome: History, Character, and Diagnostic Prospects, 2002, Mol Cell Proteomics, 1.11, pp. 845-867.
Amez, J.G., et al., "The first step of aminoacylation at the atomic level in histidyl-tRNA synthetase," 1997, PNAS USA., 94:7144-7149.
Ashworth, J., et al., Computational Redesign of Endonuclease DNA Binding and Cleavage Specificity, 2006, Nature, 441:656-659.
Ashworth, J., et al. "Computational Reprogramming of Homing Endonuclease Specificity at Multiple Adjacent Base Pairs," 2010, Nucleic Acids Res., 38/16:5601-5608.

(Continued)

*Primary Examiner* — Maryam Monshipouri
(74) *Attorney, Agent, or Firm* — Stinson LLP

(57) ABSTRACT

Reagents and methods for the digital analysis of proteins or peptides are provided. Specifically provided herein are proteins for identifying the N-terminal amino acid or N-terminal phosphorylated amino acid of a polypeptide. Also, an enzyme for use in the cleavage step of the Edman degradation reaction and a method for using this enzyme are described.

23 Claims, 8 Drawing Sheets

Specification includes a Sequence Listing.

(56) References Cited

OTHER PUBLICATIONS

Augustine, J., et al., "Design of an Active Fragment of a Class II Aminoacyl-tRNA Synthetase and Its Significance for Synthetase Evolution," 1997, Biochemistry, 36:3473-3482.
Barrett, G.C., et al., "Edman Stepwise Degradation of Polypeptides: A New Strategy Employing Mild Basic Cleavage Conditions," 1985, Tetrahedron Lett., 26:4375-4378.
Berman, H., et al., "The worldwide Protein Data Bank (wwPDB): ensuring a single, uniform archive of PDB data," 2007, Nucleic Acids Res., 35:D301-D303.
Carter, P., et al., "Engineering enzyme specificity by substrate-assisted catalysis," 1987, Science, 237:394-399.
Celej, M.S., et al., "Protein stability induced by ligand binding correlates with changes in protein flexibility," 2003, Protein Sci., 12:1496-1506.
Chiravuri M, et al., "Vesicular Localization and Characterization of a Novel Post-Proline-Cleaving Aminodipeptidase, Quiescent Cell Proline Dipeptidase," 2000, J Immunol., 165:5695-5702.
Choe, Y., et al., "Development of α-keto-based inhibitors of cruzain, a cysteine protease implicated in Chagas disease," 2005, Bioorg Med Chem., 13:2141-2156.
Dantas, G., et al., "High-resolution Structural and Thermodynamic Analysis of Extreme Stabilization of Human Procarboxypeptidase by Computational Protein Design," 2007, J Mol Biol., 366:1209-1221.
Dunbrack, R.L. et al., "Backbone-dependent Rotamer Library for Proteins Application to Side-chain Prediction," 1993, J Mol Biol., 230:543-574.
Duncan, M.W., et al., "The pros and cons of peptide-centric proteomics," 2010, Nature Biotechnology, 28:659-664.
Edman P., "Method for Determination of the Amino Acid Sequence in Peptides," 1950, Acta Chem Scand., 4:283-293.
Emmert-Buck, M.R., et al., "Laser Capture Microdissection," 1996, Science, 274:998-1001.
Finn, R.D., et al., "The Pfam protein families database," 2008, Nucleic Acids Res., 36, pp. D281-D288.
Fukunaga, R., et al., "Structural insights into the first step of RNA-dependent cysteine biosynthesis in archaea," 2007, Nat Struct Mol Biol., 14:272-279.
Gillette, M.A., et al. "Place of Pattern in Proteomic Biomarker Discovery," 2005, J Proteome Res., 4: 1143-1154.
Grimsrud, P.A., et al., "Phosphoproteomics for the Masses," 2010, ACS Chem Biol., 5:105-119.
Havranek, J.J., et al., "Automated design of specificity in molecular recognition," 2003, Nat Struct Biol., 10:45-52.
Havranek, J.J., et al., "Motif-directed flexible backbone design of functional interactions," 2009, Protein Sci., 18: 1293-1305.
Holm, L., et al., "Dali server: conservation mapping in 3D," 2010, Nucleic Acids Res., 38:W545-W549.
Ingolia, N.T., et al., "Genome-wide analysis in vivo of translation with nucleotide resolution using ribosome profiling," 2009, Science, 324:218-223.
Jiang, L., et al., "De novo computational design of retro-aldol enzymes," 2008, Science, 319:1387-1391.
Kavran, J.M., et al., "Structure of pyrrolysyl-tRNA synthetase, an archaeal enzyme for genetic code innovation," 2007, PNAS USA,, 104:11268-11273.
Kuhlman, B., et al., "Native protein sequences are close to optimal for their structures," 2000, PNAS USA, 97:10383-10388.
Laursen, R.A., "Solid-Phase Edman Degradation an Automatic Peptide Sequencer," 1971, Eur J Biochem, 20:89-102.
Liu, C.C., et al., "Recombinant expression of selectively sulfated proteins in *Escherichia coli*," 2006, Nat Biotechnol., 24:1436-1440.
McGrath, M.E., "The lysosomal cysteine proteases," 1999, Annu Rev Biophys Biomol Struct., 28:181-204.
McLachlin, D.T., et al., "Analysis of phosphorylated proteins and peptides by mass sepctrometry," 2001, Curr Op Chem Biol, 5:591-602.
O'Brien, P.J., et al., "Catalytic promiscuity and the evolution of new enzymatic activities," 1999, Chem Biol., 6:R91-R105.
Rothlisberger, D., et al., "Kemp elimination catalysts by computational enzyme design," 2008, Nature, 453:190-195.
Schmidt, M.W., et al., "General atomic and molecular electronic structure system," 1993, J Comput Chem., 14:1347-1363.
Schmitt, E., et al., "Switching from an induced-fit to a lock-and-key mechanism in an aminoacyl-tRNA synthetase with modified specificity," 2009, J Mol Biol., 394:843-851.
Steen, H., et al., "The ABC's (and XYZ's) of Peptide Sequencing," 2004, Mol Cell Biol, 5:699-711.
Sterner, R., et al., "Computational Design of Enzymes," 2008, Chemistry & Biology, 15:421-423.
Studier, F.W., "Protein production by auto-induction in high-density shaking cultures," 2005, Protein Expr Purif., 41:207-234.
Tessler, L.A., et al., "Protein Quantification in Complex Mixtures by Solid Phase Single-Molecule Counting," 2009, Anal Chem. 81:7141-7148.
Tessler, L.A., et al., "Nanogel surface coatings for improved single-molecule imaging substrates," 2011, J R Soc Interface, 8:1400-1408.
Tessler, L., "Digital Protein Analysis: Technologies for Protein Diagnostics and Proteomics through Single-Molecule Detection," Jan. 1, 2011, Electronic Theses and Dissertations, Paper 346, 147 pages.
Turner, J.M., et al., "Structural characterization of a p-acetylphenylalanyl aminoacyl-tRNA synthetase," 2005, J Am Chem Soc., 127:14976-14977.
Williams, N.A., et al., "Protein Sequencing in the Proteomic Age," 2001, Poster #263, 15th Symposium of the Protein Society, Philadelphia, PA, 17 pages.
Wolf, Y.I., et al., "Evolution of aminoacyl-tRNA synthetases-analysis of unique domain architectures and phylogenetic trees reveals a complex history of horizontal gene transfer events," 1999, Genome Res., 9:689-710.
Xie, J., et al., "A genetically encoded metabolically stable analogue of phosphotyrosine in *Escherichia coli*," ACS Chem Biol., 2:474-478.
Yamaguchi, M., et al., "High-Throughput Method for Terminal Sequencing of Proteins by MALDI Mass Spectrometry," 2005, Anal Chem, 77:645-651.
Handbook, Fluorescence Imaging Principles and Methods, Amersam Biosciences, 63-0035-28 Rev.AB, Oct. 2002, 166 pages.
A Practical Guide to Protein and Peptide Purification and Microsequencing, "Chapter 4: Protein and Peptide Purification for Microsequencing," 1993, P. Matsudaira, Ed., Academic Press, London, England 7 pages.
Protein Sequencing, Yale School of Medicine, W.M. Keck Foundation, Website http:\\medicine.yale.edu, downloaded Mar. 4, 2014, 1 page.

N-terminal amino acids

MOLECULES AND METHODS FOR ITERATIVE POLYPEPTIDE ANALYSIS AND PROCESSING

REFERENCE TO RELATED APPLICATIONS

This application is a continuation of U.S. patent application Ser. No. 15/255,433, filed Sep. 2, 2016, which is a division of U.S. patent application Ser. No. 14/211,448, filed Mar. 14, 2014, now U.S. Pat. No. 9,435,810, issued Sep. 5, 2016, which claims the benefit of U.S. Provisional Application No. 61/798,705, filed Mar. 15, 2013, the entire disclosures of which are incorporated herein by reference.

GOVERNMENT LICENSE RIGHTS

This invention was made with Government support under grant R01 GM101602 awarded by the National Institutes of Health. The Government has certain rights in the invention.

FIELD OF THE INVENTION

The present invention generally relates to reagents and methods for the digital analysis of proteins or peptides. Specifically provided herein are proteins for identifying the N-terminal amino acid or N-terminal phosphorylated amino acid of a polypeptide. Another aspect of the invention is an enzyme for use in the cleavage step of the Edman degradation reaction and a method for using this enzyme.

BACKGROUND OF THE INVENTION

Proteins carry out the majority of signaling, metabolic, and regulatory tasks necessary for life. As a result, a quantitative description of the proteomic state of cells, tissues, and fluids is crucial for assessing the functionally relevant differences between diseased and unaffected tissues, between cells of different lineages or developmental states, and between cells executing different regulatory programs. Although powerful high-throughput techniques are available for determining the RNA content of a biological sample, the correlation between mRNA and protein levels is low (1).

The preferred method for proteomic characterization is currently mass spectrometry. Despite its many successes, mass spectrometry possesses limitations. One limitation is quantification. Because different proteins ionize with different efficiencies, it is difficult to compare relative amounts between two samples without isotopic labeling (2). In 'shotgun' strategies for analyzing complex samples, the uncertainties of peptide assignment further complicate quantification, especially for low abundance proteins (3). A second limitation of mass spectrometry is its dynamic range. For unbiased samples that have not undergone prefractionation or affinity purification, the dynamic range in analyte concentration is roughly $10^2$-$10^3$, depending upon the instrument (4). This is problematic for complex samples such as blood, where two proteins whose levels are measured in clinical laboratories (albumin and interleukin-6) can differ in abundance by $10^{10}$ (5). Another limitation is the analysis of phosphopeptides, due to the loss of phosphate in some ionization modes. The power of proteomic approaches would increase dramatically with the introduction of a more quantitative high-throughput assay possessing greater dynamic range.

One promising technology for the analysis of proteins in a sensitive and quantitative manner was developed by Mitra et al (7). This technology, referred to as Digital Analysis of Proteins by End Sequencing or DAPES, features a method for single molecule protein analysis. To perform DAPES, a large number (ca. $10^9$) of protein molecules are denatured and cleaved into peptides. These peptides are immobilized on a nanogel surface applied to the surface of a microscope slide and their amino acid sequences are determined in parallel using a method related to Edman degradation. Phenyl isothiocyanate (PITC) is added to the slide and reacts with the N-terminal amino acid of each peptide to form a stable phenylthiourea derivative. Next, the identity of the N-terminal amino acid derivative is determined by performing, for example, 20 rounds of antibody binding with antibodies specific for each PITC-derivatized N-terminal amino acid, detection, and stripping. The N-terminal amino acid is removed by raising the temperature or lowering pH, and the cycle is repeated to sequence 12-20 amino acids from each peptide on the slide. The absolute concentration of every protein in the original sample can then be calculated based on the number of different peptide sequences observed.

The phenyl isothiocyanate chemistry used in DAPES is the same used in Edman degradation and is efficient and robust (>99% efficiency). However, the cleavage of single amino acids requires strong anhydrous acid or alternatively, an aqueous buffer at elevated temperatures. Cycling between either of these harsh conditions is undesirable for multiple rounds of analysis on sensitive substrates used for single molecule protein detection (SMD). Thus, there is a need in the art for improved reagents and methods for the parallel analysis of peptides in single molecule protein detection (SMD) format.

SUMMARY OF THE INVENTION

One aspect of the invention is an improved method for single molecule sequencing of proteins or peptides. Generally, the method for sequencing a polypeptide, the method comprises (a) contacting the polypeptide with one or more fluorescently labeled N-terminal amino acid binding proteins (NAABs); (b) detecting fluorescence of a NAAB bound to an N-terminal amino acid of the polypeptide; (c) identifying the N-terminal amino acid of the polypeptide based on the fluorescence detected; (d) removing the NAAB from the polypeptide; (e) optionally repeating steps (a) through (d); (f) cleaving the N-terminal amino acid of the polypeptide via Edman degradation; and (g) repeating steps (a) through (f) one or more times.

The present invention also generally relates to reagents for the digital analysis of proteins or peptides. Specifically provided herein are proteins for identifying the N-terminal amino acid or N-terminal phosphorylated amino acid of a polypeptide.

Another aspect of the invention relates to an enzyme for use in the cleavage step of the Edman degradation reaction and a method for using this enzyme. Generally, the enzymatic Edman degradation method comprises reacting the N-terminal amino acid of the polypeptide with phenyl isothiocyanate (PITC) to form a PITC-derivatized N-terminal amino acid and cleaving the PITC-derivatized N-terminal amino acid using an Edman degradation enzyme.

Other objects and features will be in part apparent and in part pointed out hereinafter.

DESCRIPTION OF THE INVENTION

Figure 1:
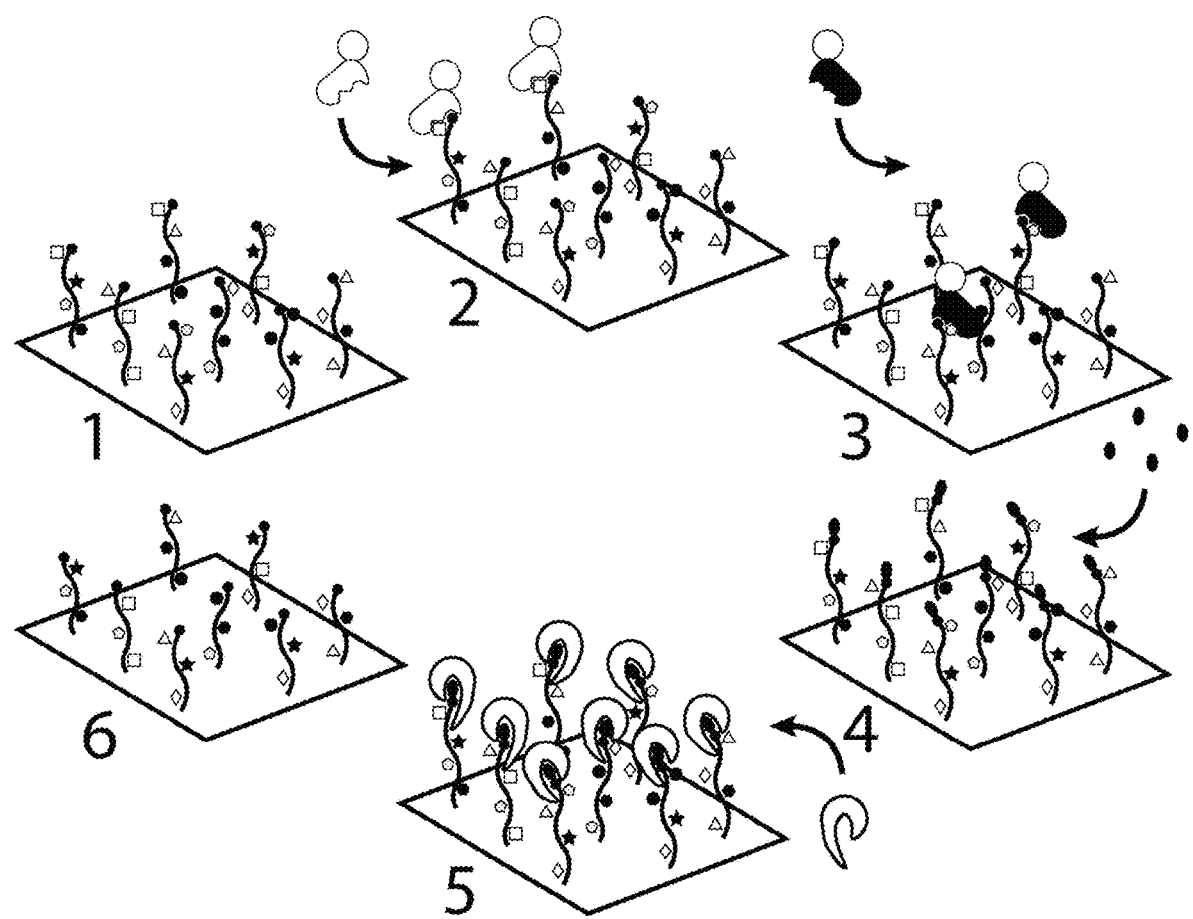
FIG. 1 depicts the Digital Analysis of Proteins by End Sequencing Protocol (DAPES) utilizing N-terminal amino acid binding proteins in the identification step and a synthetic enzyme in the cleavage step.

In one aspect, the present invention is directed to a method and reagents for sequencing a polypeptide. In particular, the present invention provides methods and reagents for the single-molecule, high-throughput sequencing of polypeptides. Recent advances in single-molecule protein detection (SMD) allow for the parallel analysis of large numbers of individual proteins utilizing digital protocols. In accordance with the present invention, reagents capable of specifically binding to N-terminal amino acids for an identification step are provided.

The present invention also includes methods and reagents for identification phosphorylated N-terminal amino acids. Quantitatively interrogating peptide sequences in neutral aqueous environments allows for the possibility of proteomic analyses complementary to those afforded by mass spectrometry. The N-terminal amino acids specific for phosphorylated forms of amino acids allow for quantitative comparison of proteomic inventories and signal transduction cascades in different samples.

In another aspect, the present invention is directed to a method and reagents for enzymatic Edman degradation (i.e., for enzymatically cleaving the N-terminal amino group of a polypeptide). In accordance with this aspect, a synthetic enzyme is provided that catalyzes the cleavage step of the Edman degradation reaction in an aqueous buffer and at neutral pH, thereby providing an alternative to the harsh chemical conditions typically employed in Edman degradation.

Yet another aspect of the present invention is directed to an integrated high-throughput method for sequencing of polypeptides that includes use of reagents capable of specifically binding to N-terminal amino acids for an identification step and use of an enzymatic Edman degradation to remove N-terminal amino acids.

I. N-terminal Amino Acids Binders (NAABs)

In accordance with the present invention, reagents capable of specifically binding to N-terminal amino acids are provided. In various aspects of the invention, the N-terminal amino acid binders (NAABs) each selectively bind to a particular amino acid, for example one of the twenty standard naturally occurring amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr).

The NAABs of the present invention can be made by modifying various naturally occurring proteins to introduce one or more mutations in the amino acid sequence to produce engineered proteins that bind to particular N-terminal amino acids. For example, aminopeptidases or tRNA synthetases can be modified to create NAABs that selectively bind to particular N-terminal amino acids.

A. eLAP

For example, a NAAB that binds specifically to N-terminal leucine residues has been developed by introducing mutations into *E. coli* methionine aminopeptidase (eMAP). This NAAB (eLAP) has 19 amino acid substitutions as compared to wild-type eMAP. In particular, eLAP has substitutions at the amino acid positions corresponding to positions 42, 46, 56-60, 62, 63, 65-70, 81, 101, 177, and 221 of wild-type eMAP. In eLAP, the aspartate at position 42 of eMAP is replaced with a glutamate, the asparagine at position 46 of eMAP is replaced with a tryptophan, the valine at position 56 of eMAP is replaced with a threonine, the serine at position 57 of eMAP is replaced with an aspartate, the alanine at position 58 of eMAP is replaced with a serine, the cysteine at position 59 of eMAP is replaced with a leucine, the leucine at position 60 of eMAP is replaced with a threonine, the tyrosine at position 62 of eMAP is replaced with a histidine, the histidine at position 63 of eMAP is replaced with an asparagine, the tyrosine at position 65 of eMAP is replaced with a isoleucine, the proline at position 66 of eMAP is replaced with an aspartate, the lysine at position 67 of eMAP is replaced with a glycine, the serine at position 68 of eMAP is replaced with a histidine, the valine at position 69 of eMAP is replaced with a glycine, the cysteine at position 70 of eMAP is replaced with a serine, the isoleucine at position 81 of eMAP is replaced with a valine, the isoleucine at position 101 of eMAP is replaced with an arginine, the phenylalanine at position 177 of eMAP is replaced with a histidine, and the tryptophan at position 221 of eMAP is replaced with a serine. Alternative substitutions could be made at selected positions. For example, valine at 56 could be replaced instead by serine, leucine at 60 could be replaced instead by serine, tyrosine at 65 could be replaced instead by valine, cysteine at 70 could be replaced instead by threonine, and tryptophan at 221 could be replaced instead by threonine.

Accordingly, one reagent in accordance with the present invention comprises an isolated, synthetic, or recombinant NAAB comprising an amino acid sequence having a glutamate residue at a position corresponding to position 42 of wild-type *E. coli* methionine aminopeptidase (eMAP) (SEQ ID NO: 1), a tryptophan residue at a position corresponding to position 46 of wild-type eMAP, a threonine or serine residue at a position corresponding to position 56 of wild-type eMAP, an aspartate residue at a position corresponding to position 57 of wild-type eMAP, a serine residue at a position corresponding to position 58 of wild-type eMAP, a leucine residue at a position corresponding to position 59 of wild-type eMAP, a threonine or serine residue at a position corresponding to position 60 of wild-type eMAP, a histidine residue at a position corresponding to position 62 of wild-type eMAP, an asparagine residue at a position corresponding to position 63 of wild-type eMAP, a isoleucine or valine residue at a position corresponding to position 65 of wild-type eMAP, an aspartate residue at a position corresponding to position 66 of wild-type eMAP, a glycine residue at a position corresponding to position 67 of wild-type eMAP, a histidine residue at a position corresponding to position 68 of wild-type eMAP, a glycine residue at a position corresponding to position 69 of wild-type eMAP, a serine or threonine residue at a position corresponding to position 70 of wild-type eMAP, a valine residue at a position corresponding to position 81 of wild-type eMAP, an arginine residue at a position corresponding to position 101 of wild-type eMAP, a histidine residue at a position corresponding to position 177 of wild-type eMAP, and a serine or threonine residue at a position corresponding to position 221 of wild-type eMAP.

The remaining amino acid sequence of the NAAB comprises a sequence similar to that of wild-type eMAP, but which may contain additional amino acid mutations (including deletions, insertions, and/or substitutions), so long as such mutations do not significantly impair the ability of the NAAB to selectively bind to N-terminal leucine residues. For example, the remaining amino acid sequence can comprise an amino acid sequence having at least about 80% sequence identity to the amino acid sequence of wild-type eMAP (SEQ ID NO: 1), or at least 85%, at least 90%, at least 93%, at least 95%, at least 96%, at least 97%, at least 98%, at least 99%, or 100% sequence identity to the amino acid sequence of SEQ ID NO: 1.

In some aspects of the present invention, the NAAB comprises the amino acid sequence of SEQ ID NO: 2. For example, the NAAB can consist of the amino acid sequence of SEQ ID NO: 2.

The NAAB preferably selectively binds to N-terminal leucine residues with at least about a 1.5:1 ratio of specific to non-specific binding, more preferably about a 2:1 ratio of specific to non-specific binding. Non-specific binding refers to background binding, and is the amount of signal that is produced when the amino acid target of the NAAB is not present at the N-terminus of an immobilized peptide.

B. tRNA Synthetase-Based NAABs

1. N-Terminal Methionine Binding Protein

NAABs can also be made by introducing mutations into class I and class II tRNA synthetases (RSs). NAABs for use in the polypeptide sequencing processes described herein should possess high affinity and specificity for amino acids at the N-terminus of peptides. Because tRNA synthetases have intrinsic specificity for free amino acids, they are useful scaffolds for developing NAABs for use in protein sequencing. The inherent specificity of these scaffold proteins is retained, while broadening the binding capabilities of these proteins from free monomers to peptides, and removing unnecessary domains or functions. The Protein Data Bank contains multiple crystal structures for RSs specific for all twenty canonical amino acids. Moreover, unlike other classes of amino acid binding molecules, such as riboswitches, RSs do not envelop the entire amino acid, as the C-terminus must be available for adenylation. The binding pocket in these molecules can be modified to permit the entry of peptides presenting the specifically bound amino acid. This results in a complete set of engineered RS fragments that can bind to their cognate amino acids at the N-termini of peptides.

The class IRS proteins form a distinct structural family that is identified by sequence homology and has been extensively characterized both biochemically and biophysically. RS proteins possess a modular architecture, and the domains conferring specificity for a particular amino acid are readily identified (18). Several types of mutations to improve the performance of the amino acid binding domain of an RS as a NAAB can be introduced. First, one or more mutations can be introduced into the binding domain to lock the domain into the bound conformation, eliminating the energetic cost of any induced conformational change (16). Second, one or more mutations can be introduced to widen the binding pocket for the amino acid, making room for entry of a peptide. This approach can be used for each of the RS proteins.

For example, mutations can be introduced into methionyl-tRNA synthetase (MetRS) from *E. coli* to create a NAAB that binds specifically to N-terminal methionine residues. This NAAB comprises a truncated version of wild-type *E. coli* MetRS (residues 4-547; SEQ ID NO: 3) having four substitution mutations as compared to the wild-type sequence (SEQ ID NO: 5). The sequence of this N-terminal methionine-specific NAAB is provided by SEQ ID NO: 4. In particular, in the methionine-specific NAAB, the leucine at position 13 of wild-type *E. coli* MetRS is replaced with a serine (L13S), the phenylalanine at position 260 is replaced with a leucine (Y260L), the aspartic acid at position 296 is replaced with a glycine (D296G), and the histidine at position 301 is replaced with a leucine (H301L).

Accordingly, one reagent in accordance with the present invention comprises an isolated, synthetic, or recombinant NAAB comprising an amino acid sequence having a serine residue at a position corresponding to position 13 of wild-type *E. coli* methionyl-tRNA synthetase (MetRS); a leucine residue at a position corresponding to position 260 of wild-type *E. coli* MetRS; a glycine residue at a position corresponding to position 296 of wild-type *E. coli* MetRS; and a leucine residue at a position corresponding to position 301 of wild-type *E. coli* MetRS.

The remaining amino acid sequence of the NAAB comprises a sequence similar to that of amino acids 4-547 of wild-type MetRS, but may contain additional amino acid mutations (including deletions, insertions, and/or substitutions), so long as such mutations do not significantly impair the ability of the NAAB to selectively bind to N-terminal methionine residues. For example, the remaining amino acid sequence can comprise an amino acid sequence having at least about 80% sequence identity to the amino acid sequence of SEQ ID NO: 3, or at least 85%, at least 90%, at least 93%, at least 95%, at least 96%, at least 97%, at least 98%, at least 99%, or 100% sequence identity to the amino acid sequence of SEQ ID NO: 3.

In certain aspects of the invention, the NAAB comprises the amino acid sequence of SEQ ID NO: 4. For example, the NAAB can consist of the amino acid sequence of SEQ ID NO: 4.

The NAAB preferably selectively binds to N-terminal methionine residues with at least about a 2:1 ratio of specific to non-specific binding, more preferably at least about a 7:1 ratio, at least about a 10:1 ratio, or about a 13:1 ratio of specific to non-specific binding.

2. N-Terminal Phenylalanine Binding Protein

The starting point for the phenylalanine NAAB (Phe NAAB) was the phenylalanine-tRNA synthetase (PheRS) from *Thermus thermophilus*, for which a crystal structure is available. Normally the operational unit is a tetramer with two copies each of two separate proteins. Only one of the proteins has the amino acid binding specificity, so a model was made of one copy of the protein in isolation. The N-terminus of the protein was truncated, which exposed a significant amount of surface area that was previously buried in contacts with other proteins. This surface was hydrophobic, and mutations were made the surface to make the protein stabile and soluble as a monomer. Tighter binding of the mutant to peptides was observed when compared to the wild-type protein.

For example, mutations can be introduced into PheRS from *Thermus thermophilus* to create a NAAB that binds specifically to N-terminal phenylalanine residues. This NAAB comprises a truncated version of wild-type *Thermus thermophilus* PheRS (residues 86-350; SEQ ID NO: 6) having 22 substitution mutations as compared to the wild-type sequence. The sequence of this N-terminal phenylalanine-specific NAAB is provided by SEQ ID NO: 7. In particular, PheNAAB has substitutions at the amino acid positions corresponding to positions 100, 142, 143, 152-154, 165, 205, 212, 228-232, 234, 257, 287, 289, 303, 336, 338, 340 of wild-type PheRS. In the NAAB, the leucine at position 100 of PheRS is replaced with an aspartate, the histidine at position 142 of PheRS is replaced with an asparagine, the histidine at position 143 of PheRS is replaced with a glycine, the phenylalanine at position 152 of PheRS is replaced with a valine, the tryptophan at position 153 of PheRS is replaced with a glycine, the leucine at position 154 of PheRS is replaced with a lysine, the leucine at position 165 of PheRS is replaced with an aspartate, the phenylalanine at position 205 of PheRS is replaced with an alanine, the histidine at position 212 of PheRS is replaced with an alanine, the isoleucine at position 228 of PheRS is replaced with a valine, the alanine at position 229 of PheRS is replaced with an asparagine, the methionine at position 230 of PheRS is replaced with a glutamate, the alanine at position 231 of PheRS is replaced with a glycine, the histidine at position 232 of PheRS is replaced with an aspartate, the lysine at position 234 of PheRS is replaced with a tyrosine, the tyrosine at position 257 of PheRS is replaced with a threonine, the histidine at position 287 of PheRS is replaced with a glycine, the lysine at position 289 of PheRS is replaced with an asparagine, the leucine at position 303 of PheRS is replaced with an aspartate, the phenylalanine at position 336 of PheRS is replaced with an alanine, the glycine at position 338 of PheRS is replaced with a threonine, and the leucine at position 340 of PheRS is replaced with a glycine.

Accordingly, one reagent in accordance with the present invention comprises an isolated, synthetic, or recombinant NAAB comprising an amino acid sequence having a an aspartate residue at a position corresponding to position 100 of wild-type PheRS from *Thermus thermophilus* (SEQ ID NO: 8), an asparagine residue at a position corresponding to position 142 of wild-type PheRS, a glycine residue at a position corresponding to position 143 of wild-type PheRS, a valine residue at a position corresponding to position 152 of wild-type PheRS, a glycine residue at a position corresponding to position 153 of wild-type PheRS, a lysine residue at a position corresponding to position 154 of wild-type PheRS, an aspartate residue at a position corresponding to position 165 of wild-type PheRS, an alanine residue at a position corresponding to position 205 of wild-type PheRS, an alanine residue at a position corresponding to position 212 of wild-type PheRS, a valine residue at a position corresponding to position 228 of wild-type PheRS, an asparagine residue at a position corresponding to position 229 of wild-type PheRS, a glutamate residue at a position corresponding to position 230 of wild-type PheRS, a glycine residue at a position corresponding to position 231 of wild-type PheRS, an aspartate residue at a position corresponding to position 232 of wild-type PheRS, a tyrosine residue at a position corresponding to position 234 of wild-type PheRS, a threonine residue at a position corresponding to position 257 of wild-type PheRS, a glycine residue at a position corresponding to position 287 of wild-type PheRS, an asparagine residue at a position corresponding to position 289 of wild-type PheRS, an aspartate residue at a position corresponding to position 303 of wild-type PheRS, an alanine residue at a position corresponding to position 336 of wild-type PheRS, a threonine residue at a position corresponding to position 338 of wild-type PheRS, and a glycine residue at a position corresponding to position 340 of wild-type PheRS.

The remaining amino acid sequence of the NAAB comprises a sequence similar to that of wild-type PheRS, but which may contain additional amino acid mutations (including deletions, insertions, and/or substitutions), so long as such mutations do not significantly impair the ability of the NAAB to selectively bind to N-terminal phenylalanine residues. For example, the remaining amino acid sequence can comprise an amino acid sequence having at least about 80% sequence identity to the amino acid sequence of truncated wild-type PheRS (SEQ ID NO: 6), or at least 85%, at least 90%, at least 93%, at least 95%, at least 96%, at least 97%, at least 98%, at least 99%, or 100% sequence identity to the amino acid sequence of SEQ ID NO:6.

In some aspects of the present invention, the NAAB comprises the amino acid sequence of SEQ ID NO: 7. For example, the NAAB can consist of the amino acid sequence of SEQ ID NO: 7.

The NAAB preferably selectively binds to N-terminal phenylalanine residues with at least about a 1.5:1 ratio of specific to non-specific binding, more preferably about a 2:1 ratio of specific to non-specific binding.

3. N-Terminal Histidine Binding Protein

The starting point for the histidine NAAB (His NAAB) was the histidine-tRNA synthetase (HisRS) from *E. Coli*, for which a crystal structure is available. The fragment of wild-type HisRS from 1-320 was shown to be monomeric by others. After inspecting the crystal structure, further residues were truncated from both ends. The initial fragment tested has from Lysine3 to Alanine180. Protein design was conducted to replace a long loop near the binding site with a shorter loop that would create a more open pocket and result in tighter binding to N-terminal histidine residues. This involved the removal of 7 residues (from Arginine113 to Lysine119) and two mutations wherein the arginine at position 121 of HisRS is replaced with an asparagine, and the tyrosine at position 122 of HisRS is replaced with an alanine. Thus, thus this NAAB comprises a truncated version of wild-type *E. coli* HisRS (residues 3-180; SEQ ID NO: 10) having two substitution mutations as compared to the wild-type sequence. The sequence of this N-terminal histidine-specific NAAB is provided by SEQ ID NO: 9.

Accordingly, one reagent in accordance with the present invention comprises an isolated, synthetic, or recombinant NAAB comprising an amino acid sequence having an asparagine residue at a position corresponding to position 121 of wild-type HisRS from *E. coli* (SEQ ID NO: 9) and an alanine residue at a position corresponding to position 122 of wild-type HisRS.

The remaining amino acid sequence of the NAAB comprises a sequence similar to that of wild-type HisRS, but which may contain additional amino acid mutations (including deletions, insertions, and/or substitutions), so long as such mutations do not significantly impair the ability of the NAAB to selectively bind to N-terminal histidine residues. For example, the remaining amino acid sequence can comprise an amino acid sequence having at least about 80% sequence identity to the amino acid sequence of wild-type HisRS (SEQ ID NO: 9), or at least 85%, at least 90%, at least 93%, at least 95%, at least 96%, at least 97%, at least 98%, at least 99%, or 100% sequence identity to the amino acid sequence of SEQ ID NO: 9.

In some aspects of the present invention, the NAAB comprises the amino acid sequence of SEQ ID NO: 10. For example, the NAAB can consist of the amino acid sequence of SEQ ID NO: 10.

The NAAB preferably selectively binds to N-terminal histidine residues with at least about a 1.5:1 ratio of specific to non-specific binding, more preferably about a 2:1 ratio of specific to non-specific binding.

4. Other NAABs

Full-length or truncated fragments from wild-type synthetases from *E. coli* may be used as NAABs for the remaining amino acids. See Table A for the sequences of each of the NAABs. Accordingly, in some aspects of the present invention, the NAAB comprises an amino acid sequence selected from the group consisting of SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; and SEQ ID NO: 28. In various embodiments, a set of NAABs comprises at least 2, 3, 4, 5, 6, 7, 8, 9, 10, 11, 12, 13, 14, 15 or more of the amino acid sequences of SEQ ID NO: 2; SEQ ID NO: 4; SEQ ID NO: 7; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; and SEQ ID NO: 28. For example, a set of NAABs comprises of the amino acid sequences of SEQ ID NO: 2; SEQ ID NO: 4; SEQ ID NO: 7; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; and SEQ ID NO: 28.

C. NAABs for PITC-Derivatized Lysine

The phenyl isothiocyanate (PITC) reagent used to activate peptide N-termini for stepwise degradation also reacts with the $N_\varepsilon$ atom in the lysine side chain. As a result, domains derived from lysine RNA synthetase (LysRS) proteins cannot be used for specific recognition of modified lysine. A NAAB that is specific for PITC-derivatized lysine is therefore required. The class II RS for pyrrolysine (PylRS) served as a starting point for development. Pyrrolysine is a lysine derivative that possesses a pyrrole ring attached to the $N_\varepsilon$ atom by an amide linkage (Structure A). Crystal structures have been determined for PylRS bound to several ligands (23), one of which is one bond longer than pyrrolysine (Structure B), and possesses steric similarity to a model of PITC-derivatized lysine (Structure C).

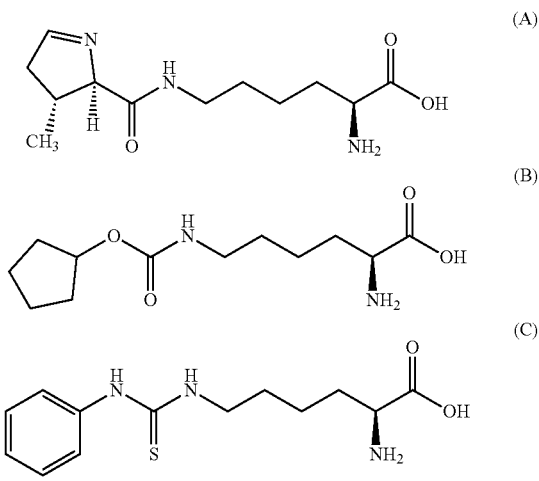

Genomic DNA for the archaea *Methanosarcina mazei*, the source organism for the crystal structure, will be obtained from the American Type Culture Collection (ATCC). The gene will be cloned and expressed. The relevant substrate for assessing compatibility with the DAPES strategy is a peptide with an N-terminal lysine that has been modified with PITC on its side chain, but not its amino terminus. It is expected that the side chain will be derivatized during previous cycles, but that the N-terminus will be regenerated by the cleavage step of the preceding cycle. A peptide with the sequence DKGMMGSSC will be obtained. The peptide will be derivatized with PITC, modifying both the N-terminus and the side chain of the lysine at the second position. The modified aspartate residue will be with the designed enzyme, which has excellent activity against PITC-modified aspartate. The resulting peptide, with an N-terminal lysine modified only on its side chain, will be purified from the reaction mixture by HPLC. The peptide will then be immobilized on the nanogel surface via its C-terminal cysteine. The liberated PyRS domain will be fluorescently labeled with Cy5 and assayed for binding to the immobilized peptide.

In the event that the engineered domain exhibits poor binding, a structural model of the NAAB in complex with pyrrolysine will be constructed using the crystal structure as a template. Computational design will be performed with the program RosettaDesign (24) to optimize the shape complementarity between the protein and the amino acid. We will introduce the suggested mutations into the gene for the NAAB, express and purify the protein, and reassess the binding properties of the new mutant NAAB.

D. NAABs for Phosphorylated Amino Acids

In accordance with various aspects of the present invention, the NAABs may also include reagents capable of specifically binding to phosphorylated N-terminal amino acids (e.g., phosphotyrosine, phosphoserine, and phosphothreonine).

The proteome is elaborated by post-translational modifications. These marks are reversible and provide a snapshot of the current state of a cell with respect to signaling pathways and other regulatory control. Side chain phosphorylation, which primarily occurs on tyrosine, serine, and threonine residues, is a well-known post-translational modification. However, characterization of phosphorylated amino acids by mass spectrometry is difficult. Phosphate groups can be altered or lost during the ionization process, and sample enrichment is typically required to cope with issues of dynamic range (2). Identification of phosphorylated amino acids using digital protocols (e.g., DAPES) is improved because of the improved dynamic range and mild buffer conditions afforded by the present invention. Moreover, the ability to distinguish between phosphorylated and unphosphorylated amino acids could have a huge impact for characterizing cellular and disease states.

NAABs that specifically bind to either phosphoserine, phosphotyrosine, or phosphothreonine can be made by modifying certain tRNA synthetases to include one or more mutations. For example, methanogenic archaea possess an RS for phosphoserine. In contrast to most organisms, methanogenic archaea lack a CysRS. In these organisms, phosphoserine (Sep) is first ligated to the tRNA for cysteine, and then converted to Cys-tRNA in a subsequent step. A crystal structure of SepRS, a class II synthetase in complex with Sep is available from the PDB (pdb code: 2DU3 (36)).

While there are no known phosphotyrosine tRNA synthetases, RSs for several chemically similar analogs have been obtained via directed evolution (37-39). The class I TyrRS from Methanococcusjannaschii is the parental protein for these mutants, and a crystal structure is available for engineering (pdb code: 1U7D (apo), 1J1U(holo)). There are several relevant mutant RSs, most notably for sulfotyrosine (37), p-acetyl-L-phenylalanine (pAF), and p-carboxymethyl-L-phenylalanine (pCMF).

Given the stereochemical similarity between phosphate and sulfate, and the fact that phosphatases and phosphoryltransferases often accept sulfates and sulfuryl groups as substrates (40), it has been found that the sulfotyrosine RS will recognize phosphotyrosine without further modification. The pAF RS, for which a crystal structure is available (pdb code: 1ZH6), differs from the sulfotyrosine RS at only two residues (38). Thus, if necessary a template is available for structural modeling and further protein engineering.

There are no reported pThrRSs or previously engineered RSs that recognize pThr analogs. Consequently, generation of a pThrRS may require more extensive protein engineering. We will approach this task from two directions. First, we will use computational design to widen the binding pocket of SepRS to accommodate the additional methyl group present in pThr. Second, we will use the motif-directed design approach to graft previously observed phosphate-binding interactions into the binding pocket of ThrRS. The PDB contains hundreds of examples of binding interactions involving phosphotyrosine (308 examples), phosphoserine (385), and phosphothreonine (325) that are suitable for building a motif library of protein-phosphate interactions. The same design protocol successfully used to switch the specificity of eMAP to eLAP will be applied to transplant these interaction motifs into E. coli ThrRS. Mutagenesis of SepRS and ThrRS proteins will be performed using the QuikChange protocol. We will purchase a peptide with the sequence pTGMMGSSC for attachment to the nanogel surface and characterization of binding by single-molecule detection.

It is expected that a NAAB for pThr may also bind to N-terminal pSer. If so, this NAAB can be used for pThr and pSer, and then the specific amino acid can be inferred by evaluating the surrounding sequence to map the peptide onto a reference proteome library. Alternatively, if de novo, phosphorylation-sensitive sequencing is required, then the efficacy of applying a pSer NAAB, detecting binding, then applying a pThr NAAB without an intervening wash step will be assessed. Bound pSer termini will be blocked by the pSer NAAB, and only additional fluorescent spots will be identified as pThr residues.

E. Fluorophores

In accordance with various aspects of the present invention, the NAABs are fluorescently labeled such that when a NAAB binds to an amino acid, fluorescence can be detected. Fluorophores useful for fluorescently labels on the NAABs include, for example, but are not limited to Cy3 and Cy5. The fluorophores are usually coupled on-specifically to free amine groups (e.g., lysine side chains) of the NAABs.

II. Method of Making NAABs by Introducing Mutations into tRNA Synthetase Proteins The present invention also relates to a method for making a NAAB by introducing mutations into the amino acid sequence of a tRNA synthetase (RS) to produce a NAAB that selectively binds to a particular N-terminal amino acid. For example, such methods can involve introducing one or more mutations into a naturally occurring RS (e.g., into a wild-type E. coli RS). Such methods can also involve introducing one or more additional mutations into an RS that already includes one or more amino acid mutations in its sequence as compared to the sequence of a corresponding wild-type RS.

The methods for making NAABs comprise identifying the amino acid binding domain of a tRNA synthetase, introducing one or more mutations into the amino acid binding domain to create a NAAB, and assaying the NAAB for specific binding to an N-terminal amino acid of a polypeptide.

Where the tRNA synthetase is a class I tRNA synthetase, identification of the amino acid binding domain can be accomplished, for example, by constructing a sequence alignment that aligns pairwise the amino acid sequences of two or more class I tRNA synthetases with one another, wherein one of the class I tRNA synthetases has a previously defined amino acid binding domain. This allows for identification of corresponding sequence positions between proteins in order to share useful mutations between NAABs. Thus, in certain aspects of these methods, the tRNA synthetase is a first class I tRNA synthetase and the identifying step comprises aligning an amino acid sequence of the first class I tRNA synthetase with an amino acid sequence of a second class I tRNA synthetase having a previously defined amino acid binding domain. For example, the amino acid binding domain of E. coli MetRS is known to be encompassed within amino acids 4 to 547 of the protein. Thus, the amino acid sequence of the second class I tRNA synthetase can comprise the amino acid sequence of full-length E. coli MetRS (SEQ ID NO: 5) or a fragment thereof which includes the amino acid binding domain. In addition, the amino acid sequence of the second class I tRNA synthetase can comprise a wild-type sequence or can comprise a sequence containing one or more mutations, so long as the presence of the mutations does not significantly impair the ability of the sequence to align with other class I tRNA synthetases. For example, the amino acid sequence of the second class I tRNA synthetase can comprise the amino acid sequence of the engineered MetRS fragment described above (of SEQ ID NO: 4), which contains four amino acid substitutions as compared to the corresponding fragment of wild-type *E. coli* MetRS. The identifying step can comprise aligning the amino acid sequence of full-length *E. coli* MetRS (SEQ ID NO: 5) or a fragment thereof which includes the amino acid binding domain with a class I tRNA synthetase selected from the group consisting of arginine, cysteine, glutamate, glutamine, isoleucine, leucine, lysine, methionine, tyrosine, tryptophan, and valine.

The method can also involve constructing a multiple sequence alignment that aligns the amino acid sequences of the first class I tRNA synthetase, the second class I tRNA synthetase, and at least one additional class I tRNA synthetase. For example, the multiple sequence alignment can align the sequences of at least five, at least seven, or at least nine class I tRNA synthetases. Thus, the multiple sequence alignment can align the amino acid sequence of full-length *E. coli* MetRS (SEQ ID NO: 5) or a fragment thereof which includes the amino acid binding domain with the amino acid sequences of at least two other class I tRNA synthetases selected from the group consisting of arginine, cysteine, glutamate, glutamine, isoleucine, leucine, lysine, methionine, tyrosine, tryptophan, and valine.

Following alignment of an amino acid sequence of a first class I tRNA synthetase with an amino acid sequence of a second class I tRNA synthetase having a previously defined amino acid binding domain, the boundaries of the amino acid binding domain of the first class I tRNA synthetase can be identified using the known boundaries of the amino acid binding domain in the second class I tRNA synthetase as a guide.

Once the amino acid binding domain of a given class I tRNA synthetase has been identified, mutations homologous to the four substitution mutations present in the engineered MetRS fragment described above are introduced into the amino acid binding domain of the class I tRNA synthetase. Thus, for each class I tRNA synthetase, the leucine at position 13 of wild-type *E. coli* MetRS is replaced with a serine (L13S), the phenylalanine at position 260 is replaced with a leucine (Y260L), the aspartic acid at position 296 is replaced with a glycine (D296G), and the histidine at position 301 is replaced with a leucine (H301L).

The binding affinity of each NAAB containing these mutations against a panel of N-terminal amino acids can be predicted in silico using a computer modeling program (e.g., the Rosetta modeling program). Any NAAB with significant predicted cross-binding with undesired target peptides can be subjected to computational redesign for specificity using a multi-state strategy (11). For example, the computational redesign may identify one or more additional mutations likely to improve the binding specificity of the NAAB for a particular N-terminal amino acid. In this approach, structural models of the NAAB in complex with both the desired and undesired amino acids are constructed in silico.

If computational redesign identifies any further mutations as being likely to improve the binding specificity of the NAAB for a particular N-terminal amino acid, such mutations can be introduced into the NAAB.

Similar methods can be used to identify the amino acid binding domains of the class II RSs and introduce mutations into those domains to produce NAABs that selectively bind to N-terminal amino acids that are activated by class II RSs (Ala, Pro, Ser, Thr, His, Asp, Asn, Lys, Gly, and Phe).

The catalytic domain of class II RS proteins contains the amino acid specificity for the enzyme, and these domains can be used as a starting point for developing additional NAABs. Although class II RSs function as multimers, the catalytic domain of the HisRS from *E. coli* can be made monomeric by liberating it from its activation domain (20). The crystal structure of the enzyme in complex with histidyl-adenylate is available (pdb code 1KMM (21)), and can serve as a basis for computational structure-based design. At least one RS crystal structure is available for each of the amino acids activated by class II RSs (Ala, Pro, Ser, Thr, His, Asp, Asn, Lys, Gly, and Phe).

For example, the amino acid binding domains for each of the class II RSs can be identified using the monomeric fragment of *E. coli* HisRS (SEQ ID NO: 9) as a guide to identify corresponding domains in other class II RSs. Structural alignments between the monomeric fragment of *E. coli* HisRS (residues 3-180 and corresponding domains in other class II RSs can be obtained from the Dali web server (22). Multiple sequence alignments for the conserved class II catalytic domain can be obtained from the Pfam database (19). Using these alignments, boundaries for the amino acid binding domains for class II RSs can be identified.

Thus, in some aspects of the method of a making a NAAB, the tRNA synthetase is a first class II tRNA synthetase and the step of identifying the amino acid binding domain comprises aligning an amino acid sequence of the first class II tRNA synthetase with an amino acid sequence of a second class II tRNA synthetase having a previously defined amino acid binding domain. The amino acid sequence of the second class II tRNA synthetase can comprise the amino acid sequence a monomeric fragment of *E. coli* HisRS that contains the amino acid binding domain (e.g., SEQ ID NO: 9). The amino acid sequence of the second class II tRNA synthetase can comprise a wild-type sequence or can comprise a sequence containing one or more mutations, so long as the presence of the mutations does not significantly impair the ability of the sequence to align with other class I tRNA synthetases.

For example, the identifying step can comprise aligning the amino acid sequence of the monomeric fragment of *E. coli* HisRS with a corresponding domain of a class II tRNA synthetase selected from the group consisting of AlaRS, ProRS, SerRS, ThrRS, AspRS, AsnRS, LysRS, GlyRS, and PheRS.

The identifying step can also comprise constructing a multiple sequence alignment that aligns the amino acid sequences of the first class II tRNA synthetase, the second class II tRNA synthetase, and at least one additional class II tRNA synthetase. For example, the multiple sequence alignment can align the sequences of at least five, at least seven, or at least nine class II tRNA synthetases. The multiple sequence alignment can align the amino acid sequence of a monomeric fragment of *E. coli* HisRS that contains the amino acid binding domain with a corresponding domain of at least two other class II tRNA synthetases selected from the group consisting of AlaRS, ProRS, SerRS, ThrRS, AspRS, AsnRS, LysRS, GlyRS, and PheRS. Alternatively, the multiple sequence alignment can align the amino acid sequence of a monomeric fragment of *E. coli* HisRS that contains the amino acid binding domain with corresponding domains of AlaRS, ProRS, SerRS, ThrRS, AspRS, AsnRS, LysRS, GlyRS, and PheRS.

Once the amino acid binding domain of a given class II tRNA synthetase has been identified, mutations (e.g., substitution mutations) are introduced into the amino acid binding domain in order to increase the binding affinity of the domain for a particular N-terminal amino acid.

As with the methods involving class I tRNA synthetases, the methods involving class II tRNA synthetases can also further comprise using a computer modeling program to predict the binding affinity of the NAAB against a panel of N-terminal amino acids. In addition, the NAAB can be subjected to computational redesign to identify one or more additional mutations to improve the binding specificity of the NAAB for a particular N-terminal amino acid. Any additional mutations identified using computational redesign can then be introduced into the NAAB.

The NAABs designed and made using any of the above methods can cloned into an expression vector, expressed in a host cell (e.g., in an *E. coli* host cell), purified, and assayed for specific binding to an N-terminal amino acid of a polypeptide. For example, the binding activity for each NAAB can be assayed against a standard set of polypeptides having different N-terminal residues (e.g., custom synthesized peptides of the form XGMMGSSC, where X is a variable position occupied by each of the twenty amino acids).

For NAABs derived from class II tRNA synthetases, if any of the *E. coli* protein fragments prove to are insoluble or perform poorly as NAABs, protein design can be used to redesign hydrophobic residues that become exposed upon monomerization. If a crystal structure is unavailable for the *E. coli* protein, a synthetic gene for an RS with an experimentally determined structure can be obtained. The availability of structures for these proteins allows application of protein surface redesign if the domain truncation results in loss of solubility, binding pocket redesign for enhanced affinity if binding is weak, or multi-state design for enhanced specificity if promiscuous binding is observed (11).

In any of the above methods, the tRNA synthetase amino acid sequences can be *E. coli* tRNA synthetase amino acid sequences.

In addition, in any of the above methods, the sequences can be aligned pairwise by various methods known in the art, for example, using the hidden Markov models available in the Pfam database (19), dynamic programming, and heuristic methods like BLAST.

Also, in any of the above methods, mutations that favor desired binding and disfavor undesired binding can be introduced into any of the wild-type proteins described above by various methods, for example, using mutagenic primers to introduce mutations via site-directed mutagenesis, PCR-based mutagenesis and Kunkel mutagenesis. Various computer programs can be used to design suitable primers (e.g., the QUICKCHANGE (Aligent Technologies) primer design program).

II. Polypeptide Sequencing Using NAABs

In accordance with various aspects of the present invention, the NAABs discussed above are used as reagents in a method of polypeptide sequencing. Generally, the method of sequencing a polypeptide comprises the steps of:
(a) contacting the polypeptide with one or more fluorescently labeled N-terminal amino acid binding proteins (NAABs);
(b) detecting fluorescence of a NAAB bound to an N-terminal amino acid of the polypeptide;
(c) identifying the N-terminal amino acid of the polypeptide based on the fluorescence detected;
(d) removing the NAAB from the polypeptide;
(e) optionally repeating steps (a) through (d);
(f) cleaving the N-terminal amino acid of the polypeptide via Edman degradation; and
(g) repeating steps (a) through (f) one or more times.

In step (a), the polypeptide is contacted with one or more NAABs. In various aspects, the polypeptide is contacted with a single type of NAAB that selectively binds to a single type of N-terminal amino acid residue (e.g., a NAAB that selectively binds to N-terminal alanine residues or a NAAB that selectively binds to N-terminal methionine residues). In other embodiments, the polypeptide is contacted with a mixture of two or more types of NAABs that each selectively binds to different amino acid residues. For example, the mixture may comprise two NAABs such as a NAAB that selectively binds to N-terminal alanine residues and a NAAB that selectively binds to N-terminal cysteine residues. A mixture comprising two or more NAABs that selectively bind to different amino acid residues is especially useful when sequencing several polypeptides simultaneously. Introducing multiple different NAABs also reduces sequencing time because multiple N-terminal amino acid residues can be identified during a single iteration of steps (a) through (d). As such, in various embodiments, the method comprises sequencing a plurality of polypeptides. These embodiments are especially suited for high throughput sequencing methods.

In various aspects of the invention, the polypeptide may be immobilized on a substrate prior to contact with the one or more NAABs. The peptide may be immobilized on any suitable substrate. For example, nanogel substrates have been developed with low non-specific adsorption of proteins and the ability to visualize single attached molecules on this surface (8, 9). Moreover, a plurality of polypeptides may be immobilized on the substrate for sequencing. Immobilizing a plurality of polypeptides is especially suited for high throughput sequencing methods.

The NAABs of the present inventions are fluorescently labeled with a fluorophore such that when a NAAB binds to a N-terminal amino acid, fluorescence emitted by the fluorophore can be detected by an appropriate detector. Suitable fluorophores include, but are not limited to Cy3 and Cy5. Fluorescence can suitably be detected by detectors known in the art. Based on the fluorescence detected, the N-terminal amino acid of the polypeptide can identified.

In aspects of the method where the contacting step comprises contacting the polypeptide with a mixture of two or more types of NAABs that each selectively binds to different amino acid residues, each type of NAAB is suitably labeled with different fluorophores having different fluorescence emission spectra. For example, the contacting step can comprise contacting the polypeptide with a first type of NAAB and a second type of NAAB, wherein the first type of NAAB selectively binds to a first type of N-terminal amino acid residue and the second type of NAAB selectively binds to a second type of N-terminal amino acid residue different from the first type of N-terminal amino acid residue. In such methods, the first type of NAAB is suitably coupled to a first fluorophore and the second type of NAAB is suitably coupled to a second fluorophore, wherein the first and second fluorophores have different fluorescence emission spectra.

In step (d), the one or more NAABs are removed from the polypeptide(s). Removing the one or more NAABs includes removing any excess NAABs present in solution and/or removing any NAABs that are bound to N-terminal amino acids of the polypeptides. Removal of the NAABs is suitably accomplished by washing the polypeptide with a suitable wash buffer in order to cause dissociation of any bound NAABs. In embodiments where the polypeptide is immobilized on a solid substrate, the reagent may be removed by contacting the substrate with a suitable wash buffer.

Steps (a)-(d) may be repeated any number of times until the N-terminal amino acid of the polypeptide has been identified. In embodiments where a plurality of polypeptides is being sequenced, steps (a)-(d) may be repeated any number of times until all of the N-terminal amino acids of the polypeptide(s) have been identified. During each repetition, a different NAAB or a set of NAABs may be used in step (a) to probe the N-terminal amino acid of the polypeptide(s). Thus, for example, where step (a) comprises contacting the polypeptide with a single type of NAAB that selectively binds to a single type of N-terminal amino acid residue, it may be necessary to repeat steps (a) through (d) up to 24 or more times in order to probe the polypeptide with a NAAB specific for each of the twenty standard amino acids, for PITC-derivatized lysine, and for each of the three common phosphorylated amino acids. Alternatively, where step (a) comprises contacting the polypeptide with two or more different types of NAABs simultaneously, fewer repetitions of steps (a) through (d) will be necessary to identify the N-terminal amino acid of the polypeptide.

After the N-terminal amino acid has been identified or after all of the N-terminal amino acids have been identified (when sequencing multiple polypeptides simultaneously), the N-terminal amino acid(s) may be cleaved from the polypepitde(s) via Edman degradation. Generally, the Edman degradation comprises reacting the N-terminal amino acid of the polypeptide with phenyl isothiocyanate (PITC) to form a PITC-derivatized N-terminal amino acid, and cleaving the PITC-derivatized N-terminal amino acid. In various aspects of the invention, the modified N-terminal amino acid may be cleaved using an Edman degradation enzyme as described in further detail below. In other embodiments, the modified N-terminal amino group may be cleaved by methods known in the art including contact with acid or exposure to high temperature. In these aspects, any substrate comprising the immobilized polypeptide(s) should be compatible with the acidic conditions or high temperatures.

FIG. 1 provides a diagrammatic representation of the steps of a method of polypeptide sequencing according to the present invention. In step 1 of FIG. 1, multiple polypeptide molecules are immobilized on a substrate. The individual peptide molecules are suitably spatially segregated on the substrate. Analyte proteins may be fragmented into two or more polypeptides prior to immobilization on the substrate.

In step 2 of FIG. 1, the immobilized polypeptides are contacted with a fluorescently labeled NAAB and fluorescence of the NAAB bound to the N-terminal amino acid of any of the peptides is detected. An image of the substrate is suitably captured at this stage. Subsequently, the NAAB is washed off the substrate. This cycle of binding, detection, and removal of the NAAB is repeated until the N-terminal amino acids of all of the immobilized polypeptides have been identified (step 3). Next, in step 4, the N-termini of the polypeptides are reacted with phenyl isothiocyanate (PITC) (black ovals in FIG. 1). In step 5, an Edman degradation ("Edmanase"), catalyzes the removal of the PITC-derivatized N-terminal amino acid under mild conditions. In each complete cycle, one amino acid is sequenced from each peptide and a new N-terminus is generated for identification in subsequent cycles (step 6).

In the polypeptide sequencing methods described herein, some of the NAABs may bind smaller, sterically similar off-target amino acids. For example, the isoluecine-specific NAAB derived from IleRS and the threonine-specific NAAB derived from ThrRS may bind N-terminal valine and serine residues, respectively, in addition to their desired targets. However, this does not hinder the effectiveness of this protein sequencing technique. Although various aspects of the present invention relate to a reagent comprising NAABs for all twenty amino acids, the optimal set size for actual sequencing may be less than twenty. Reducing the number of NAABs involves trading off absolute specificity for fewer binding molecules by using a reduced alphabet for protein sequences. It may be more efficient to identify multiple amino acids (such as isoleucine and valine) with a single NAAB, and treat these amino acids as interchangeable when matching against a sequence database. It is also possible to enforce specificity in digital protocols such as DAPES by introducing the NAABs in a step-wise fashion. For example, the valine-specific NAAB derived from ValRS can be added before the isoleucine-specific NAAB derived from IleRS, with the intention of identifying and capping N-terminal valine residues before molecules intended to target isoleucine residues that can bind to them.

Methods of the present invention possess attractive features relative to mass spectrometry. Because detection operates at the single molecule level, this method will have excellent dynamic range, and will be appropriate for extremely small amounts of sample. Furthermore, the digital nature of the detection produces inherently quantitative data. Finally, because all steps can be carried out in neutral aqueous buffer, post-translation modifications (e.g., phosphorylations) remain stable and available for analysis.

IV. Enzymatic Edman Degradation

In another aspect, the present invention is directed to a method and reagents for enzymatic Edman degradation (i.e., cleaving the N-terminal amino acid of a polypeptide). In accordance with this aspect, one or more enzymes are provided that catalyze the cleavage step of the Edman degradation in aqueous buffer and at neutral pH, thereby providing an alternative to the harsh chemical conditions typically employed in conventional Edman degradation. In one aspect, the Edman degradation enzyme a modified cruzain enzyme. Cruzian is a cysteine protease in the protozoa *Trypanosoma cruzi* and was discovered to possess many of the desired characteristics for creating an Edman degradation enzyme.

In conventional Edman degradation, polypeptides are sequenced by degradation from their N-terminus using the Edman reagent, phenyl isothiocyanate (PITC). The process requires two steps: coupling and cleavage. In the first step (coupling), the N-terminal amino group of a peptide reacts with phenyl isothiocyanate to form a thiourea. In the second step, treatment of the thiourea with anhydrous acid (e.g., trifluoroacetic acid) results in cleavage of the peptide bond between the first and second amino acids. The N-terminal amino acid is released as a thiazolinone derivative. The thiazoline derivative may be extracted into an organic solvent, dried, and converted to the more stable phenylthiohydantoin (PTH) derivative for analysis. The most convenient method for identifying the PTH-amino acids generated during each sequencing cycle is by UV absorbance and HPLC chromatography. Each amino acid is detected by it UV absorbance at 269 nm and is identified by its characteristic retention time.

In digital protocols, such as DAPES, the N-terminal amino acid has already been identified. Therefore, there is no need to generate or detect a phenylthiohydantoin derivative of the terminal amino acid. However, the strongly acidic conditions typically used in the cleavage step of conventional Edman degradation protocols are incompatible with the substrate surface upon which the polypeptides are immobilized for single molecule protein detection (SMD) (e.g., a nanogel surface). One modification of the conventional Edman degradation dispenses with the acidic conditions promotes cleavage with elevated temperature (e.g., 70-75° C.) instead (25). However, some substrate surfaces used to immobilize peptides include bovine serum albumin (BSA), which has a melting temperature of approximately 60° C. in the absence of stabilizing additives (26). Further, repeated cycles of heating and cooling of the substrate surface (e.g., nanogel) may be undesirable. Thus, the present invention provides a method of performing the Edman degradation which dispenses with both acidic conditions and elevated temperature. Advantageously, an enzyme has been developed which accomplishes the cleavage step in a neutral, aqueous buffer. This enzyme avoids acidic conditions and high temperatures and decreases the cycle time for polypeptide sequencing by reducing or eliminating the need to change buffer and temperature conditions repeatedly.

The Edman degradation enzyme (or "Edmanase") according to the present invention accomplishes the chemical step of the N-terminal degradation by nucleophilic attack of the thiourea sulfur atom on the carbonyl group of the scissile peptide bond. As noted, the enzyme was made by modifying cruzain, a cysteine protease from the protozoa *Trypanosoma cruzi* (SEQ ID NO: 30). Cruzain prefers hydrophobic amino acids at the S2 position relative to the scissile bond, which corresponds to the phenyl moiety of the Edman reagent. The protease is relatively insensitive to the identity of the amino acid at the S1 position (29), allowing for promiscuous cleavage of diverse N-terminal residues. Furthermore, this protein has been the subject of extensive structural characterization (27).

Figure 4A:
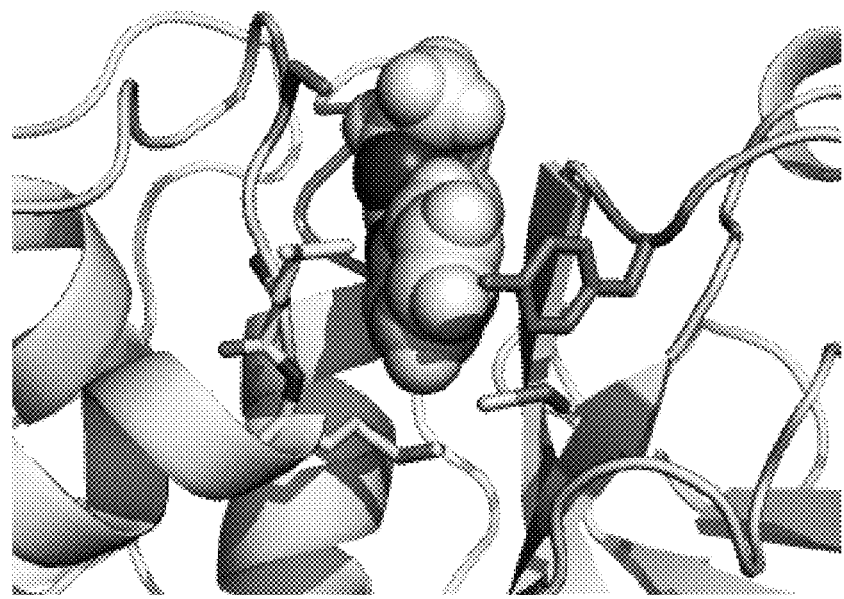
FIG. 4A-4B depict three mutations (indicated by the arrows) introduced into a model of cruzain (pdb code: 1U9Q (27)) to accommodate the phenyl moiety of the Edman reagent phenyl isothiocyanate.
Figure 4B:
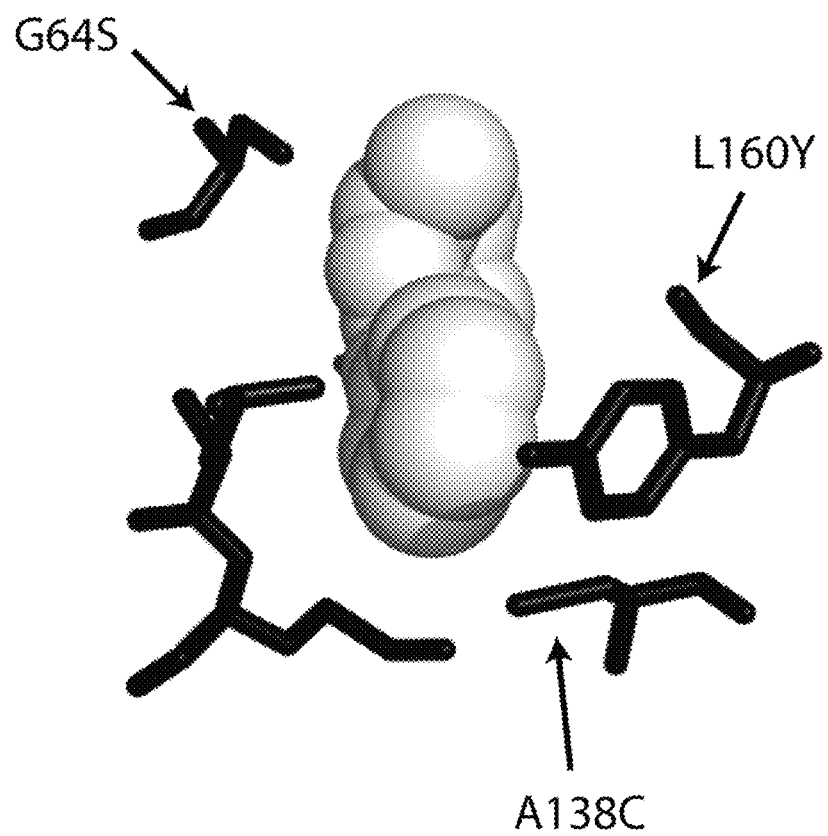
Figure 5A:
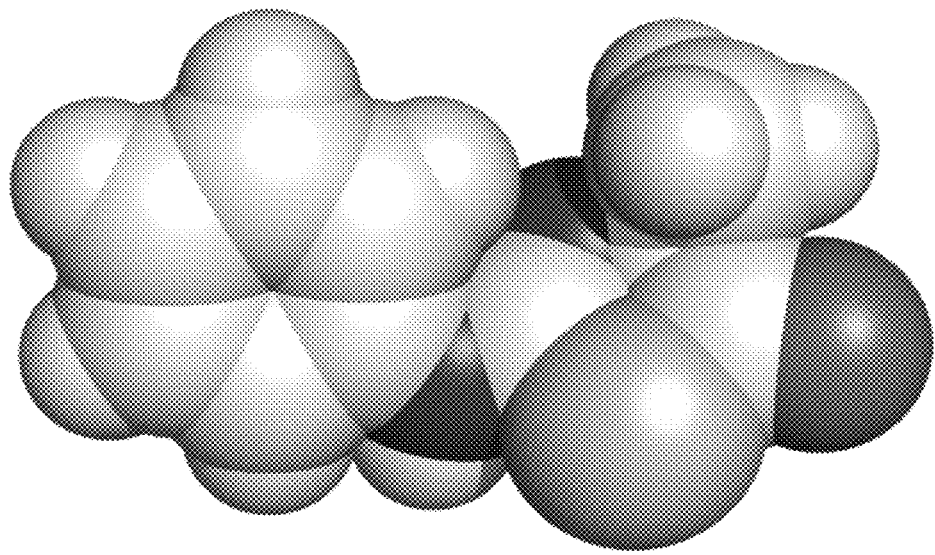
FIG. 5A depicts a model for a cleavage intermediate for Edman degradation generated using experimental small molecules structures for similar compounds and geometrically optimized using quantum chemistry calculations.
Figure 5B:
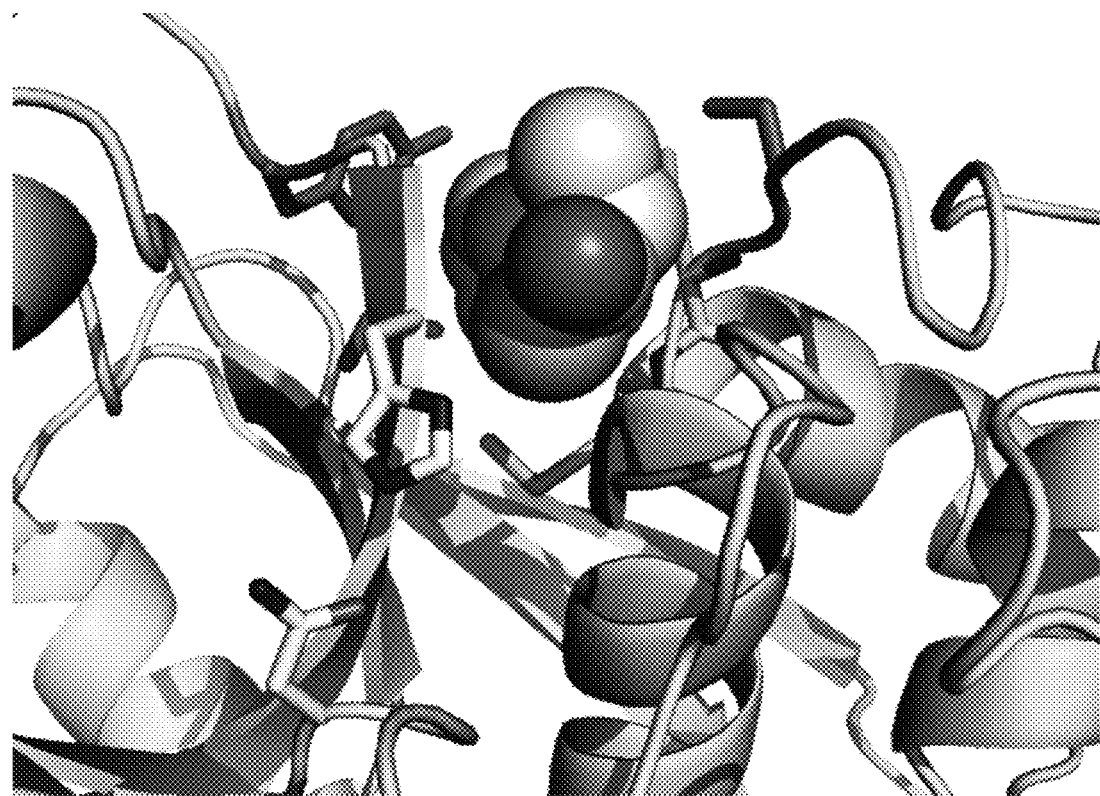
FIG. 5B shows the model for the intermediate fitted into the active site cleft of the enzyme cruzain. The wild-type catalytic cysteine was removed. The activating residues (the other two components of the 'catalytic triad') were retained. These are a histidine and asparagine that are intended to activate the sulfur atom in the Edman reagent for nucleophile attack on the peptide bond.

The Edman degradation enzyme differs from the wild-type of cysteine protease cruzain at four positions. One mutation (C25G) removes the catalytic cysteine residue while three mutations (G65S, A138C, L160Y) were selected to create steric fit with the phenyl moiety of the Edman reagent (PITC). FIG. 4A-4B depicts latter three mutations (indicated by the arrows) introduced into a model of cruzain (pdb code: 1U9Q (27); SEQ ID NO: 30) to accommodate the phenyl moiety of the Edman reagent phenyl isothiocyanate. FIG. 4A depicts a model for the cleavage intermediate of an N-terminal alanine residue in the active site cleft. In addition to the engineered residues, two wild-type residues (shown in green sticks) contribute to forming a complementary pocket. FIG. 4B depicts a space-filling representation of the packing of the phenyl ring by protein side chains. The methyl group of the ligand (in gray at the top of the panel) corresponds to the side chain of the N-terminal residue to be cleaved, and is not involved in the tight packing between enzyme and substrate. The enzyme was expressed and purified.

Accordingly, one aspect of the present invention relates to an isolated, synthetic, or recombinant Edman degradation enzyme comprising an amino acid sequence having a glycine residue at a position corresponding to position 25 of wild-type *Trypanosoma cruzi* cruzain; a serine residue at a position corresponding to position 65; a cysteine residue at a position corresponding to position 138; and a tryptophan residue at a position corresponding to position 160.

The remaining amino acid sequence of the Edman degradation enzyme comprises a sequence similar to that of wild-type *Trypanosoma cruzi* cruzain, but may contain additional amino acid mutations (including deletions, insertions, and/or substitutions, so long as such mutations do not significantly impair the ability of the Edman degradation enzyme to cleave PITC-derivatized N-terminal amino acids. For example, the remaining amino acid sequence can have at least about 80%, or at least 85%, at least 90%, at least 93%, at least 95%, at least 96%, at least 87%, at least 98%, or at least 99% sequence identity with the sequence of the wild-type *Trypanosoma cruzi* cruzain.

In some aspects of the invention, the Edman degradation enzyme comprises the sequence of SEQ ID NO: 29. For example, the Edman degradation enzyme can consist of the sequence of SEQ ID NO: 29.

In various aspects of the invention, the reagents for enzymatic Edman degradation comprise two or more enzymes. For example, one point of concern is the ability to cleave proline residues. If a single mutant of cruzain cannot accomplish this reaction, then an additional enzyme would be required. Naturally occurring enzymes cleave dipeptides of the form Xaa-Pro from the N-terminus of peptides, for example, quiescent cell proline dipeptidase (QPP) (35), and Xaa-Pro amino peptidase (pdb code: 3OVK). PITC-coupled N-terminal proline is chemically and sterically very similar to a dipeptide. Therefore, these enzymes are excellent starting points for engineering a proline-specific activity.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above products, compositions and processes without departing from the scope of the invention, it is intended that all matter contained in the above description and shown in the accompanying drawings shall be interpreted as illustrative and not in a limiting sense.

EXAMPLES

The following non-limiting examples are provided to further illustrate the present invention.

Example 1. eLAP: A NAAB that Specifically Binds to N-Terminal Leucine Residues

In this example, an *E. coli* methionine aminopeptidase (eMAP) was modified to create a NAAB that binds specifically to N-terminal leucine residues. Two mutually compatible leucine-contacting interactions were identified from the protein data bank (PDB) (15) that could be incorporated into the eMAP structure. The surrounding protein residues of eMAP were redesigned around these two interactions. The resulting NAAB for leucine (eLAP) has 19 amino acid mutations relative to eMAP.

Figure 2A:
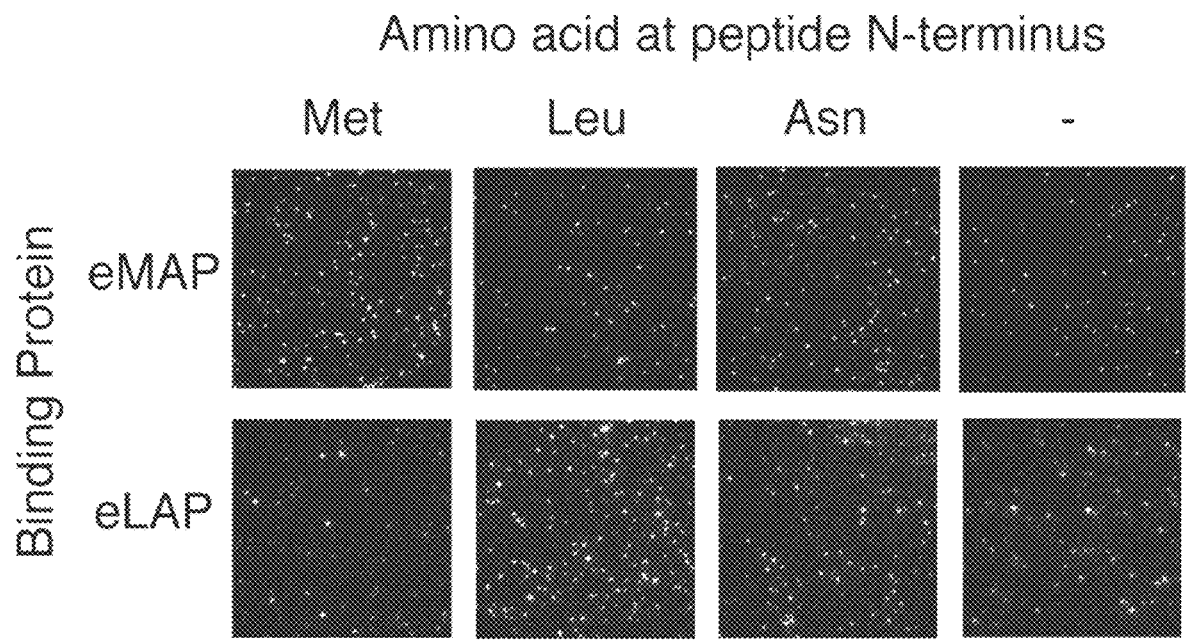
FIGS. 2A-2B show the binding specificity of wild-type *E. coli* methionine aminopeptidase (eMAP) and an engineered leucine-specific aminopeptidase (eLAP) of the present invention in a single-molecule detection experiment.
Figure 2B:
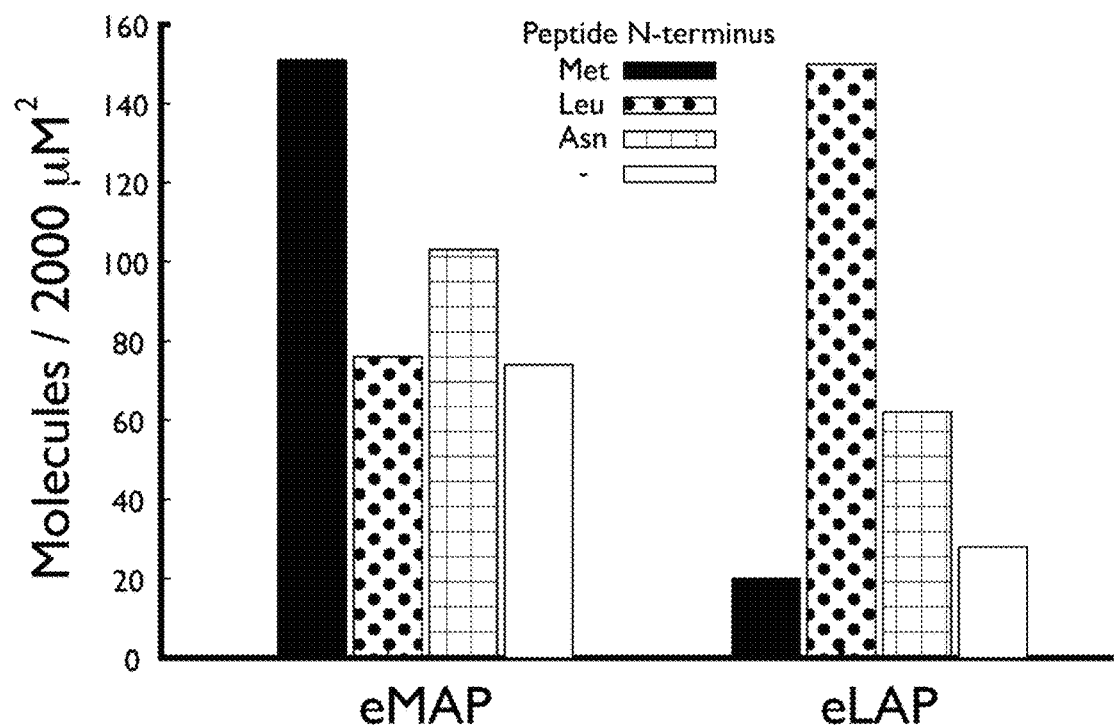

The eMAP and eLAP proteins were expressed and assayed for binding against a panel of peptides with different N-termini. The NAAB for N-terminal leucine amino acids was non-specifically labeled with Cy5 fluorophore on lysine side chains. Synthetic peptides with either N-terminal methionine, leucine, or asparagine amino acids were coupled to a nanogel surface by thiol linkage. An additional experiment was performed with no peptide added. The labeled NAAB was briefly incubated with the immobilized peptide, and unbound protein was removed by washing. Bound protein, which may be bound specifically to peptides or non-specifically to the surface, was imaged by total internal reflection fluorescence (TIRF) microscopy. Spots exceeding a detection threshold were deemed to indicate bound protein and were converted to a number of counts per field-of-view. FIGS. 2A-2B show the binding specificity of wild-type *E. coli* methionine aminopeptidase (eMAP) and eLAP in a single-molecule detection experiment. In FIG. 2A, fluorescently labeled eMAP and eLAP NAABs were visualized after binding to immobilized peptides with different N-terminal amino acids. FIG. 2B depicts histograms of quantitative binding. Digital analysis of NAAB binding for eMAP and eLAP showed that each NAAB was specific for the expected N-terminal amino acid. Both proteins exhibited roughly a 2:1 ratio of specific to non-specific binding.

These results demonstrate that individual N-terminal amino acids can be identified in an SMD format using NAABs that are selective for a particular amino acid.

Example 2. A NAAB that Specifically Binds to N-Terminal Methionine Residues

In this example, a truncated version of wild-type *E. coli* methionyl-tRNA synthetase (MetRS) from *E. coli*. was modified to make a NAAB that binds specifically to N-terminal methionine residues. A truncated version of MetRS (residues 1-547) having three amino acid mutations (L13S, Y260L, and H301L) that had been shown to pre-organize the binding site towards the methionine-bound conformation was obtained (16). A crystal structure is available of this mutant bound to free methionine (pdb code: 3h99). An additional mutation (D296G) was introduced to provide a more open binding pocket capable of accommodating a peptide and avoid steric clashes. This mutation was introduced into MetRS and the altered protein was expressed in *E. coli*. The gene encoding MetRS from genomic DNA was amplified and was cloned into the pET42a expression vector between the MfeI and XhoI sites. This yielded a genetic fusion of a thrombin-cleavable GST tag and MetRS. The mutations were introduced using the QuikChange protocol. The proteins were expressed at 16° C. overnight using the autoinduction protocol of Studier (17). The GST-MetRS fusion was purified from lysates by affinity chromatography using GSTrap columns on a Bio-Rad liquid chromatography system. Following purification, proteins were labeled with Cy5 fluorophore on lysine side chains for single-molecule binding assays.

Figure 3:
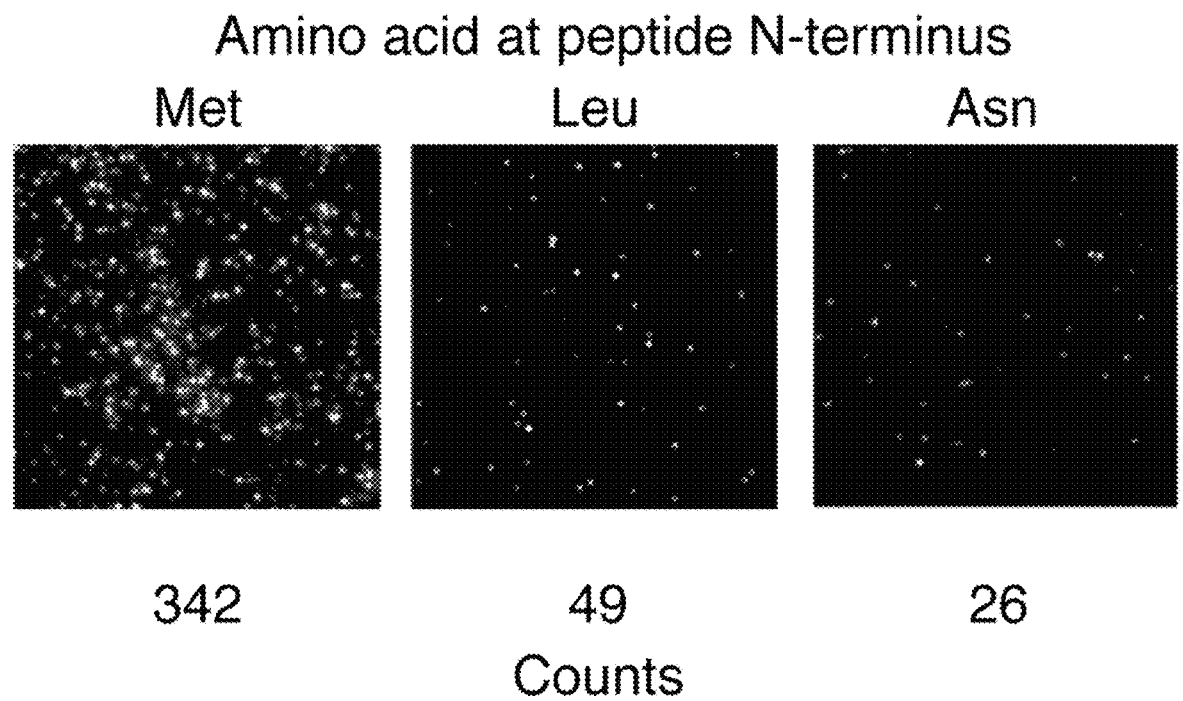
FIG. 3 shows the binding specificity of an engineered mutant of methionine tRNA synthetase (MetRS) of the present invention that exhibits binding specificity for surface-immobilized peptides with N-terminal methionines.

Using an SMD assay we then tested the specificity of our mutant MetRS for peptides with different amino acids at the N-terminus. Peptides of the form XGMMGSSC were purchased commercially, where X is methionine, leucine, or asparagine. The peptides were immobilized on a nanogel surface via thiol linkages, and the engineered MetRS domain was applied to the surface. Single molecule detection of bound MetRS was imaged by total internal reflection fluorescence (TIRF) microscopy. The resulting images are shown in FIG. 3. Quantitation of single-molecule binding events yields specific to non-specific binding of ~7:1 and ~13:1 for the alternate amino acids. The data in FIG. 3 show that the domain exhibits specific binding for N-terminal methionine, indicating that engineered RS fragments are excellent molecular reagents for DAPES and that computational protein design is an efficient method for producing NAABs with specificity for particular N-terminal amino acids.

Example 3. A NAAB that Specifically Binds to N-Terminal Histidine Residues

In this example, a histidine-tRNA synthetase (HISRS) from *E. coli* was modified to create a NAAB that binds specifically to N-terminal histidine residues. The fragment of wild-type HisRS from 1-320 was shown to be monomeric by others. After inspecting the crystal structure of HisRS, further residues were truncated from both ends. The initial fragment tested has from Lysine3 to Alanine180. Protein design was conducted to replace a long loop near the binding site with a shorter loop that would create a more open pocket and result in tighter binding to N-terminal histidine residues. This involved the replacement of an 11 residue loop (from Arginine113 to Lysine123) with a 4 residue turn, wherein the four residues of the inserted turn are Glycine, Asparagine, Alanine, and Proline. Thus, this NAAB comprises an internally truncated version of wild-type *E. coli* HisRS (residues 3-180; SEQ ID NO: 10) having seven fewer residues as compared to the wild-type sequence. The sequence of this N-terminal histidine-specific NAAB is provided by SEQ ID NO: 9.

Figure 7:
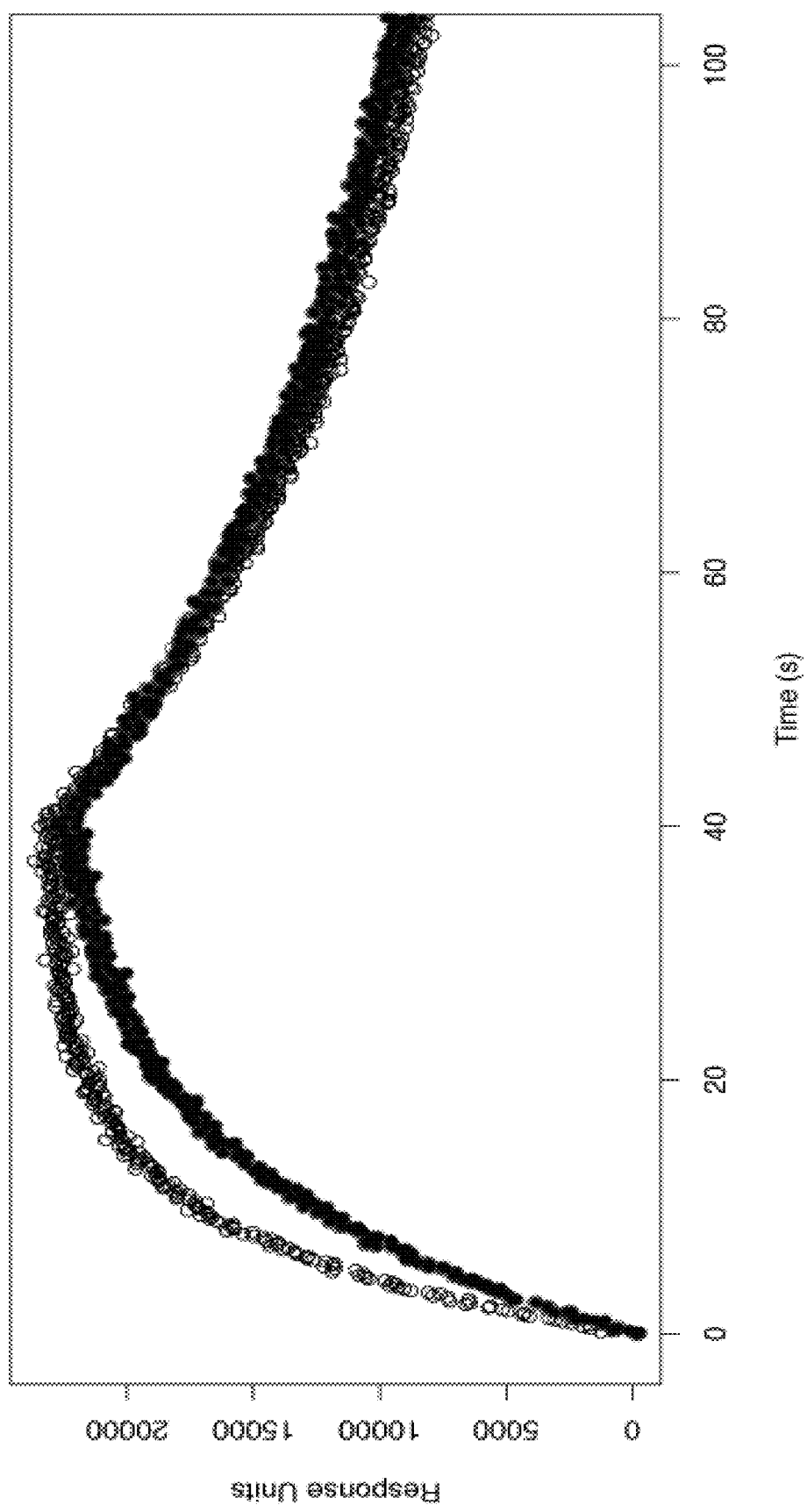
FIG. 7 is a trace plot of biolayer interferometry kinetics data showing the binding affinity of two proteins for peptides with N-terminal histidine residues: (1) engineered His NAAB (open circles); (2) native wild-type protein (solid circles).

FIG. 7 shows that engineered HisNAAB (SEQ ID NO: 10) exhibits enhanced binding affinity for peptides with N-terminal histidine residues as compared to the wild-type fragment. Biolayer interferometry kinetics data show that the engineered HisNAAB (data in open circles) binds N-terminal histidine with the same off-rate as the wild-type fragment (SEQ ID NO: 90 (data in solid circles), but with an enhanced on-rate. As a result, the engineered His NAAB binds with an approximately 10-fold improvement in binding affinity.

Example 4. Purification of an Edman Degradation Enzyme

A synthetic gene containing the Edman degradation enzyme was purchased from GenScript. The gene encoded a modified version of the cruzian enzyme of *T. cruzi* having the following substitution mutations: C25G, G65S, A138C, and L160Y.

The gene was inserted between an NdeI andan XhoI site in a pet42(a) (Novagen) expression vector and transformed into *E. coli*, BL-21(De3) chemically competent cells. Protein was then over-expressed following Studier's auto-induction protocol. Bacterial cells were harvested by centrifugation of the cell culture at 5000 rpm and 4° C. for 10 minutes. Cells were then suspended in 1×PBS with 10% glycerol and 6M guanidine chloride, pH 7.4. Cells were then lysed by sonication (15 seconds at 20% power, 8 times on ice). The cell lysate was centrifuged at 18000 rpm, 4 degrees for 20 minutes. The supernatant was then filtered through a 0.2 μm cellulose acetate filter. The filtered lysate was loaded onto a 5 mL HisTrap (Ni-NTA) column and washed with 5 column volumes of binding buffer (50 mM Tris-HCl, 150 mM NaCl, 6M guanidine chloride, 25 mM imidazole). Bound protein was then eluted in 50 mM Tris-HCl, 150 mM NaCl, 6M guanidine chloride, 500 mM imidazole. Purified fractions were prepared for SDS-PAGE analysis by mixing 2 parts sample with 1 part 4× loading dye. Samples were analyzed on 16% SDS-PAGE precast gels, and visualized by Coomassie staining. The purified protein was then refolded by successive, overnight dialyses into 1×PBS containing 5M, 3M, 1M, 0.5M, and 0M guanidine chloride. Protein concentration was determined using the calculated molar extinction coefficient and measuring the A280 on an ND-8000 spectrophotometer (Thermo Fisher Scientific).

Example 5. Substrates and Inhibitors for Edman Degradation Enzyme (Edmanase)

Single amino acid, aminomethylcoumarin (AMC) containing compounds were obtained from BAChem (Bubendorf, Switzerland). These included Arg-AMC, Asn-AMC, Phe-AMC, Met-AMC, Ala-AMC, and Pro-AMC. Phenylisothiocyanate (PITC) was purchased from Thermo-scientific and coupled to the N-terminus of each substrate by incubating for 10 minutes at room temperature in a 100 μL solution of acetonitrile:pyridine:water (10:5:3) with 5 μL of PITC. The derivatized substrate was then dried by rotary evaporation and suspended in 250 μL of 1× Phosphate Buffered Saline (PBS). Inhibitor compound, 1-(2-anilino-5-methyl-1,3-thiazol-4-yl)-ethanone, was ordered from Sigma-Aldrich (St. Louis, Mo.).

Example 6. Edmanase Activity Measurements

Figure 6:
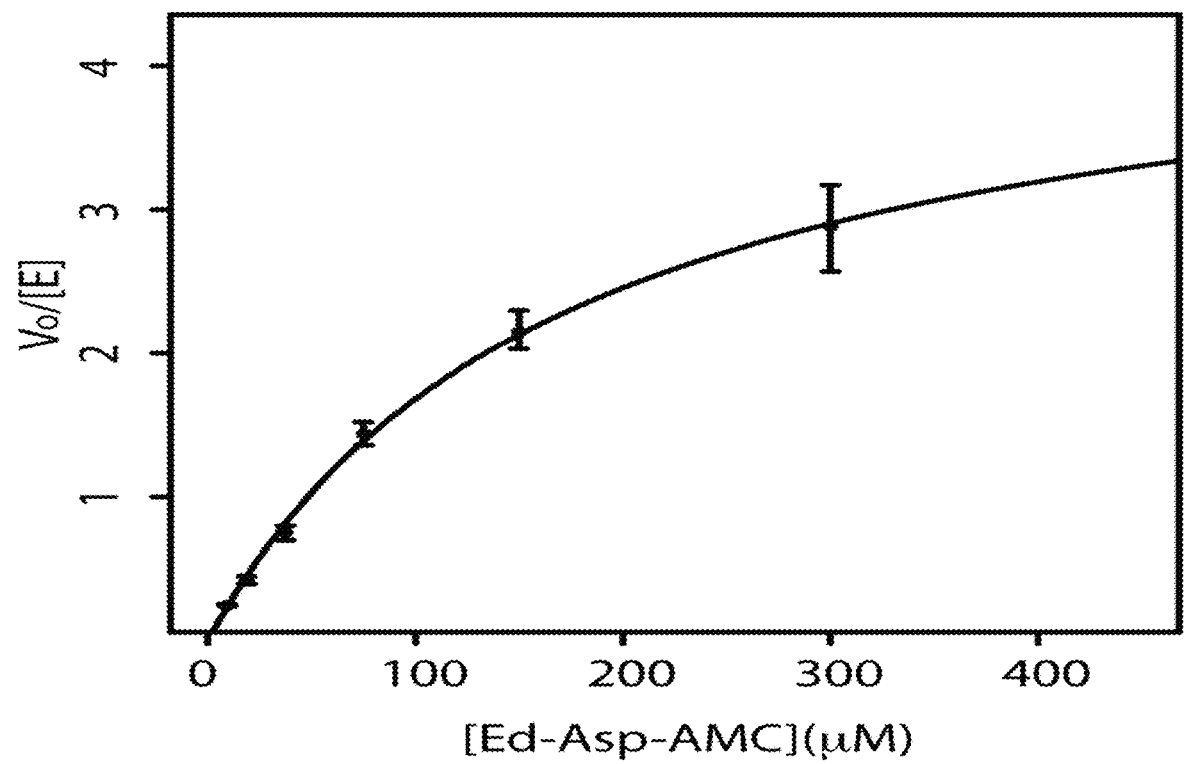
FIG. 6 is a graphical representation of kinetic data from cleavage experiments using an Edman degradation enzyme of the present invention and the substrate Ed-Asp-AMC.

The ability of the Edman degradation enzyme to perform N-terminal cleavage on six substrates of the form Ed-X-AMC, where Ed denotes the Edman reagent, X is an amino acid from the set (Ala, Asp, Phe, Met, Pro, Arg), and AMC is the fluorogenic amidomethylcoumarin group was characterized. Cleavage of the X-AMC bond was monitored by the appearance of fluorescence (FIG. 6). The engineered protein displayed activity against all six substrates to varying degrees (See Table below).

All kinetic measurements were performed in a 96-well corning plate on a BioTek Synergy2 plate reader at 30 degrees. Reactions were started by adding 5-20 μL of purified enzyme to 100 μL of 10 mM substrate solution. Final enzyme concentration was between 1 nM and 100 nM, depending on the experiment. Fluorescence of the cleaved product was measured by exciting at 370 nm (30 second intervals for 1-10 hours) and monitoring emissions at 460 nm. A standard curve using AMC from Invitrogen was referenced quantitate the amount of product formation.

TABLE

Measured kinetic rates for Edmanase

| Substrate (X-AMC) | $K_{cat}$ ($s^{-1}$) | $K_m$ (μM) | Kcat/$K_M$ |
|---|---|---|---|
| Alanine | 0.55 | 21.3 | $2.6 \times 10^4$ |
| Arginine | 0.087 | 167.8 | $5.2 \times 10^2$ |
| Asparagine | 3.6 | 124.5 | $2.9 \times 10^4$ |
| Methionine | 0.54 | 271.8 | $2.0 \times 10^3$ |
| Phenylalanine | 0.47 | 122.8 | $3.8 \times 10^3$ |
| Proline | 0.0014 | 252.0 | $5.7 \times 10^1$ |

Example 7. Inhibition of the Edman Degradation Enzyme by 1-(2-anilino-5-methyl-1,3-thiazol-4-yl)-ethanone Assays were conducted as described above in Example 5, with 5 μM substrate, 100 nM enzyme, and 500 nM-15 μM 1-(2-anilino-5-methyl-1,3-thiazol-4-yl)-ethanone. Reaction velocity was determined as above, plotted against the inverse of inhibitor concentration, and fit by non-linear least squares to determine the inhibition constant.

Example 8. Cloning of Additional N-Terminal Amino Acid Binding Proteins (NAABs)

Primers specific for each NAAB were ordered from Integrated DNA Technologies. Each NAAB was then amplified from isolated, *E. coli* genomic DNA and transferred to a pet42a expression vector at various positions, depending on the gene sequence. These constructs were transformed into either *E. coli* BL21(DE3) or *E. coli* 'Arctic Express' competent cells for expression.

Example 9. Expression and Purification of N-Terminal Amino Acid Binders (NAABs)

Protein was over-expressed following Studier's auto-induction protocol. Bacterial cells were harvested by centrifugation of the cell culture at 5000 rpm and 4° C. for 10 minutes. Cells were then suspended in 1×PBS with 10% glycerol, pH 7.4. Cells were then lysed by sonication (15 seconds at 20% power, 8 times on ice). The cell lysate was centrifuged at 18000 rpm, 4 degrees for 20 minutes. The supernatant was then filtered through a 0.2 um cellulose acetate filter. The filtered lysate was loaded onto a 1 mL GSTrap column and washed with 5 column volumes of binding buffer (1×PBS). Bound protein was then eluted in 50 mM Tris-HCl, 10 mM reduced glutathione. Purified fractions were prepared for SDS-PAGE analysis by mixing 2 parts sample with 1 part 4× loading dye. Samples were analyzed on 16% SDS-PAGE precast gels, and visualized by Coomassie staining. Protein concentration was determined using the calculated molar extinction coefficient and measuring the A280 on an ND-8000 spectrophotometer (Thermo Fisher Scientific).

Example 10. Binding Assays

Real time binding assays between peptides and purified NAABs were performed using biolayer interferometry on a Blitz system (Fortebio, Menlo Park, Calif.). This system monitors interference of light reflected from the surface of a fiber optic sensor to measure the thickness of molecules bound to the sensor surface. Sensors coated with peptides were allowed to bind to the NAABs in 1×PBS at several different protein concentrations. Binding kinetics were calculated using the Blitz software package, which fit the observed binding curves to a 1:1 binding model to calculate the association rate constants. NAABs were allowed to dissociate by incubation of the sensors in 1×PBS. Dissociation curves were fit to a 1:1 model to calculate the dissociation rate constants. Binding affinities were calculated as the kinetic dissociation rate constant divided by the kinetic association rate constant.

TABLE

Measured Affinity Constants

| | |
|---|---|
| Glutamate | 2.12 μM |
| Phenylalanine | 3.44 μM |
| Histidine | 98.7 μM |
| Methionine | 1.07 μM |
| Asparagine | 754 nM |
| Arginine | 129 nM |
| Tryptophan | 48.9 nM |
| Tyrosine | 57.6 μM |
| Phosphoserine | 7.72 μM |
| Phosphotyrosine | 1.07 μM |
| Aspartate | 411 nM |
| Isoleucine | 3.01 μM |
| Leucine | 1.88 μM |
| Glutamine | 531 nM |
| Serine | 938 nM |
| Threonine | 1.01 μM |
| Valine | 1.22 μM |
| Lysine | 2.61 μM |

Figure 8:
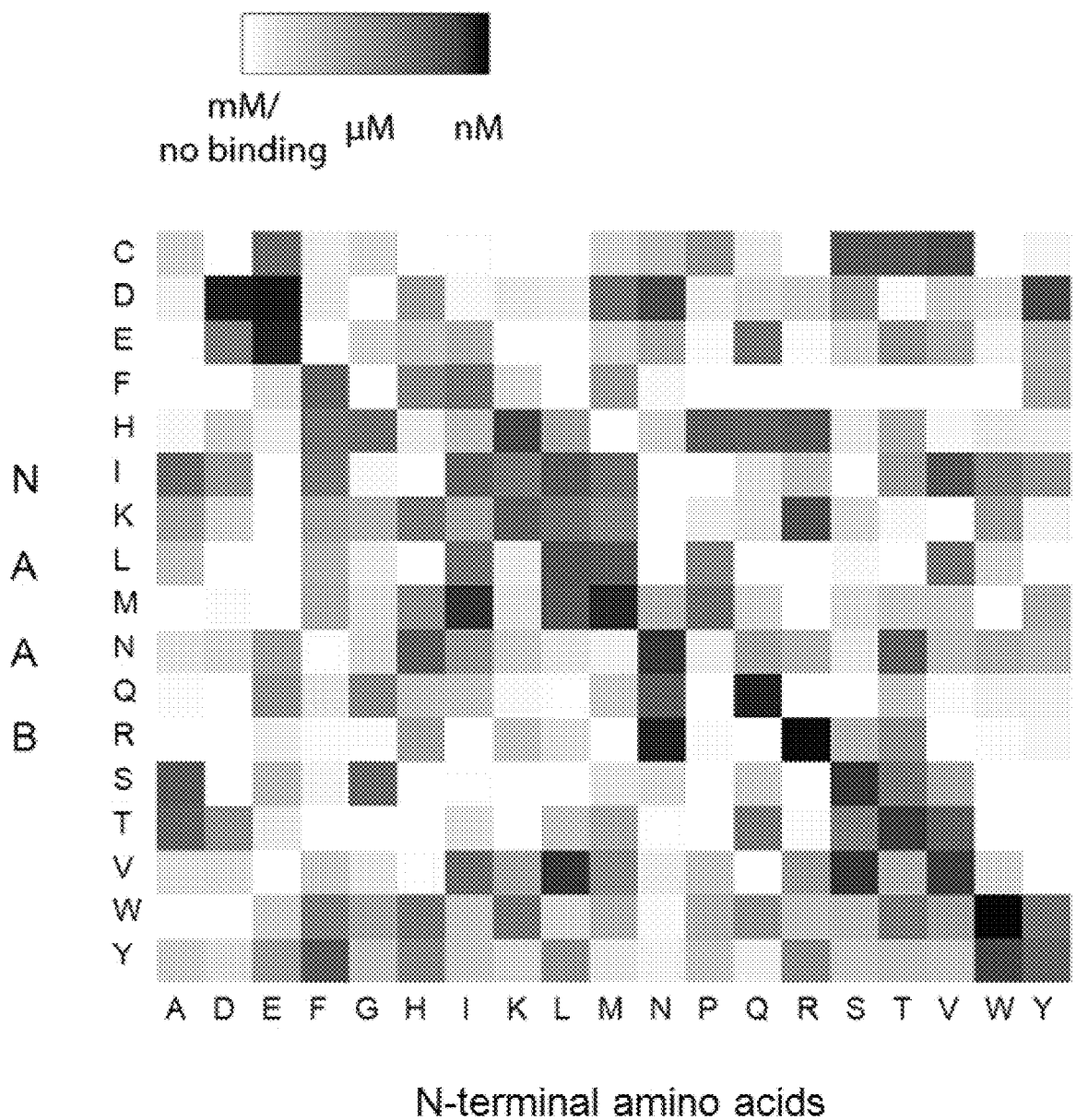
FIG. 8 is a full binding matrix showing the binding affinity of every single NAAB (row) for a single N-terminal amino acid (column) as measured by biolayer interferometry.

FIG. 8 is a full binding matrix that shows how well every engineered NAAB protein binds to every N-terminal amino acid. Each square in the binding matrix represents the binding affinity for a single NAAB with an N-terminal amino acid as measured by biolayer interferometry. Each row in the matrix contains all the binding data for a single NAAB, and each column contains the binding data for a single N-terminal amino acid (shown by single-letter code). Darker squares represent tighter binding. The NAABs exhibit cross-binding for chemically similar N-terminal amino acids. However, the set of predicted binding patterns for each amino acid are distinct. Thus, when taken as a set, the engineered NAAB proteins are capable of identifying amino acids at the N-terminus of peptides.

For reference, the abbreviations of the amino acids areas follows:

| Amino acid | Three letter code | One letter code |
| --- | --- | --- |
| alanine | ala | A |
| arginine | arg | R |
| asparagine | asn | N |
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

TABLE A

NAAB sequences

SEQ ID NO:

SEQ ID NO: 1  wild-type eMAP

MAISIKTPEDIEKMRVAGRLAAEVLEMIEPYVKPGVSTGELD
RICNDYIVNEQHAVSACLGYHGYPKSVCISINEVVCHGIPDD
AKLLKDGDIVNIDVTVIKDGFHGDTSKMFIVGKPTIMGERLC
RITQESLYLALRMVKPGINLREIGAAIQKFVEAEGFSVVREYC
GHGIGRGFHEEPQVLHYDSRETNVVLKPGMTFTIEPMVNAG
KKEIRTMKDGWTVKTKDRSLSAQYEHTIVVTDNGCEILTLR
KDDTIPAIISHDE

SEQ ID NO: 2  eLAP

MAISIKTPEDIEKMRVAGRLAAEVLEMIEPYVKPGVSTGELE
RICWDYIVNEQHATDSLTGHNGIDGHGSISINEVVCHGVPDD
AKLLKDGDIVNIDVTVRKDGFHGDTSKMFIVGKPTIMGERLC
RITQESLYLALRMVKPGINLREIGAAIQKFVEAEGFSVVREYC
GHGIGRGHHEEPQVLHYDSRETNVVLKPGMTFTIEPMVNAG
KKEIRTMKDGSTVKTKDRSLSAQYEHTIVVTDNGCEILTLRK
DDTIPAIISHDE

SEQ ID NO: 3  truncated wild-type MetRS (4-547)

AKKILVTCALPYANGSIHLGHMLEHIQADVWVRYQRMRGH
EVNFICADDAHGTPIMLKAQQLGITPEQMIGEMSQEHQTDFA
GFNISYDNYHSTHSEENRQLSELIYSRLKENGFIKNRTISQLY
DPEKGMFLPDRFVKGTCPKCKSPDQYGDNCEVCGATYSPTE
LIEPKSVVSGATPVMRDSEHFFFDLPSFSEMLQAWTRSGALQ
EQVANKMQEWFESGLQQWDISRDAPYFGFEIPNAPGKYFYV
WLDAPIGYMGSFKNLCDKRGDSVSFDEYWKKDSTAELYHFI
GKDIVYFHSLFWPAMLEGSNFRKPSNLFVHGYVTVNGAKMS
KSRGTFIKASTWLNHFDADSLRYYYTAKLSSRIDDIDLNLED
FVQRVNADIVNKVVNLASRNAGFINKRFDGVLASELADPQL
YKTFTDAAEVIGEAWESREFGKAVREIMALADLANRYVDEQ
APWVVAKQEGRDADLQAICSMGINLFRVLMTYLKPVLPKLT
ERAEAFLNTELTWDGIQQPLLGHKVNPFKALYNRIDMRQVE
ALVEASK

SEQ ID NO: 4  Met NAAB*

AKKILVTCASPYANGSIHLGHMLEHIQADVWVRYQRMRGH
EVNFICADDAHGTPIMLKAQQLGITPEQMIGEMSQEHQTDFA
GFNISYDNYHSTHSEENRQLSELIYSRLKENGFIKNRTISQLY
DPEKGMFLPDRFVKGTCPKCKSPDQYGDNCEVCGATYSPTE
LIEPKSVVSGATPVMRDSEHFFFDLPSFSEMLQAWTRSGALQ
EQVANKMQEWFESGLQQWDISRDAPYFGFEIPNAPGKYFYV
WLDAPIGLMGSFKNLCDKRGDSVSFDEYWKKDSTAELYHFI
GKGIVYFLSLFWPAMLEGSNFRKPSNLFVHGYVTVNGAKMS
KSRGTFIKASTWLNHFDADSLRYYYTAKLSSRIDDIDLNLED
FVQRVNADIVNKVVNLASRNAGFINKRFDGVLASELADPQL
YKTFTDAAEVIGEAWESREFGKAVREIMALADLANRYVDEQ
APWVVAKQEGRDADLQAICSMGINLFRVLMTYLKPVLPKLT

TABLE A-continued

NAAB sequences

| SEQ ID NO: | | |
|---|---|---|
| | | ERAEAFLNTELTWDGIQQPLLGHKVNPFKALYNRIDMRQVE ALVEASK |
| SEQ ID NO: 5 | wild-type MetRS (full length) | MTQVAKKILVTCALPYANGSIHLGHMLEHIQADVWVRYQR MRGHEVNFICADDAHGTPIMLKAQQLGITPEQMIGEMSQEH QTDFAGFNISYDNYHSTHSEENRQLSELIYSRLKENGFIKNRT ISQLYDPEKGMFLPDRFVKGTCPKCKSPDQYGDNCEVCGAT YSPTELIEPKSVVSGATPVMRDSEHFFFDLPSFSEMLQAWTRS GALQEQVANKMQEWFESGLQQWDISRDAPYFGFEIPNAPGK YFYVWLDAPIGYMGSFKNLCDKRGDSVSFDEYWKKDSTAE LYHFIGKDIVYFHSLFWPAMLEGSNFRKPSNLFVHGYVTVN GAKMSKSRGTFIKASTWLNHFDADSLRYYYTAKLSSRIDDID LNLEDFVQRVNADIVNKVVNLASRNAGFINKRFDGVLASEL ADPQLYKTFTDAAEVIGEAWESREFGKAVREIMALADLANR YVDEQAPWVVAKQEGRDADLQAICSMGINLFRVLMTYLKP VLPKLTERAEAFLNTELTWDGIQQPLLGHKVNPFKALYNRID MRQVEALVEASKEEVKAAAAPVTGPLADDPIQETITFDDFA KVDLRVALIENAEFVEGSDKLLRLTLDLGGEKRNVFSGIRSA YPDPQALIGRHTIMVANLAPRKMRFGISEGMVMAAGPGGKD IFLLSPDAGAKPGHQVK |
| SEQ ID NO: 6 | truncated wild-type PheRS (86-350) | VDVSLPGASLFSGGLHPITLMERELVEIFRALGYQAVEGPEV ESEFFNFDALNIPEHHPARDMWDTFWLTGEGFRLEGPLGEEV EGRLLLRTHTSPMQVRYMVAHTPPFRIVVPGRVFRFEQTDAT HEAVFHQLEGLVVGEGIAMAHLKGAIYELAQALFGPDSKVR FQPVYFPFVEPGAQFAVWWPEGGKWLELGGAGMVHPKVFQ AVDAYRERLGLPPAYRGVTGFAFGLGVERLAMLRYGIPDIR YFFGGRLKFLEQFKGVL |
| SEQ ID NO: 7 | PheNAAB (86-350) | VDVSLPGASLFSGGDHPITLMERELVEIFRALGYQAVEGPEV ESEFFNFDALNIPENGPARDMWDTVGKTGEGFRLEGPDGEE VEGRLLLRTHTSPMQVRYMVAHTPPFRIVVPGRVFRAEQTD ATAEAVFHQLEGLVVGEGVNEGDLYGAIYELAQALFGPDSK VRFQPVTFPPFVEPGAQFAVWWPEGGKWLELGGAGMVGPNV FQAVDAYRERLGDPPAYRGVTGFAFGLGVERLAMLRYGIPD IRYF |
| SEQ ID NO: 8 | wild-type PheRS (full length) | MLEEALAAIQNARDLEELKALKARYLGKKGLLTQEMKGLS ALPLEERRKRGQELNAIKAALEAALEAREKALEEAALKEAL ERERVDVSLPGASLFSGGLHPITLMERELVEIFRALGYQAVE GPEVESEFFNFDALNIPEHHPARDMWDTFWLTGEGFRLEGPL GEEVEGRLLLRTHTSPMQVRYMVAHTPPFRIVVPGRVFRFEQ TDATHEAVFHQLEGLVVGEGIAMAHLKGAIYELAQALFGPD SKVRFQPVYFPFVEPGAQFAVWWPEGGKWLELGGAGMVHP KVFQAVDAYRERLGLPPAYRGVTGFAFGLGVERLAMLRYGI PDIRYFFGGRLKFLEQFKGVL |
| SEQ ID NO: 9 | truncated wild-type HisRS (3-180) | NIQAIRGMNDYLPGETAIWQRIEGTLKNVLGSYGYSEIRLPIV EQTPLFKRAIGEVTDVVEKEMYTFEDRNGDSLTLRPEGTAGC VRAGIEHGLLYNQEQRLWYIGPMFRHERPQKGRYRQFHQLG CEVFGLQGPDIDAELIMLTARWWRALGISEHVTLELNSIGSL EARANYRDA |
| SEQ ID NO: 10 | HisNAAB (3-180) | KNIQAIRGMNDYLPGETAIWQRIEGTLKNVLGSYGYSEIRLPI VEQTPLFKRAIGEVTDVVEKEMYTFEDRNGDSLTLRPEGTA GCVRAGIEHGLLYNQEQRLWYIGPMFGNAPQFHQLGCEVFG LQGPDIDAELIMLTARWWRALGISEHVTLELNSIGSLEARAN YRDA |
| SEQ ID NO: 11 | AlaNAAB | SKSTAEIRQAFLDFFHSKGHQVVASSSLVPHNDPTLLFTNAG MNQFKDVFLGLDKRNYSRATTSQRCVRAGGKHNDLENVGY TARHHTFFEMLGNFSFGDYFKHDAIQFAWELLTSEKWF ALPKERLWVTVYESDDEAYEIWEKEVGIPRERIIRIGDNKGA PYASDNFWQMGDTGPCGPCTEIFYDHGDHIWGGPPGSPEED GDRYIEIWNIVFMQFNRQADGTMEPLPKPSVDTGMGL ERIAAVLQHVNSNYDIDL |
| SEQ ID NO: 12 | ArgNAAB | EKQTIVVDYSAPNVAKEMHVGHLRSTIIGDAAVRTLEFLGH KVIRANHVGDWGTQFGMLIAWLEKQQQENAGEMELADLE GFYRDAKKHYDEDEEFAERARNYVVKLQSGDEYFREMWR KLVDITMTQNQITYDRLNVTLTRDDVMGESLYNPMLPGIVA DLKAKGLAVESEGATVVFLDEFKNKEGEPMGVIIQKKDGGY LYTTTDIACAKYRYESLHADRVLYYIDSRQHQLMQAWAIV RKAGYVPESVPLEHHMFGMMLGKDGKPFKTRAGGTVKLAD LLDETLERARRLVAEKNPDMPADELEKLANAVGIGAVKYA |

TABLE A-continued

NAAB sequences

| SEQ ID NO: | | |
|---|---|---|
| | | DLSKNRTTDYIFDWDNMLAFEGNTAPYMQYAYTRVLSVFR KAEINEEQLAAAPVIIREDREAQLAARLLQFEETLTVVAREG TPHVMCAYLYDLAGLFSGFYEHCPILSAENEEVRNSRLKLAQ LTAK TLKLGLDTLGIETVERM |
| SEQ ID NO: 13 | AsnNAAB | SIEYLREVAHLRPRTNLIGAVARVRHTLAQALHRFFNEQGFF WVSTPLITASDTEGAGEMFRVSTLDLE NLPRNDQGKVDFDKDFFGKESFLTVSGQLNGETYACALSKI YTFGPTFRAENSNTSRHLAEFWMLEPEVAFANLNDIAGLAE AMLKYVFKAVLEERADDMKFFAERVDKDAVSRLERFIEADF AQVDYTDAVTILENCGRKFENPVYWGVDLSSEHERYLAEEH FKAPVVVKNYPKDIKAFYMRLNEDGKTVAAMDVLAPGIGEI IGGSQREERLDVLDERMLEMGLNKEDYWWYRDLRRYGTVP HSGFGLGFERLIAYVTGVQNVRDVIPFPRTP |
| SEQ ID NO: 14 | AspNAAB | LPLDSNHVNTEEARLKYRYLDLRRPEMAQRLKTRAKITSLV RRFMDDHGFLDIETPMLTKATPEGARDYLVPSRVHKGKFYA LPQSPQLFKQLLMMSGFDRYYQIVKCFRDEDLRADRQPEFT QIDVETSFMTAPQVREVMEALVRHLWLEVKGVDLGDFPVM TFAEAERRYGSDKPDLRNPMELTDVADLLRSVEFAVFAGPA NDPKGRVAALRVPGGASLTRKQIDEYDNFVKIYGAKGLAYI KVNERAKGLEGINSPVAKFLNAEHEAILDRTAAQDGDMIFFG ADNKKIVADAMGALRLKVGKDLGLTDESKWAPLWVIDFPM FEDDGEGGLTAMHHPFTSPKDMTAAELKAAPENAVANAYD MVINGYEVGGGSVRIHNGDMQQTVFGILGINEEEQREKFGFL LDALKYGTPPHAGLAFGLDRLTMLLTGTDNIRDVIAFPK |
| SEQ ID NO: 15 | CysNAAB | MLKIFNTLTRQKEEFKPIHAGEVGMYVCGITVYDLCHIGHGR TFVAFDVVARYLRFLGYKLKYVRNITDI DDKIIKRANENGESFVAMVDRMIAEMHKDFDALNILRPDME PRATHHIAEIIELTEQLIAKGHAYVADNGDVMFDVPTDPTYG VLSRQDLDQLQAGARVDVVDDKRNPMDFVLWKMSKEGEP SWPSPWGAGRPGWHIECSAMNCKQLGNHFDIHGGGSDLMF PHHENEIAQSTCAHDGQYVNYWMHSGMVMVDREKMSKSL GNFFTVRDVLKYYDAETVRYFLMSGHYRSQLNY |
| SEQ ID NO: 16 | GlnNAAB | TNFIRQIIDEDLASGKHTTVHTRFPPEPNGYLHIGHAKSICLNF GIAQDYKGQCNLRFDDTNPVKEDIEYVESIKNDVEWLGFHW SGNVRYSSDYFDQLHAYAIELINKGLAYVDELTPEQIREYRG TLTQPGKNSPYRDRSVEENLALFEKMRTGGFEEGKACLRAKI DMASPFIVMRDPVLYRIKFAEHHQTGNKWCIYPMYDFTHCIS DALEGITHSLCTLEFQDNRRLYDWVLDNITIPVHPRQYEFSR |
| SEQ ID NO: 17 | GluNAAB | IKTRFAPSPTGYLHVGGARTALYSWLFARNHGGEFVLRIEDT DLERSTPEAIEAIMDGMNWLSLEWDEGPYYQTKRFDRYNAV IDQMLEEGTAYKCYCSKERLEALREEQMAKGEKPRYDGRC RHSHEHHADDEPCVVRFANPQEGSVVFDDQIRGPIEFSNQEL DDLIIRRTDGSPTYNFCVVVDDWDMEITHVIRGEDHINNTPR QINILKALNAPVPVYAHVSMINGDDGKKLSKRHGAVSVMQ YRDDGYLPEALLNYLVRLGWSHGDQEIFTREEMIKYFTLNA VSKSASAFNTDKLLWLNHHYI |
| SEQ ID NO: 18 | IleNAAB | FPMRGDLAKREPGMLARWTDDDLYGIIRAAKKGKKTFILHD GPPYANGSIHIGHSVNKILKDIIIKSKGLSGYDSPYVPGWDCH GLPIELKVEQEYGKPGEKFTAAEFRAKCREYAATQVDGQRK DFIRLGVLGDWSHPYLTMDFKTEANIIRALGKIIGNGHLHKG AKPVHWCVDCRSALAEAEVEYYDKTSPSIVAFQAVDQDAL KTKFGVSNVNGPISLVIWTTTPWTLPANRAISIAPDFDYALVQ IDGQAVILAKDLVESMQRIGVSDYTILGTVKGAELELLRFTH PFMDFDVPAILGDHVTLDAGTGAVHTAPGHGPDDYVIGQKY GLETANPVGPDGTYLPGTYPTLDGVNVFKANDIVVALLQEK GALLHVEKMQHSYPCCWRHKTPIIFRATPQWFVSMDQKGLR AQSLKEIKGVQWIPDWGQARIESMVANRPDWCISRQRTWG VPMSLFVHKDTEELHPRTLELMEEVAKRVEVDGIQAWWDL DAKEILGDEADQYVKVPDTLDVWFDSGSTHSSVVDVRPEFA GHAADMYLEGSDQHRGWFMSSLMISTAMKGKAPYRQVLT HGFTVDGQGRKMSKSIGNTVSPQDVMNKLGADILRLWVAS TDYTGEMAVSDEILKRAADSYRRIRNTARFLLANLNGFDPA KDMVKPEEMVVLDRWAVGCAKAAQEDILKAYEAYDFHEV VQRLMRFCSVEMGSFYLDIIKDRQYTAKADSVARRSCQTAL YHIAEALVRWMAPILSFTADEVWGYLPGERE |
| SEQ ID NO: 19 | LeuNAAB | IESKVQLHWDEKRTFEVTEDESKEKYYCLSMLPYPSGRLHM GHVRNYTIGDVIARYQRMLGKNVLQPIGWDAFGLPAEGAA VKNNTAPAPWTYDNIAYMKNQLKMLGFGYDWSRELATCTP |

TABLE A-continued

NAAB sequences

| SEQ ID NO: | | |
|---|---|---|
| | | EYYRWEQKCFTELYKKGLVYKKTSAVNWCPNDQTVLANE QVIDGCCWRCDTKVERKEIPQWFIKITAYADELLNDLDKLD HWPDTVKTMQRNWIGRSEGVEITFNVKDYDNTLTVYTTRPD TFMGCTYLAVAAGHPLAQKAAENNPELAAFIDECRNTKVAE AEMATMEKKGVDTGFKAVHPLTGEEIPVWAANFVLMEYGT GAVMAVPGHDQRDYEFASKYGLNIKPVILAADGSEPDLSQQ ALTEKGVLFNSGEFNGLDHEAAFNAIADKLTEMGVGERKVN YRLRDWGVSRQRYWGAPIPMVTLEDGTVMPTPDDQLPVILP EDVVMDGITSPIKADPEWAKTTVNGMPALRETDTFDTFMES SWYYARYTCPEYKEGMLDSKAANYWLPVDIYIGGIEHAIMH LLYFRFFHKLMRDAGMVNSDEPAKQLLCQGMVLADAFYYV GENGERNWVSPVDAIVERDEKGRIVKAKDAAGHELVYTGM SKMSKSKNNGIDPQVMVERYGADTVRLFMMFASPADMTLE WQESGVEGANRFLKRVWKLVYEHTAKGDVAALNVDALTE DQKALRRDVHKTIAKVTDDIGRRQTFNTAIAAIMELMNKLA KAPTDGEQDRALMQEALLAVVRMLNPFTPHICFTLWQELKG EGDIDNAPWP |
| SEQ ID NO: 20 | LysNAAB | ANDKSRQTFVVRSKILAAIRQFMVARGFMEVETPMMQVIPG GASARPFITHHNALDLDMYLRIAPELYLKRLVVGGFERVFEI NRNFRNEGISVRHNPEFTMMELYMAYADYHDLIELTESLFRT LAQEVLGTTKVTYGEHVFDFGKPFEKLTMREAIKKYRPETD MADLDNFDAAKALAESIGITVEKSWGLGRIVTEIFDEVAEAH LIQPTFITEYPAEVSPLARRNDVNPEITDRFEFFIGGREIGNGFS ELNDAEDQAERFQEQVNAKAAGDDEAMFYDEDYVTALEY GLPPTAGLGIGIDRMIMLFTNSHTIRDVILFPAMRP |
| SEQ ID NO: 21 | ProNAAB | MIRKLASGLYTWLPTGVRVLKKVENIVREEMNNAGAIEVLM PVVQPSELWQESGRWEQYGPELLRIADRGDRPFVLGPTHEE VITDLIRNELSSYKQLPLNFYQIQTKFRDEVRPRFGVMRSREF LMKDAYSFHTSQESLQETYDAMYAAYSKIFSRMGLDFRAVQ ADTGSIGGSASHEFQVLAQSGEDDVVFSDTSDYAANIELAEA IAPKEPRAAATQEMTLVDTPNAKTIAELVEQFNLPIEKTVKTL LVKAVEGSSFPPLVALLVRGDHELNEVKAEKLPQVASPLTFAT EEEIRAVVKAGPGSLGPVNMPIPVVIDRTVAAMSDFAAGANI DGKHYFGINWDRDVATPEIADIRNVVAGDPSPDGQGTLLIKR GIEVGHIFQLG |
| SEQ ID NO: 22 | SerNAAB | MLDPNLLRNEPDAVAEKLARRGFKLDVDKLGALEERRKVL QVKTENLQAERNSRSKSIGQAKARGEDIEPLRLEVNKLGEEL DAAKAELDALQAEIRDIALTIPNLPADEVPVGKDENDNVEVS RWGTPREFDFEVRDHVTLGEMYSGLDFAAAVKLTGSRFVV MKGQIARMHRALSQFMLDLHTEQHGYSENYVPYLVNQDTL YGTGQLPKFAGDLFHTRPLEEEADTSNYALIPTAEVPLTNLV RGEIIDEDDLPIKMTAHTPCFRSEAGSYGRDTRGLIRMHQFD KVEMVQIVRPEDSMAALEEMTGHAEKVLQLLGLPYRKIILC TGDMGFGACKTYDLEVWIPAQNTYREISSCSNVWDFQARR MQARCRSKSDKKTRLVHTLNGSGLAVGRTLVAVMENYQQ ADGRIEVPEVLRPYMNGLEYI |
| SEQ ID NO: 23 | ThreNAAB | RDHRKIGKQLDLYHMQEEAPGMVFWHNDGWTIFRELEVFV RSKLKEYQYQEVKGPFMMDRVLWEKTGHWDNYKDAMFTT SSENREYCIKPMNCPGHVQIFNQGLKSYRDLPLRMAEFGSCH RNEPSGSLHGLGRVRGFTQDDAHIFCTEEQIRDEVNGCIRLV YDMYSTFGFEKIVVKLSTRPEKRIGSDEMWDRAEADLAVAL EENNIPFEYQLGEGAFYGPKIEFTLYDCLDRAAQCGTVQLDF SLPSRLSASYVGEDNERKVPVMIHRAILGSMEVFIGILTEEFA GFFPTWLAPVQVVIMNITDSQSEYVNELTQKLSNAGIRVKAD LRNEKIGFKIREHTLRRVPYMLVCGDKEVESGKVAVRTRRG KDLGSMDVNEVIEKLQQEIRSRSLKQLEE |
| SEQ ID NO: 24 | TrpNAAB | MTKPIVFSGAQPSGELTIGNYMGALRQWINMQDDYHCIYCI VDQHAITVRQDAQKLRKATLDTLALYLACGIDPEKSTIFVQS HVPEHAQLGWALNCYTYFGELSRMTQFKDKSARYAENINA GLFDYPVLMAADILLYQTNLVPVGEDQKQHLELSRDIAQRF NALYGDIFKVPEPFIPKSGARVMSLLEPTKKMSKSDDNRNNV IGLLEDPKSVVKKIKRAVTDSDEPPVVRYDVQNKAGVSNLL DILSAVTGQSIPELEKQ |
| SEQ ID NO: 25 | TyrNAAB | MASSNLIKQLQERGLVAQVTDEEALVERLAQGGPIALYCGFDP TADSLHLGHLVPLLCLKRFQQAGHKPVALVGGATGLIGDPS FKAAERKLNTEETVQEWVDKIRKQVAPFLDFDCGENSAIAA NNYDWFGNMNVLTFLRDIGKHFSVNQMINKEAVKQRLNRE DQGISFTEFSYNLLQGYDFACLNKQYGVVLQIGGSDQWGNI TSGIDLTRRLHQNVFGLTVPLITKADGTKFGKTEGGAVWL |

TABLE A-continued

NAAB sequences

| SEQ ID NO: | | |
|---|---|---|
| | | DPKKTSPYKFYQFWINTADADVYRFLKFFTFMSIEEINALEEE DKNSGKAPRAQYVLAEQVTRLVHGEEGLQAAKRITECLFSG SLSALSEADFEQLAQDGVPMVKMEKGADLMQALVDSELQP SRGQARKTIASNAITINGEKQSDPEYFFKEEDRLFGRFTLLRR GKKNYCLICWK |
| SEQ ID NO: 26 | ValNAAB | MEKTYNPQDIEQPLYEHWEKQGYFKPNGDESQESFCIMIPPP NVTGSLHMGHAFQQTIMDTMIRYQRMQGKNTLWQVGTDH AGIATQMVVERKIAAEEGKTRHDYGREAFIDKIWEWKAESG GTITRQMRRLGNSVDWERERFTMDEGLSNAVKEVFVRLYK EDLIYRGKRLVNWDPKLRTAISDLEVENRESKGSMWHIRYP LADGAKTADGKDYLVVATTRPETLLGDTGVAVNPEDPRYK DLIGKYVILPLVNRRIPIVGDEHADMEKGTGCVKITPAHDFN DYEVGKRHALPMINILTFDGDIRESAQVFDTKGNESDVYSSEI PAEFQKLERFAARKAVVAAIDALGLLEEIKPHDLTVPYGDRG GVVIEPMLTDQWYVRADVLAKPAVEAVENGDIQFVPKQYE NMYFSWMRDIQDWCISRQLWWGHRIPAWYDEAGNVYVGR NEEEVRKENNLGADVALRQDEDVLDTWFSSALWTFSTLGW PENTDALRQFHPTSVMVSGFDIIFFWIARMIMMTMHFIKDEN GKPQVPFHTVYMTGLIRDDEGQKMSKSKGNVIDPLDMVDGI SLPELLEKRTGNMMQPQLADKIRKRTEKQFPNGIEPHGTDAL RFTLAALASTGRDINWDMKRLEGYRNFCNKLWNASRFVLM NTEGQDCGFNGGEMTLSLADRWILAEFNQTIKAYREALDSF RFDIAAGILYEFTWNQFCDWYLELTKPVMNGGTEAELRGTR HTLVTVLEGLLRLAHPIIPFITETIWQ |
| SEQ ID NO: 27 | Phospho-tyrosine NAAB** | MDEFEMIKRNTSEIISELREVLKKDEKSALIGFEPSGKIHLGH YLQKKMIDLQNAGFDIIIPLADLHAYLNQKGELDEIRKIGDY NKKVFEAMLKAKYVYGSEFQLDKYTLNVYRLALKTTLKAR RSMELIAREDENPVAEVIYPIMQVNGCHYKGVDVAVGGME QRKIMLARELLPKKVVCIHPVLTGLDGEGKMSSSGNFIAVDD SPEEIRAFKKAYCPAGVVEGNPEIAKYFLEYPLTIKPEKFGGD LTVNSYEESLFKNKELHPMDLKAVAEELIKILEPIRK |
| SEQ ID NO: 28 | Phospho-serine NAAB | MRFDPEKIKKDAKENFDLTWNEGKKMVKTPTLNERYPRTTF RYGKAHPVYDTIQKLREAYLRMGFEEMMNPLIVDEKEVHK QFGSEALAVLDRCFYLAGLPRPNVGISDERIAQINGILGDIGD EGIDKVRKVLHAYKKGKVEGDDLVPEISAALEVSDALVAD MIEKVFPEFKELVAQASTKTLRSHMTSGWFISLGALLERKEP PFHFFSIDRCFRREQQEDASRLMTYYSASCVIMDENVTVDHG KAVAEGLLSQFGFEKFLFRPDEKRSKYYVPDTQTEVFAFHPK LVGSNSKYSDGWIEIATFGIYSPTALAEYDIPCPVMNLGLGVE RLAMILHDAPDIRSLTYPQIPQYSEWEMSDSELAKQVFVDKT PETPEGREIADAVVAQCELHGEEPSPCEFPAWEGEVCGRKVK VSVIEPEENTKLCGPAAFNEVVTYQGDILGIPNTKKWQKAFE NHSAMAGIRFIEAFAAQAAREIEEAAMSGADEHIVRVRIVKV PSEVNIKIGATAQRYITGKNKKIDMRGPIFTSAKAEFE |

*Utilizes base truncation mutant reported in reference (3) with an additional mutation of our own design.
**Truncated version of sulfotyrosine tRNA synthetase mutant from (2). The full length mutant is under patent - U.S. Pat. No. 8,114,652 B2.

TABLE B

Edmanase Sequence

| SEQ ID NO: 29 | APAAVDWRARGAVTAVKDSGQCGSGWAFAAIGNVECQWFLAGHPL TNLSEQMLVSCDKTDSGCSSGLMDNAFEWIVQENNGAVYTEDSYPY ASATGISPPCTTSGHTVGATITGHVELPQDEAQIAAWLAVNGPVAVCV DASSWMTYTGGVMTSCVSESYDHGVLLVGYNDSHKVPYWIIKNSWT TQWGEEGYIRIAKGSNQCLVKEEASSAVVG |
|---|---|

REFERENCES

1. Ingolia N T, Ghaemmaghami S, Newman J R S, Weissman J S. *Genome-wide analysis in vivo of translation with nucleotide resolution using ribosome profiling*. Science, 2009, 324: 218.
2. Grimsrud P A, Swaney D L, Wenger C D, Beauchene N A, Coon J J. *Phosphoproteomics for the masses*. ACS Chem Biol. 2010, 5: 105-119.
3. Duncan M W, Aebersold R, Caprioli R M. *The pros and cons of peptide-centric proteomics*. Nat Biotechnol. 2010.
4. Gillette M A, Mani D R, Carr S A. *Place of Pattern in Proteomic Biomarker Discovery*. J Proteome Res. 2005, 4: 1143-1154.
5. Anderson N L, Anderson N G. *The human plasma proteome: history, character, and diagnostic prospects*. Mol Cell Proteomics. 2002

6. Edman P. *Method for determination of the amino acid sequence in peptides.* Acta Chem Scand. 1950, 4:283-293.
7. Mitra R D, Tessler L A. *Single Molecule Protein Screening.* WO 2010/065531 A1.
8. Tessler L A, Donahoe C D, Garcia D J, Jun Y S, Elbert D L, Mitra R D. *Nanogel surface coatings for improved single-molecule imaging substrates.* J R Soc Interface. 2011
9. Tessler L A, Reifenberger J G, Mitra R D. *Protein Quantification in Complex Mixtures by Solid Phase Single-Molecule Counting.* Anal Chem. 2009, 81: 7141-7148.
10. Emmert-Buck M R, Bonner R F, Smith P D, Chuaqui R F, Zhuang Z, Goldstein S R, Weiss R A, Liotta L A. *Laser capture microdissection.* Science. 1996, 274: 998.
11. Havranek J J, Harbury P B. *Automated design of specificity in molecular recognition.* Nat Struct Biol. 2003, 10: 45-52.
12. Ashworth J, Havranek J J, Duarte C M, Sussman D, R. J. Monnat J, Stoddard B L, Baker D. *Computational redesign of endonuclease DNA binding and cleavage specificity.* Nature. 2006
13. Ashworth J, Taylor G K, Havranek J J, Quadri S A, Stoddard B L, Baker D. *Computational reprogramming of homing endonuclease specificity at multiple adjacent base pairs.* Nucleic Acids Res. 2010, 38: 5601.
14. Havranek J J, Baker D. *Motif-directed flexible backbone design of functional interactions.* Protein Sci. 2009, 18: 1293-1305.
15. Berman H, Henrick K, Nakamura H, Markley J L. *The worldwide Protein Data Bank (wwPDB): ensuring a single, uniform archive of PDB data.* Nucleic Acids Res. 2o06, 35: D301.
16. Schmitt E, Tanrikulu I C, Yoo T H, Panvert M, Tirrell D A, Mechulam Y. *Switching from an induced-fit to a lock-and-key mechanism in an aminoacyl-tRNA synthetase with modified specificity.* J Mol Biol. 2009, 394: 843-851.
17. Studier F W. *Protein production by auto-induction in high-density shaking cultures.* Protein Expr Purif 2005, 41: 207-234.
18. Wolf Y I, Aravind L, Grishin N V, Koonin E V. *Evolution of aminoacyl-tRNA synthetases-analysis of unique domain architectures and phylogenetic trees reveals a complex history of horizontal gene transfer events.* Genome Res. 1999, 9: 689.
19. Finn R D, Tate J, Mistry J, Coggill P C, Sammut S J, Hotz H R, Ceric G, Forslund K, Eddy S R, Sonnhammer E L, Bateman A. *The Pfam protein families database.* Nucleic Acids Res. 2008, 36: D281-8.
20. Augustine J, Francklyn C. *Design of an active fragment of a class II aminoacyl-tRNA synthetase and its significance for synthetase evolution.* Biochemistry. 1997, 36: 3473-3482.
21. Arnez J G, Augustine J G, Moras D, Francklyn C S. *The first step of aminoacylation at the atomic level in histidyl-tRNA synthetase.* Proc Natl Acad Sci USA. 1997, 94: 7144.
22. Holm L, Rosenstrom P. *Dali server: conservation mapping in 3D.* Nucleic Acids Res. 2010, 38: W545
23. Kavran J M, Gundllapalli S, O'donoghue P, Englert M, Soll D, Steitz T A. *Structure of pyrrolysyl-tRNA synthetase, an archaeal enzyme for genetic code innovation.* Proc Natl Acad Sci USA. 2007, 104: 11268.
24. Kuhlman B, Baker D. *Native protein sequences are close to optimal for their structures.* Proc Natl Acad Sci US A. 2000; 97:10383-10388.
25. Barrett G C, Penglis A J. *Edman Stepwise degradation of polypeptides: a new strategy employing mild basic cleavage conditions.* Tetrahedron Lett. 1985, 26: 4375-4378.
26. Celej M S, Montich G G, Fidelia G D. *Protein stability induced by ligand binding correlates with changes in protein flexibility.* Protein Sci. 2003, 12: 1496-1506.
27. Choe Y, Brinen L S, Price M S, Engel J C, Lange M, Grisostomi C, Weston S G, Pallai P V, Cheng H, Hardy L W. *Development of α-keto-based inhibitors of cruzain, a cysteine protease implicated in Chagas disease.* Bioorg Med Chem. 2005, 13: 2141-2156.
28. Carter P, Wells J A. *Engineering enzyme specificity by "substrate-assisted catalysis".* Science. 1987, 237: 394.
29. McGrath M E. *The lysosomal cysteine proteases.* Annu Rev Biophys Biomol Struct. 1999, 28: 181-204.
30. Jiang L, Althoff E A, Clemente F R, Doyle L, Rothlisberger D, Zanghellini A, Gallaher J L, Betker J L, Tanaka F, Barbas C F 3rd, Hilvert D, Houk H N, Stoddard B L, Baker D. *De novo computational design of retro-aldol enzymes.* Science. 2008, 319: 1387-1391.
31. Rothlisberger D, Khersonsky O, Wollacott A M, Jiang L, DeChancie J, Betker J, Gallaher J L, Althoff E A, Zanghellini A, Dym O, Albeck S, Houk K N, Tawfik D S, Baker D. *Kemp elimination catalysts by computational enzyme design.* Nature. 2008, 453: 190-195.
32. Schmidt M W, Baldridge K K, Boatz J A, Elbert S T, Gordon M S, Jensen J H, Koseki S, Matsunaga N, Nguyen K A, Su S. *General atomic and molecular electronic structure system.* J Comput Chem. 1993, 14: 1347-1363.
33. Dantas G, Corrent C, Reichow S L, Havranek J J, Eletr Z M, Isern N G, Kuhlman B, Varani G, Merritt E A, Baker D. *High-resolution structural and thermodynamic analysis of extreme stabilization of human procarboxypeptidase by computational protein design.* J Mol Biol. 2007, 366: 1209-1221.
34. Dunbrack R L. *Backbone-dependent rotamer library for proteins application to side-chain prediction.* J Mol Biol. 1993, 230: 543-574.
35. Chiravuri M, Agarraberes F, Mathieu S L, Lee H, Huber B T. *Vesicular localization and characterization of a novel post-proline-cleaving aminodipeptidase, quiescent cell proline dipeptidase.* J Immunol. 2000, 165: 5695.
36. Fukunaga R, Yokoyama S. *Structural insights into the first step of RNA-dependent cysteine biosynthesis in archaea.* Nat Struct Mol Biol. 2007, 14: 272-279.
37. Liu C C, Schultz P G. *Recombinant expression of selectively sulfated proteins in Escherichia coli.* Nat Biotechnol. 2006, 24: 1436-1440.
38. Turner J M, Graziano J, Spraggon G, Schultz P G. *Structural characterization of a p-acetylphenylalanyl aminoacyl-tRNA synthetase.* J Am Chem Soc. 2005, 127: 14976-14977.
39. Xie J, Supekova L, Schultz P G. *A genetically encoded metabolically stable analogue of phosphotyrosine in Escherichia coli.* ACS Chem Biol. 2007, 2: 474-478.
40. O'Brien P J, Herschlag D. *Catalytic promiscuity and the evolution of new enzymatic activities.* Chem Biol. 1999, 6: R91-R105.

What is claimed is:

1. A method for identifying a N-terminal amino acid of a polypeptide, the method comprising:
   (a) contacting the polypeptide with one or more fluorescently labeled N-terminal amino acid binding proteins (NAABs);
   (b) detecting fluorescence of the NAAB that is bound to the N-terminal amino acid of the polypeptide;
   (c) identifying the N-terminal amino acid of the polypeptide based on the detected fluorescence; and
   (d) cleaving the identified N-terminal amino acid of the polypeptide.

2. The method of claim 1, wherein the cleaving of step (d) is performed using a protease.

3. The method of claim 2, wherein the protease comprises an isolated, synthetic, or recombinant Edman degradation enzyme.

4. The method of claim 1, wherein the cleavage in step (d) catalyzes the cleavage in an aqueous buffer and at a neutral pH.

5. The method of claim 1, wherein the cleavage in step (d) does not employ an acidic condition and elevated temperature.

6. The method of claim 2, wherein the protease allows for promiscuous cleavage of diverse N-terminal amino acids.

7. The method of claim 3, wherein the Edman degradation enzyme cleaves the N-terminal amino acid by nucleophilic attack of the thiourea sulfur atom on the carbonyl group of the scissile peptide bond.

8. The method of claim 3, wherein the Edman degradation enzyme is configured for substrate assisted catalysis.

9. The method of claim 1, wherein the cleavage in step (d) comprises treating the polypeptide with two or more enzymes.

10. The method of claim 9, wherein the two or more enzymes comprise an enzyme for removal of proline from a polypeptide.

11. The method of claim 1, wherein step (d) cleaves a modified N-terminal amino acid from the polypeptide.

12. The method of claim 1, wherein the NAAB binds to an N-terminal amino acid with a post translational-modification.

13. The method of claim 12, wherein N-terminal amino acid with the post translational-modification comprises a phosphorylated N-terminal amino acid.

14. The method of claim 1, wherein a single NAAB is configured to identify multiple amino acids.

15. The method of claim 1, which comprises simultaneously sequencing a plurality of polypeptides.

16. The method of claim 1, which further comprises immobilizing the polypeptide or polypeptides on a substrate prior to the contacting in step (a).

17. The method of claim 1, wherein the contacting in step (a) comprises contacting the polypeptide with a single type of NAAB that selectively binds to a single type of N-terminal amino acid residue.

18. The method of claim 1, wherein the contacting in step (a) comprises contacting the polypeptide with a first type of NAAB and a second type of NAAB, wherein the first type of NAAB selectively binds to a first type of N-terminal amino acid residue and the second type of NAAB selectively binds to a second type of N-terminal amino acid residue different from the first type of N-terminal amino acid residue.

19. The method of claim 18, wherein the first type of NAAB is coupled to a first fluorophore and the second type of NAAB is coupled to a second fluorophore, wherein the first and second fluorophores have different fluorescence emission spectra.

20. The method of claim 1, wherein a plurality of NAABs are introduced in a step-wise fashion.

21. The method of claim 1, wherein the polypeptide is contacted with a mixture of two or more types of NAABs that each selectively binds to different amino acid residues.

22. The method of claim 1, further comprising removing the NAAB from the polypeptide by contacting the polypeptide with a wash buffer that causes dissociation of the NAAB bound to the N-terminal amino acid of the polypeptide.

23. The method of claim 1, wherein steps (a) through (d) are repeated until the polypeptide or a fragment thereof is sequenced.

* * * * *

SEQUENCE LISTING

<160> NUMBER OF SEQ ID NOS: 30

<210> SEQ ID NO 1
<211> LENGTH: 264
<212> TYPE: PRT
<213> ORGANISM: Escherichia coli

<400> SEQUENCE: 1

Met Ala Ile Ser Ile Lys Thr Pro Glu Asp Ile Glu Lys Met Arg Val
1               5                   10                  15

Ala Gly Arg Leu Ala Ala Glu Val Leu Glu Met Ile Glu Pro Tyr Val
                20                  25                  30

Lys Pro Gly Val Ser Thr Gly Glu Leu Asp Arg Ile Cys Asn Asp Tyr
                35                  40                  45

Ile Val Asn Glu Gln His Ala Val Ser Ala Cys Leu Gly Tyr His Gly
        50                  55                  60

Tyr Pro Lys Ser Val Cys Ile Ser Ile Asn Glu Val Val Cys His Gly
65                  70                  75                  80

Ile Pro Asp Asp Ala Lys Leu Leu Lys Asp Gly Asp Ile Val Asn Ile
                85                  90                  95

Asp Val Thr Val Ile Lys Asp Gly Phe His Gly Asp Thr Ser Lys Met
                100                 105                 110

Phe Ile Val Gly Lys Pro Thr Ile Met Gly Glu Arg Leu Cys Arg Ile
            115                 120                 125

Thr Gln Glu Ser Leu Tyr Leu Ala Leu Arg Met Val Lys Pro Gly Ile
    130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

Phe His Glu Glu Pro Gln Val Leu His Tyr Asp Ser Arg Glu Thr Asn
                180                 185                 190

Val Val Leu Lys Pro Gly Met Thr Phe Thr Ile Glu Pro Met Val Asn
            195                 200                 205

Ala Gly Lys Lys Glu Ile Arg Thr Met Lys Asp Gly Trp Thr Val Lys
    210                 215                 220

Thr Lys Asp Arg Ser Leu Ser Ala Gln Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260

<210> SEQ ID NO 2
<211> LENGTH: 264
<212> TYPE: PRT
<213> ORGANISM: Escherichia coli

<400> SEQUENCE: 2

Met Ala Ile Ser Ile Lys Thr Pro Glu Asp Ile Glu Lys Met Arg Val
1               5                   10                  15

Ala Gly Arg Leu Ala Ala Glu Val Leu Glu Met Ile Glu Pro Tyr Val
                20                  25                  30

Lys Pro Gly Val Ser Thr Gly Glu Leu Glu Arg Ile Cys Trp Asp Tyr
                35                  40                  45

Ile Val Asn Glu Gln His Ala Thr Asp Ser Leu Thr Gly His Asn Gly

```
            50                  55                  60
Ile Asp Gly His Gly Ser Ile Ser Ile Asn Glu Val Cys His Gly
 65                  70                  75                  80

Val Pro Asp Asp Ala Lys Leu Leu Lys Asp Gly Asp Ile Val Asn Ile
                 85                  90                  95

Asp Val Thr Val Arg Lys Asp Gly Phe His Gly Asp Thr Ser Lys Met
            100                 105                 110

Phe Ile Val Gly Lys Pro Thr Ile Met Gly Glu Arg Leu Cys Arg Ile
                115                 120                 125

Thr Gln Glu Ser Leu Tyr Leu Ala Leu Arg Met Val Lys Pro Gly Ile
            130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

His His Glu Glu Pro Gln Val Leu His Tyr Asp Ser Arg Glu Thr Asn
            180                 185                 190

Val Val Leu Lys Pro Gly Met Thr Phe Thr Ile Glu Pro Met Val Asn
                195                 200                 205

Ala Gly Lys Lys Glu Ile Arg Thr Met Lys Asp Gly Ser Thr Val Lys
            210                 215                 220

Thr Lys Asp Arg Ser Leu Ser Ala Gln Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260

<210> SEQ ID NO 3
<211> LENGTH: 544
<212> TYPE: PRT
<213> ORGANISM: Escherichia coli

<400> SEQUENCE: 3

Ala Lys Lys Ile Leu Val Thr Cys Ala Leu Pro Tyr Ala Asn Gly Ser
 1                   5                  10                  15

Ile His Leu Gly His Met Leu Glu His Ile Gln Ala Asp Val Trp Val
                20                  25                  30

Arg Tyr Gln Arg Met Arg Gly His Glu Val Asn Phe Ile Cys Ala Asp
             35                  40                  45

Asp Ala His Gly Thr Pro Ile Met Leu Lys Ala Gln Gln Leu Gly Ile
 50                  55                  60

Thr Pro Glu Gln Met Ile Gly Glu Met Ser Gln Glu His Gln Thr Asp
 65                  70                  75                  80

Phe Ala Gly Phe Asn Ile Ser Tyr Asp Asn Tyr His Ser Thr His Ser
                 85                  90                  95

Glu Glu Asn Arg Gln Leu Ser Glu Leu Ile Tyr Ser Arg Leu Lys Glu
            100                 105                 110

Asn Gly Phe Ile Lys Asn Arg Thr Ile Ser Gln Leu Tyr Asp Pro Glu
            115                 120                 125

Lys Gly Met Phe Leu Pro Asp Arg Phe Val Lys Gly Thr Cys Pro Lys
            130                 135                 140

Cys Lys Ser Pro Asp Gln Tyr Gly Asp Asn Cys Glu Val Cys Gly Ala
145                 150                 155                 160
```

Thr Tyr Ser Pro Thr Glu Leu Ile Glu Pro Lys Ser Val Val Ser Gly
                    165                 170                 175

Ala Thr Pro Val Met Arg Asp Ser Glu His Phe Phe Asp Leu Pro
                180                 185                 190

Ser Phe Ser Glu Met Leu Gln Ala Trp Thr Arg Ser Gly Ala Leu Gln
        195                 200                 205

Glu Gln Val Ala Asn Lys Met Gln Glu Trp Phe Glu Ser Gly Leu Gln
        210                 215                 220

Gln Trp Asp Ile Ser Arg Asp Ala Pro Tyr Phe Gly Phe Glu Ile Pro
225                 230                 235                 240

Asn Ala Pro Gly Lys Tyr Phe Tyr Val Trp Leu Asp Ala Pro Ile Gly
                245                 250                 255

Tyr Met Gly Ser Phe Lys Asn Leu Cys Asp Lys Arg Gly Asp Ser Val
                260                 265                 270

Ser Phe Asp Glu Tyr Trp Lys Lys Asp Ser Thr Ala Glu Leu Tyr His
                275                 280                 285

Phe Ile Gly Lys Asp Ile Val Tyr Phe His Ser Leu Phe Trp Pro Ala
290                 295                 300

Met Leu Glu Gly Ser Asn Phe Arg Lys Pro Ser Asn Leu Phe Val His
305                 310                 315                 320

Gly Tyr Val Thr Val Asn Gly Ala Lys Met Ser Lys Ser Arg Gly Thr
                325                 330                 335

Phe Ile Lys Ala Ser Thr Trp Leu Asn His Phe Asp Ala Asp Ser Leu
                340                 345                 350

Arg Tyr Tyr Tyr Thr Ala Lys Leu Ser Ser Arg Ile Asp Asp Ile Asp
                355                 360                 365

Leu Asn Leu Glu Asp Phe Val Gln Arg Val Asn Ala Asp Ile Val Asn
        370                 375                 380

Lys Val Val Asn Leu Ala Ser Arg Asn Ala Gly Phe Ile Asn Lys Arg
385                 390                 395                 400

Phe Asp Gly Val Leu Ala Ser Glu Leu Ala Asp Pro Gln Leu Tyr Lys
                405                 410                 415

Thr Phe Thr Asp Ala Ala Glu Val Ile Gly Glu Ala Trp Glu Ser Arg
                420                 425                 430

Glu Phe Gly Lys Ala Val Arg Glu Ile Met Ala Leu Ala Asp Leu Ala
        435                 440                 445

Asn Arg Tyr Val Asp Glu Gln Ala Pro Trp Val Val Ala Lys Gln Glu
        450                 455                 460

Gly Arg Asp Ala Asp Leu Gln Ala Ile Cys Ser Met Gly Ile Asn Leu
465                 470                 475                 480

Phe Arg Val Leu Met Thr Tyr Leu Lys Pro Val Leu Pro Lys Leu Thr
                485                 490                 495

Glu Arg Ala Glu Ala Phe Leu Asn Thr Glu Leu Thr Trp Asp Gly Ile
                500                 505                 510

Gln Gln Pro Leu Leu Gly His Lys Val Asn Pro Phe Lys Ala Leu Tyr
        515                 520                 525

Asn Arg Ile Asp Met Arg Gln Val Glu Ala Leu Val Glu Ala Ser Lys
530                 535                 540

<210> SEQ ID NO 4
<211> LENGTH: 544
<212> TYPE: PRT
<213> ORGANISM: Escherichia coli

<400> SEQUENCE: 4

```
Ala Lys Lys Ile Leu Val Thr Cys Ala Ser Pro Tyr Ala Asn Gly Ser
1               5                   10                  15

Ile His Leu Gly His Met Leu Glu His Ile Gln Ala Asp Val Trp Val
            20                  25                  30

Arg Tyr Gln Arg Met Arg Gly His Glu Val Asn Phe Ile Cys Ala Asp
            35                  40                  45

Asp Ala His Gly Thr Pro Ile Met Leu Lys Ala Gln Gln Leu Gly Ile
            50                  55                  60

Thr Pro Glu Gln Met Ile Gly Glu Met Ser Gln Glu His Gln Thr Asp
65                  70                  75                  80

Phe Ala Gly Phe Asn Ile Ser Tyr Asp Asn Tyr His Ser Thr His Ser
                85                  90                  95

Glu Glu Asn Arg Gln Leu Ser Glu Leu Ile Tyr Ser Arg Leu Lys Glu
                100                 105                 110

Asn Gly Phe Ile Lys Asn Arg Thr Ile Ser Gln Leu Tyr Asp Pro Glu
            115                 120                 125

Lys Gly Met Phe Leu Pro Asp Arg Phe Val Lys Gly Thr Cys Pro Lys
            130                 135                 140

Cys Lys Ser Pro Asp Gln Tyr Gly Asp Asn Cys Glu Val Cys Gly Ala
145                 150                 155                 160

Thr Tyr Ser Pro Thr Glu Leu Ile Glu Pro Lys Ser Val Val Ser Gly
                165                 170                 175

Ala Thr Pro Val Met Arg Asp Ser Glu His Phe Phe Asp Leu Pro
            180                 185                 190

Ser Phe Ser Glu Met Leu Gln Ala Trp Thr Arg Ser Gly Ala Leu Gln
            195                 200                 205

Glu Gln Val Ala Asn Lys Met Gln Glu Trp Phe Glu Ser Gly Leu Gln
            210                 215                 220

Gln Trp Asp Ile Ser Arg Asp Ala Pro Tyr Phe Gly Phe Glu Ile Pro
225                 230                 235                 240

Asn Ala Pro Gly Lys Tyr Phe Tyr Val Trp Leu Asp Ala Pro Ile Gly
                245                 250                 255

Leu Met Gly Ser Phe Lys Asn Leu Cys Asp Lys Arg Gly Asp Ser Val
            260                 265                 270

Ser Phe Asp Glu Tyr Trp Lys Lys Asp Ser Thr Ala Glu Leu Tyr His
            275                 280                 285

Phe Ile Gly Lys Gly Ile Val Tyr Phe Leu Ser Leu Phe Trp Pro Ala
            290                 295                 300

Met Leu Glu Gly Ser Asn Phe Arg Lys Pro Ser Asn Leu Phe Val His
305                 310                 315                 320

Gly Tyr Val Thr Val Asn Gly Ala Lys Met Ser Lys Ser Arg Gly Thr
                325                 330                 335

Phe Ile Lys Ala Ser Thr Trp Leu Asn His Phe Asp Ala Asp Ser Leu
            340                 345                 350

Arg Tyr Tyr Tyr Thr Ala Lys Leu Ser Ser Arg Ile Asp Asp Ile Asp
            355                 360                 365

Leu Asn Leu Glu Asp Phe Val Gln Arg Val Asn Ala Asp Ile Val Asn
            370                 375                 380

Lys Val Val Asn Leu Ala Ser Arg Asn Ala Gly Phe Ile Asn Lys Arg
385                 390                 395                 400

Phe Asp Gly Val Leu Ala Ser Glu Leu Ala Asp Pro Gln Leu Tyr Lys
                405                 410                 415
```

-continued

```
Thr Phe Thr Asp Ala Ala Glu Val Ile Gly Glu Ala Trp Glu Ser Arg
            420                 425                 430

Glu Phe Gly Lys Ala Val Arg Glu Ile Met Ala Leu Ala Asp Leu Ala
        435                 440                 445

Asn Arg Tyr Val Asp Glu Gln Ala Pro Trp Val Ala Lys Gln Glu
    450                 455                 460

Gly Arg Asp Ala Asp Leu Gln Ala Ile Cys Ser Met Gly Ile Asn Leu
465                 470                 475                 480

Phe Arg Val Leu Met Thr Tyr Leu Lys Pro Val Leu Pro Lys Leu Thr
                485                 490                 495

Glu Arg Ala Glu Ala Phe Leu Asn Thr Glu Leu Thr Trp Asp Gly Ile
            500                 505                 510

Gln Gln Pro Leu Leu Gly His Lys Val Asn Pro Phe Lys Ala Leu Tyr
        515                 520                 525

Asn Arg Ile Asp Met Arg Gln Val Glu Ala Leu Val Glu Ala Ser Lys
    530                 535                 540

<210> SEQ ID NO 5
<211> LENGTH: 677
<212> TYPE: PRT
<213> ORGANISM: Escherichia coli

<400> SEQUENCE: 5

Met Thr Gln Val Ala Lys Lys Ile Leu Val Thr Cys Ala Leu Pro Tyr
1               5                   10                  15

Ala Asn Gly Ser Ile His Leu Gly His Met Leu Glu His Ile Gln Ala
            20                  25                  30

Asp Val Trp Val Arg Tyr Gln Arg Met Arg Gly His Glu Val Asn Phe
        35                  40                  45

Ile Cys Ala Asp Asp Ala His Gly Thr Pro Ile Met Leu Lys Ala Gln
    50                  55                  60

Gln Leu Gly Ile Thr Pro Glu Gln Met Ile Gly Glu Met Ser Gln Glu
65                  70                  75                  80

His Gln Thr Asp Phe Ala Gly Phe Asn Ile Ser Tyr Asp Asn Tyr His
                85                  90                  95

Ser Thr His Ser Glu Glu Asn Arg Gln Leu Ser Glu Leu Ile Tyr Ser
            100                 105                 110

Arg Leu Lys Glu Asn Gly Phe Ile Lys Asn Arg Thr Ile Ser Gln Leu
        115                 120                 125

Tyr Asp Pro Glu Lys Gly Met Phe Leu Pro Asp Arg Phe Val Lys Gly
    130                 135                 140

Thr Cys Pro Lys Cys Lys Ser Pro Asp Gln Tyr Gly Asp Asn Cys Glu
145                 150                 155                 160

Val Cys Gly Ala Thr Tyr Ser Pro Thr Glu Leu Ile Glu Pro Lys Ser
                165                 170                 175

Val Val Ser Gly Ala Thr Pro Val Met Arg Asp Ser Glu His Phe Phe
            180                 185                 190

Phe Asp Leu Pro Ser Phe Ser Glu Met Leu Gln Ala Trp Thr Arg Ser
        195                 200                 205

Gly Ala Leu Gln Glu Gln Val Ala Asn Lys Met Gln Glu Trp Phe Glu
    210                 215                 220

Ser Gly Leu Gln Gln Trp Asp Ile Ser Arg Asp Ala Pro Tyr Phe Gly
225                 230                 235                 240

Phe Glu Ile Pro Asn Ala Pro Gly Lys Tyr Phe Tyr Val Trp Leu Asp
                245                 250                 255
```

```
Ala Pro Ile Gly Tyr Met Gly Ser Phe Lys Asn Leu Cys Asp Lys Arg
            260                 265                 270

Gly Asp Ser Val Ser Phe Asp Glu Tyr Trp Lys Lys Asp Ser Thr Ala
        275                 280                 285

Glu Leu Tyr His Phe Ile Gly Lys Asp Ile Val Tyr Phe His Ser Leu
    290                 295                 300

Phe Trp Pro Ala Met Leu Glu Gly Ser Asn Phe Arg Lys Pro Ser Asn
305                 310                 315                 320

Leu Phe Val His Gly Tyr Val Thr Val Asn Gly Ala Lys Met Ser Lys
                325                 330                 335

Ser Arg Gly Thr Phe Ile Lys Ala Ser Thr Trp Leu Asn His Phe Asp
            340                 345                 350

Ala Asp Ser Leu Arg Tyr Tyr Tyr Thr Ala Lys Leu Ser Ser Arg Ile
        355                 360                 365

Asp Asp Ile Asp Leu Asn Leu Glu Asp Phe Val Gln Arg Val Asn Ala
    370                 375                 380

Asp Ile Val Asn Lys Val Val Asn Leu Ala Ser Arg Asn Ala Gly Phe
385                 390                 395                 400

Ile Asn Lys Arg Phe Asp Gly Val Leu Ala Ser Glu Leu Ala Asp Pro
                405                 410                 415

Gln Leu Tyr Lys Thr Phe Thr Asp Ala Ala Glu Val Ile Gly Glu Ala
            420                 425                 430

Trp Glu Ser Arg Glu Phe Gly Lys Ala Val Arg Glu Ile Met Ala Leu
        435                 440                 445

Ala Asp Leu Ala Asn Arg Tyr Val Asp Glu Gln Ala Pro Trp Val Val
    450                 455                 460

Ala Lys Gln Glu Gly Arg Asp Ala Asp Leu Gln Ala Ile Cys Ser Met
465                 470                 475                 480

Gly Ile Asn Leu Phe Arg Val Leu Met Thr Tyr Leu Lys Pro Val Leu
                485                 490                 495

Pro Lys Leu Thr Glu Arg Ala Glu Ala Phe Leu Asn Thr Glu Leu Thr
            500                 505                 510

Trp Asp Gly Ile Gln Gln Pro Leu Leu Gly His Lys Val Asn Pro Phe
        515                 520                 525

Lys Ala Leu Tyr Asn Arg Ile Asp Met Arg Gln Val Glu Ala Leu Val
    530                 535                 540

Glu Ala Ser Lys Glu Glu Val Lys Ala Ala Ala Pro Val Thr Gly
545                 550                 555                 560

Pro Leu Ala Asp Asp Pro Ile Gln Glu Thr Ile Thr Phe Asp Asp Phe
                565                 570                 575

Ala Lys Val Asp Leu Arg Val Ala Leu Ile Glu Asn Ala Glu Phe Val
            580                 585                 590

Glu Gly Ser Asp Lys Leu Leu Arg Leu Thr Leu Asp Leu Gly Gly Glu
        595                 600                 605

Lys Arg Asn Val Phe Ser Gly Ile Arg Ser Ala Tyr Pro Asp Pro Gln
    610                 615                 620

Ala Leu Ile Gly Arg His Thr Ile Met Val Ala Asn Leu Ala Pro Arg
625                 630                 635                 640

Lys Met Arg Phe Gly Ile Ser Glu Gly Met Val Met Ala Ala Gly Pro
                645                 650                 655

Gly Gly Lys Asp Ile Phe Leu Leu Ser Pro Asp Ala Gly Ala Lys Pro
            660                 665                 670
```

Gly His Gln Val Lys
        675

<210> SEQ ID NO 6
<211> LENGTH: 265
<212> TYPE: PRT
<213> ORGANISM: Thermus thermophilus

<400> SEQUENCE: 6

Val Asp Val Ser Leu Pro Gly Ala Ser Leu Phe Ser Gly Gly Leu His
1               5                   10                  15

Pro Ile Thr Leu Met Glu Arg Glu Leu Val Glu Ile Phe Arg Ala Leu
            20                  25                  30

Gly Tyr Gln Ala Val Glu Gly Pro Glu Val Glu Ser Glu Phe Phe Asn
        35                  40                  45

Phe Asp Ala Leu Asn Ile Pro Glu His His Pro Ala Arg Asp Met Trp
    50                  55                  60

Asp Thr Phe Trp Leu Thr Gly Glu Gly Phe Arg Leu Glu Gly Pro Leu
65                  70                  75                  80

Gly Glu Glu Val Glu Gly Arg Leu Leu Leu Arg Thr His Thr Ser Pro
                85                  90                  95

Met Gln Val Arg Tyr Met Val Ala His Thr Pro Pro Phe Arg Ile Val
            100                 105                 110

Val Pro Gly Arg Val Phe Arg Phe Glu Gln Thr Asp Ala Thr His Glu
        115                 120                 125

Ala Val Phe His Gln Leu Glu Gly Leu Val Val Gly Glu Gly Ile Ala
    130                 135                 140

Met Ala His Leu Lys Gly Ala Ile Tyr Glu Leu Ala Gln Ala Leu Phe
145                 150                 155                 160

Gly Pro Asp Ser Lys Val Arg Phe Gln Pro Val Tyr Phe Pro Phe Val
                165                 170                 175

Glu Pro Gly Ala Gln Phe Ala Val Trp Trp Pro Glu Gly Gly Lys Trp
            180                 185                 190

Leu Glu Leu Gly Gly Ala Gly Met Val His Pro Lys Val Phe Gln Ala
        195                 200                 205

Val Asp Ala Tyr Arg Glu Arg Leu Gly Leu Pro Pro Ala Tyr Arg Gly
    210                 215                 220

Val Thr Gly Phe Ala Phe Gly Leu Gly Val Glu Arg Leu Ala Met Leu
225                 230                 235                 240

Arg Tyr Gly Ile Pro Asp Ile Arg Tyr Phe Phe Gly Gly Arg Leu Lys
                245                 250                 255

Phe Leu Glu Gln Phe Lys Gly Val Leu
            260                 265

<210> SEQ ID NO 7
<211> LENGTH: 250
<212> TYPE: PRT
<213> ORGANISM: Thermus thermophilus

<400> SEQUENCE: 7

Val Asp Val Ser Leu Pro Gly Ala Ser Leu Phe Ser Gly Gly Asp His
1               5                   10                  15

Pro Ile Thr Leu Met Glu Arg Glu Leu Val Glu Ile Phe Arg Ala Leu
            20                  25                  30

Gly Tyr Gln Ala Val Glu Gly Pro Glu Val Glu Ser Glu Phe Phe Asn
        35                  40                  45

Phe Asp Ala Leu Asn Ile Pro Glu Asn Gly Pro Ala Arg Asp Met Trp
 50                  55                  60

Asp Thr Val Gly Lys Thr Gly Glu Gly Phe Arg Leu Glu Gly Pro Asp
 65                  70                  75                  80

Gly Glu Glu Val Glu Gly Arg Leu Leu Leu Arg Thr His Thr Ser Pro
                 85                  90                  95

Met Gln Val Arg Tyr Met Val Ala His Thr Pro Pro Phe Arg Ile Val
                100                 105                 110

Val Pro Gly Arg Val Phe Arg Ala Glu Gln Thr Asp Ala Thr Ala Glu
                115                 120                 125

Ala Val Phe His Gln Leu Glu Gly Leu Val Val Gly Glu Gly Val Asn
130                 135                 140

Glu Gly Asp Leu Tyr Gly Ala Ile Tyr Glu Leu Ala Gln Ala Leu Phe
145                 150                 155                 160

Gly Pro Asp Ser Lys Val Arg Phe Gln Pro Val Thr Phe Pro Phe Val
                165                 170                 175

Glu Pro Gly Ala Gln Phe Ala Val Trp Trp Pro Glu Gly Gly Lys Trp
                180                 185                 190

Leu Glu Leu Gly Gly Ala Gly Met Val Gly Pro Asn Val Phe Gln Ala
                195                 200                 205

Val Asp Ala Tyr Arg Glu Arg Leu Gly Asp Pro Pro Ala Tyr Arg Gly
210                 215                 220

Val Thr Gly Phe Ala Phe Gly Leu Gly Val Glu Arg Leu Ala Met Leu
225                 230                 235                 240

Arg Tyr Gly Ile Pro Asp Ile Arg Tyr Phe
                245                 250

<210> SEQ ID NO 8
<211> LENGTH: 350
<212> TYPE: PRT
<213> ORGANISM: Thermus thermophilus

<400> SEQUENCE: 8

Met Leu Glu Glu Ala Leu Ala Ala Ile Gln Asn Ala Arg Asp Leu Glu
1               5                   10                  15

Glu Leu Lys Ala Leu Lys Ala Arg Tyr Leu Gly Lys Lys Gly Leu Leu
                20                  25                  30

Thr Gln Glu Met Lys Gly Leu Ser Ala Leu Pro Leu Glu Glu Arg Arg
                35                  40                  45

Lys Arg Gly Gln Glu Leu Asn Ala Ile Lys Ala Ala Leu Glu Ala Ala
            50                  55                  60

Leu Glu Ala Arg Glu Lys Ala Leu Glu Ala Ala Leu Lys Glu Ala
65                  70                  75                  80

Leu Glu Arg Glu Arg Val Asp Val Ser Leu Pro Gly Ala Ser Leu Phe
                85                  90                  95

Ser Gly Gly Leu His Pro Ile Thr Leu Met Glu Arg Glu Leu Val Glu
                100                 105                 110

Ile Phe Arg Ala Leu Gly Tyr Gln Ala Val Glu Gly Pro Glu Val Glu
                115                 120                 125

Ser Glu Phe Phe Asn Phe Asp Ala Leu Asn Ile Pro Glu His His Pro
            130                 135                 140

Ala Arg Asp Met Trp Asp Thr Phe Trp Leu Thr Gly Glu Gly Phe Arg
145                 150                 155                 160

Leu Glu Gly Pro Leu Gly Glu Glu Val Glu Gly Arg Leu Leu Leu Arg
                165                 170                 175

```
Thr His Thr Ser Pro Met Gln Val Arg Tyr Met Val Ala His Thr Pro
            180                 185                 190

Pro Phe Arg Ile Val Val Pro Gly Arg Val Phe Arg Phe Glu Gln Thr
        195                 200                 205

Asp Ala Thr His Glu Ala Val Phe His Gln Leu Glu Gly Leu Val Val
210                 215                 220

Gly Glu Gly Ile Ala Met Ala His Leu Lys Gly Ala Ile Tyr Glu Leu
225                 230                 235                 240

Ala Gln Ala Leu Phe Gly Pro Asp Ser Lys Val Arg Phe Gln Pro Val
                245                 250                 255

Tyr Phe Pro Phe Val Glu Pro Gly Ala Gln Phe Ala Val Trp Trp Pro
            260                 265                 270

Glu Gly Gly Lys Trp Leu Glu Leu Gly Gly Ala Gly Met Val His Pro
        275                 280                 285

Lys Val Phe Gln Ala Val Asp Ala Tyr Arg Glu Arg Leu Gly Leu Pro
290                 295                 300

Pro Ala Tyr Arg Gly Val Thr Gly Phe Ala Phe Gly Leu Gly Val Glu
305                 310                 315                 320

Arg Leu Ala Met Leu Arg Tyr Gly Ile Pro Asp Ile Arg Tyr Phe Phe
                325                 330                 335

Gly Gly Arg Leu Lys Phe Leu Glu Gln Phe Lys Gly Val Leu
            340                 345                 350

<210> SEQ ID NO 9
<211> LENGTH: 177
<212> TYPE: PRT
<213> ORGANISM: Escherichia coli

<400> SEQUENCE: 9

Asn Ile Gln Ala Ile Arg Gly Met Asn Asp Tyr Leu Pro Gly Glu Thr
1               5                   10                  15

Ala Ile Trp Gln Arg Ile Glu Gly Thr Leu Lys Asn Val Leu Gly Ser
            20                  25                  30

Tyr Gly Tyr Ser Glu Ile Arg Leu Pro Ile Val Glu Gln Thr Pro Leu
        35                  40                  45

Phe Lys Arg Ala Ile Gly Glu Val Thr Asp Val Val Glu Lys Glu Met
    50                  55                  60

Tyr Thr Phe Glu Asp Arg Asn Gly Asp Ser Leu Thr Leu Arg Pro Glu
65                  70                  75                  80

Gly Thr Ala Gly Cys Val Arg Ala Gly Ile Glu His Gly Leu Leu Tyr
                85                  90                  95

Asn Gln Glu Gln Arg Leu Trp Tyr Ile Gly Pro Met Phe Arg His Glu
            100                 105                 110

Arg Pro Gln Lys Gly Arg Tyr Arg Gln Phe His Gln Leu Gly Cys Glu
        115                 120                 125

Val Phe Gly Leu Gln Gly Pro Asp Ile Asp Ala Glu Leu Ile Met Leu
    130                 135                 140

Thr Ala Arg Trp Trp Arg Ala Leu Gly Ile Ser Glu His Val Thr Leu
145                 150                 155                 160

Glu Leu Asn Ser Ile Gly Ser Leu Glu Ala Arg Ala Asn Tyr Arg Asp
                165                 170                 175

Ala

<210> SEQ ID NO 10
```

```
<211> LENGTH: 171
<212> TYPE: PRT
<213> ORGANISM: Escherichia coli

<400> SEQUENCE: 10

Lys Asn Ile Gln Ala Ile Arg Gly Met Asn Asp Tyr Leu Pro Gly Glu
1               5                   10                  15

Thr Ala Ile Trp Gln Arg Ile Glu Gly Thr Leu Lys Asn Val Leu Gly
            20                  25                  30

Ser Tyr Gly Tyr Ser Glu Ile Arg Leu Pro Ile Val Glu Gln Thr Pro
        35                  40                  45

Leu Phe Lys Arg Ala Ile Gly Glu Val Thr Asp Val Val Glu Lys Glu
    50                  55                  60

Met Tyr Thr Phe Glu Asp Arg Asn Gly Asp Ser Leu Thr Leu Arg Pro
65                  70                  75                  80

Glu Gly Thr Ala Gly Cys Val Arg Ala Gly Ile Glu His Gly Leu Leu
                85                  90                  95

Tyr Asn Gln Glu Gln Arg Leu Trp Tyr Ile Gly Pro Met Phe Gly Asn
            100                 105                 110

Ala Pro Gln Phe His Gln Leu Gly Cys Glu Val Phe Gly Leu Gln Gly
        115                 120                 125

Pro Asp Ile Asp Ala Glu Leu Ile Met Leu Thr Ala Arg Trp Trp Arg
    130                 135                 140

Ala Leu Gly Ile Ser Glu His Val Thr Leu Glu Leu Asn Ser Ile Gly
145                 150                 155                 160

Ser Leu Glu Ala Arg Ala Asn Tyr Arg Asp Ala
                165                 170

<210> SEQ ID NO 11
<211> LENGTH: 258
<212> TYPE: PRT
<213> ORGANISM: Escherichia coli

<400> SEQUENCE: 11

Ser Lys Ser Thr Ala Glu Ile Arg Gln Ala Phe Leu Asp Phe Phe His
1               5                   10                  15

Ser Lys Gly His Gln Val Val Ala Ser Ser Ser Leu Val Pro His Asn
            20                  25                  30

Asp Pro Thr Leu Leu Phe Thr Asn Ala Gly Met Asn Gln Phe Lys Asp
        35                  40                  45

Val Phe Leu Gly Leu Asp Lys Arg Asn Tyr Ser Arg Ala Thr Thr Ser
    50                  55                  60

Gln Arg Cys Val Arg Ala Gly Gly Lys His Asn Asp Leu Glu Asn Val
65                  70                  75                  80

Gly Tyr Thr Ala Arg His His Thr Phe Phe Glu Met Leu Gly Asn Phe
                85                  90                  95

Ser Phe Gly Asp Tyr Phe Lys His Asp Ala Ile Gln Phe Ala Trp Glu
            100                 105                 110

Leu Leu Thr Ser Glu Lys Trp Phe Ala Leu Pro Lys Glu Arg Leu Trp
        115                 120                 125

Val Thr Val Tyr Glu Ser Asp Asp Glu Ala Tyr Glu Ile Trp Glu Lys
    130                 135                 140

Glu Val Gly Ile Pro Arg Glu Arg Ile Ile Arg Ile Gly Asp Asn Lys
145                 150                 155                 160

Gly Ala Pro Tyr Ala Ser Asp Asn Phe Trp Gln Met Gly Asp Thr Gly
                165                 170                 175
```

```
Pro Cys Gly Pro Cys Thr Glu Ile Phe Tyr Asp His Gly Asp His Ile
            180                 185                 190

Trp Gly Gly Pro Pro Gly Ser Pro Glu Glu Asp Gly Asp Arg Tyr Ile
            195                 200                 205

Glu Ile Trp Asn Ile Val Phe Met Gln Phe Asn Arg Gln Ala Asp Gly
    210                 215                 220

Thr Met Glu Pro Leu Pro Lys Pro Ser Val Asp Thr Gly Met Gly Leu
225                 230                 235                 240

Glu Arg Ile Ala Ala Val Leu Gln His Val Asn Ser Asn Tyr Asp Ile
                245                 250                 255

Asp Leu

<210> SEQ ID NO 12
<211> LENGTH: 467
<212> TYPE: PRT
<213> ORGANISM: Escherichia coli

<400> SEQUENCE: 12

Glu Lys Gln Thr Ile Val Val Asp Tyr Ser Ala Pro Asn Val Ala Lys
1               5                   10                  15

Glu Met His Val Gly His Leu Arg Ser Thr Ile Ile Gly Asp Ala Ala
            20                  25                  30

Val Arg Thr Leu Glu Phe Leu Gly His Lys Val Ile Arg Ala Asn His
        35                  40                  45

Val Gly Asp Trp Gly Thr Gln Phe Gly Met Leu Ile Ala Trp Leu Glu
    50                  55                  60

Lys Gln Gln Gln Glu Asn Ala Gly Glu Met Glu Leu Ala Asp Leu Glu
65                  70                  75                  80

Gly Phe Tyr Arg Asp Ala Lys Lys His Tyr Asp Glu Asp Glu Glu Phe
                85                  90                  95

Ala Glu Arg Ala Arg Asn Tyr Val Val Lys Leu Gln Ser Gly Asp Glu
            100                 105                 110

Tyr Phe Arg Glu Met Trp Arg Lys Leu Val Asp Ile Thr Met Thr Gln
        115                 120                 125

Asn Gln Ile Thr Tyr Asp Arg Leu Asn Val Thr Leu Thr Arg Asp Asp
    130                 135                 140

Val Met Gly Glu Ser Leu Tyr Asn Pro Met Leu Pro Gly Ile Val Ala
145                 150                 155                 160

Asp Leu Lys Ala Lys Gly Leu Ala Val Glu Ser Glu Gly Ala Thr Val
                165                 170                 175

Val Phe Leu Asp Glu Phe Lys Asn Lys Glu Gly Glu Pro Met Gly Val
            180                 185                 190

Ile Ile Gln Lys Lys Asp Gly Gly Tyr Leu Tyr Thr Thr Thr Asp Ile
        195                 200                 205

Ala Cys Ala Lys Tyr Arg Tyr Glu Ser Leu His Ala Asp Arg Val Leu
    210                 215                 220

Tyr Tyr Ile Asp Ser Arg Gln His Gln His Leu Met Gln Ala Trp Ala
225                 230                 235                 240

Ile Val Arg Lys Ala Gly Tyr Val Pro Glu Ser Val Pro Leu Glu His
                245                 250                 255

His Met Phe Gly Met Met Leu Gly Lys Asp Gly Lys Pro Phe Lys Thr
            260                 265                 270

Arg Ala Gly Gly Thr Val Lys Leu Ala Asp Leu Leu Asp Glu Thr Leu
        275                 280                 285
```

Glu Arg Ala Arg Arg Leu Val Ala Glu Lys Asn Pro Asp Met Pro Ala
    290                 295                 300

Asp Glu Leu Glu Lys Leu Ala Asn Ala Val Gly Ile Gly Ala Val Lys
305                 310                 315                 320

Tyr Ala Asp Leu Ser Lys Asn Arg Thr Thr Asp Tyr Ile Phe Asp Trp
                325                 330                 335

Asp Asn Met Leu Ala Phe Glu Gly Asn Thr Ala Pro Tyr Met Gln Tyr
            340                 345                 350

Ala Tyr Thr Arg Val Leu Ser Val Phe Arg Lys Ala Glu Ile Asn Glu
        355                 360                 365

Glu Gln Leu Ala Ala Ala Pro Val Ile Ile Arg Glu Asp Arg Glu Ala
    370                 375                 380

Gln Leu Ala Ala Arg Leu Leu Gln Phe Glu Glu Thr Leu Thr Val Val
385                 390                 395                 400

Ala Arg Glu Gly Thr Pro His Val Met Cys Ala Tyr Leu Tyr Asp Leu
                405                 410                 415

Ala Gly Leu Phe Ser Gly Phe Tyr Glu His Cys Pro Ile Leu Ser Ala
            420                 425                 430

Glu Asn Glu Glu Val Arg Asn Ser Arg Leu Lys Leu Ala Gln Leu Thr
        435                 440                 445

Ala Lys Thr Leu Lys Leu Gly Leu Asp Thr Leu Gly Ile Glu Thr Val
    450                 455                 460

Glu Arg Met
465

<210> SEQ ID NO 13
<211> LENGTH: 345
<212> TYPE: PRT
<213> ORGANISM: Escherichia coli

<400> SEQUENCE: 13

Ser Ile Glu Tyr Leu Arg Glu Val Ala His Leu Arg Pro Arg Thr Asn
1               5                   10                  15

Leu Ile Gly Ala Val Ala Arg Val Arg His Thr Leu Ala Gln Ala Leu
            20                  25                  30

His Arg Phe Phe Asn Glu Gln Gly Phe Phe Trp Val Ser Thr Pro Leu
        35                  40                  45

Ile Thr Ala Ser Asp Thr Glu Gly Ala Gly Glu Met Phe Arg Val Ser
    50                  55                  60

Thr Leu Asp Leu Glu Asn Leu Pro Arg Asn Asp Gln Gly Lys Val Asp
65                  70                  75                  80

Phe Asp Lys Asp Phe Phe Gly Lys Glu Ser Phe Leu Thr Val Ser Gly
                85                  90                  95

Gln Leu Asn Gly Glu Thr Tyr Ala Cys Ala Leu Ser Lys Ile Tyr Thr
            100                 105                 110

Phe Gly Pro Thr Phe Arg Ala Glu Asn Ser Asn Thr Ser Arg His Leu
        115                 120                 125

Ala Glu Phe Trp Met Leu Glu Pro Glu Val Ala Phe Ala Asn Leu Asn
    130                 135                 140

Asp Ile Ala Gly Leu Ala Glu Ala Met Leu Lys Tyr Val Phe Lys Ala
145                 150                 155                 160

Val Leu Glu Glu Arg Ala Asp Asp Met Lys Phe Phe Ala Glu Arg Val
                165                 170                 175

Asp Lys Asp Ala Val Ser Arg Leu Glu Arg Phe Ile Glu Ala Asp Phe

```
            180                 185                 190
Ala Gln Val Asp Tyr Thr Asp Ala Val Thr Ile Leu Glu Asn Cys Gly
        195                 200                 205

Arg Lys Phe Glu Asn Pro Val Tyr Trp Gly Val Asp Leu Ser Ser Glu
210                 215                 220

His Glu Arg Tyr Leu Ala Glu Glu His Phe Lys Ala Pro Val Val Val
225                 230                 235                 240

Lys Asn Tyr Pro Lys Asp Ile Lys Ala Phe Tyr Met Arg Leu Asn Glu
                245                 250                 255

Asp Gly Lys Thr Val Ala Ala Met Asp Val Leu Ala Pro Gly Ile Gly
            260                 265                 270

Glu Ile Ile Gly Gly Ser Gln Arg Glu Glu Arg Leu Asp Val Leu Asp
        275                 280                 285

Glu Arg Met Leu Glu Met Gly Leu Asn Lys Glu Asp Tyr Trp Trp Tyr
    290                 295                 300

Arg Asp Leu Arg Arg Tyr Gly Thr Val Pro His Ser Gly Phe Gly Leu
305                 310                 315                 320

Gly Phe Glu Arg Leu Ile Ala Tyr Val Thr Gly Val Gln Asn Val Arg
                325                 330                 335

Asp Val Ile Pro Phe Pro Arg Thr Pro
            340                 345

<210> SEQ ID NO 14
<211> LENGTH: 449
<212> TYPE: PRT
<213> ORGANISM: Escherichia coli

<400> SEQUENCE: 14

Leu Pro Leu Asp Ser Asn His Val Asn Thr Glu Glu Ala Arg Leu Lys
1               5                   10                  15

Tyr Arg Tyr Leu Asp Leu Arg Arg Pro Glu Met Ala Gln Arg Leu Lys
            20                  25                  30

Thr Arg Ala Lys Ile Thr Ser Leu Val Arg Arg Phe Met Asp Asp His
        35                  40                  45

Gly Phe Leu Asp Ile Glu Thr Pro Met Leu Thr Lys Ala Thr Pro Glu
    50                  55                  60

Gly Ala Arg Asp Tyr Leu Val Pro Ser Arg Val His Lys Gly Lys Phe
65                  70                  75                  80

Tyr Ala Leu Pro Gln Ser Pro Gln Leu Phe Lys Gln Leu Leu Met Met
                85                  90                  95

Ser Gly Phe Asp Arg Tyr Tyr Gln Ile Val Lys Cys Phe Arg Asp Glu
            100                 105                 110

Asp Leu Arg Ala Asp Arg Gln Pro Glu Phe Thr Gln Ile Asp Val Glu
        115                 120                 125

Thr Ser Phe Met Thr Ala Pro Gln Val Arg Glu Val Met Glu Ala Leu
    130                 135                 140

Val Arg His Leu Trp Leu Glu Val Lys Gly Val Asp Leu Gly Asp Phe
145                 150                 155                 160

Pro Val Met Thr Phe Ala Glu Ala Glu Arg Arg Tyr Gly Ser Asp Lys
                165                 170                 175

Pro Asp Leu Arg Asn Pro Met Glu Leu Thr Asp Val Ala Asp Leu Leu
            180                 185                 190

Arg Ser Val Glu Phe Ala Val Phe Ala Gly Pro Ala Asn Asp Pro Lys
        195                 200                 205
```

-continued

Gly Arg Val Ala Ala Leu Arg Val Pro Gly Gly Ala Ser Leu Thr Arg
        210                 215                 220

Lys Gln Ile Asp Glu Tyr Asp Asn Phe Val Lys Ile Tyr Gly Ala Lys
225                 230                 235                 240

Gly Leu Ala Tyr Ile Lys Val Asn Glu Arg Ala Lys Gly Leu Glu Gly
                245                 250                 255

Ile Asn Ser Pro Val Ala Lys Phe Leu Asn Ala Glu Ile Ile Glu Ala
            260                 265                 270

Ile Leu Asp Arg Thr Ala Ala Gln Asp Gly Asp Met Ile Phe Phe Gly
        275                 280                 285

Ala Asp Asn Lys Lys Ile Val Ala Asp Ala Met Gly Ala Leu Arg Leu
    290                 295                 300

Lys Val Gly Lys Asp Leu Gly Leu Thr Asp Glu Ser Lys Trp Ala Pro
305                 310                 315                 320

Leu Trp Val Ile Asp Phe Pro Met Phe Glu Asp Asp Gly Glu Gly Gly
                325                 330                 335

Leu Thr Ala Met His His Pro Phe Thr Ser Pro Lys Asp Met Thr Ala
            340                 345                 350

Ala Glu Leu Lys Ala Ala Pro Glu Asn Ala Val Ala Asn Ala Tyr Asp
        355                 360                 365

Met Val Ile Asn Gly Tyr Glu Val Gly Gly Gly Ser Val Arg Ile His
    370                 375                 380

Asn Gly Asp Met Gln Gln Thr Val Phe Gly Ile Leu Gly Ile Asn Glu
385                 390                 395                 400

Glu Glu Gln Arg Glu Lys Phe Gly Phe Leu Leu Asp Ala Leu Lys Tyr
                405                 410                 415

Gly Thr Pro Pro His Ala Gly Leu Ala Phe Gly Leu Asp Arg Leu Thr
            420                 425                 430

Met Leu Leu Thr Gly Thr Asp Asn Ile Arg Asp Val Ile Ala Phe Pro
        435                 440                 445

Lys

<210> SEQ ID NO 15
<211> LENGTH: 304
<212> TYPE: PRT
<213> ORGANISM: Escherichia coli

<400> SEQUENCE: 15

Met Leu Lys Ile Phe Asn Thr Leu Thr Arg Gln Lys Glu Glu Phe Lys
1               5                   10                  15

Pro Ile His Ala Gly Glu Val Gly Met Tyr Val Cys Gly Ile Thr Val
            20                  25                  30

Tyr Asp Leu Cys His Ile Gly His Gly Arg Thr Phe Val Ala Phe Asp
        35                  40                  45

Val Val Ala Arg Tyr Leu Arg Phe Leu Gly Tyr Lys Leu Lys Tyr Val
    50                  55                  60

Arg Asn Ile Thr Asp Ile Asp Asp Lys Ile Ile Lys Arg Ala Asn Glu
65                  70                  75                  80

Asn Gly Glu Ser Phe Val Ala Met Val Asp Arg Met Ile Ala Glu Met
                85                  90                  95

His Lys Asp Phe Asp Ala Leu Asn Ile Leu Arg Pro Asp Met Glu Pro
            100                 105                 110

Arg Ala Thr His His Ile Ala Glu Ile Ile Glu Leu Thr Glu Gln Leu
        115                 120                 125

-continued

```
Ile Ala Lys Gly His Ala Tyr Val Ala Asp Asn Gly Asp Val Met Phe
130                 135                 140

Asp Val Pro Thr Asp Pro Thr Tyr Gly Val Leu Ser Arg Gln Asp Leu
145                 150                 155                 160

Asp Gln Leu Gln Ala Gly Ala Arg Val Asp Val Val Asp Asp Lys Arg
                165                 170                 175

Asn Pro Met Asp Phe Val Leu Trp Lys Met Ser Lys Glu Gly Glu Pro
            180                 185                 190

Ser Trp Pro Ser Pro Trp Gly Ala Gly Arg Pro Gly Trp His Ile Glu
        195                 200                 205

Cys Ser Ala Met Asn Cys Lys Gln Leu Gly Asn His Phe Asp Ile His
210                 215                 220

Gly Gly Gly Ser Asp Leu Met Phe Pro His His Glu Asn Glu Ile Ala
225                 230                 235                 240

Gln Ser Thr Cys Ala His Asp Gly Gln Tyr Val Asn Tyr Trp Met His
                245                 250                 255

Ser Gly Met Val Met Val Asp Arg Glu Lys Met Ser Lys Ser Leu Gly
            260                 265                 270

Asn Phe Phe Thr Val Arg Asp Val Leu Lys Tyr Tyr Asp Ala Glu Thr
        275                 280                 285

Val Arg Tyr Phe Leu Met Ser Gly His Tyr Arg Ser Gln Leu Asn Tyr
290                 295                 300

<210> SEQ ID NO 16
<211> LENGTH: 253
<212> TYPE: PRT
<213> ORGANISM: Escherichia coli

<400> SEQUENCE: 16

Thr Asn Phe Ile Arg Gln Ile Ile Asp Glu Asp Leu Ala Ser Gly Lys
1               5                   10                  15

His Thr Thr Val His Thr Arg Phe Pro Pro Glu Pro Asn Gly Tyr Leu
                20                  25                  30

His Ile Gly His Ala Lys Ser Ile Cys Leu Asn Phe Gly Ile Ala Gln
            35                  40                  45

Asp Tyr Lys Gly Gln Cys Asn Leu Arg Phe Asp Asp Thr Asn Pro Val
        50                  55                  60

Lys Glu Asp Ile Glu Tyr Val Glu Ser Ile Lys Asn Asp Val Glu Trp
65                  70                  75                  80

Leu Gly Phe His Trp Ser Gly Asn Val Arg Tyr Ser Ser Asp Tyr Phe
                85                  90                  95

Asp Gln Leu His Ala Tyr Ala Ile Glu Leu Ile Asn Lys Gly Leu Ala
            100                 105                 110

Tyr Val Asp Glu Leu Thr Pro Glu Gln Ile Arg Glu Tyr Arg Gly Thr
        115                 120                 125

Leu Thr Gln Pro Gly Lys Asn Ser Pro Tyr Arg Asp Arg Ser Val Glu
130                 135                 140

Glu Asn Leu Ala Leu Phe Glu Lys Met Arg Thr Gly Gly Phe Glu Glu
145                 150                 155                 160

Gly Lys Ala Cys Leu Arg Ala Lys Ile Asp Met Ala Ser Pro Phe Ile
                165                 170                 175

Val Met Arg Asp Pro Val Leu Tyr Arg Ile Lys Phe Ala Glu His His
            180                 185                 190

Gln Thr Gly Asn Lys Trp Cys Ile Tyr Pro Met Tyr Asp Phe Thr His
        195                 200                 205
```

```
Cys Ile Ser Asp Ala Leu Glu Gly Ile Thr His Ser Leu Cys Thr Leu
            210                 215                 220
Glu Phe Gln Asp Asn Arg Arg Leu Tyr Asp Trp Val Leu Asp Asn Ile
225                 230                 235                 240
Thr Ile Pro Val His Pro Arg Gln Tyr Glu Phe Ser Arg
            245                 250

<210> SEQ ID NO 17
<211> LENGTH: 309
<212> TYPE: PRT
<213> ORGANISM: Escherichia coli

<400> SEQUENCE: 17

Ile Lys Thr Arg Phe Ala Pro Ser Pro Thr Gly Tyr Leu His Val Gly
1               5                   10                  15
Gly Ala Arg Thr Ala Leu Tyr Ser Trp Leu Phe Ala Arg Asn His Gly
            20                  25                  30
Gly Glu Phe Val Leu Arg Ile Glu Asp Thr Asp Leu Glu Arg Ser Thr
        35                  40                  45
Pro Glu Ala Ile Glu Ala Ile Met Asp Gly Met Asn Trp Leu Ser Leu
50                  55                  60
Glu Trp Asp Glu Gly Pro Tyr Tyr Gln Thr Lys Arg Phe Asp Arg Tyr
65                  70                  75                  80
Asn Ala Val Ile Asp Gln Met Leu Glu Gly Thr Ala Tyr Lys Cys
            85                  90                  95
Tyr Cys Ser Lys Glu Arg Leu Glu Ala Leu Arg Glu Glu Gln Met Ala
            100                 105                 110
Lys Gly Glu Lys Pro Arg Tyr Asp Gly Arg Cys Arg His Ser His Glu
        115                 120                 125
His His Ala Asp Asp Glu Pro Cys Val Val Arg Phe Ala Asn Pro Gln
130                 135                 140
Glu Gly Ser Val Val Phe Asp Asp Gln Ile Arg Gly Pro Ile Glu Phe
145                 150                 155                 160
Ser Asn Gln Glu Leu Asp Asp Leu Ile Ile Arg Arg Thr Asp Gly Ser
            165                 170                 175
Pro Thr Tyr Asn Phe Cys Val Val Asp Asp Trp Asp Met Glu Ile
            180                 185                 190
Thr His Val Ile Arg Gly Glu Asp His Ile Asn Asn Thr Pro Arg Gln
        195                 200                 205
Ile Asn Ile Leu Lys Ala Leu Asn Ala Pro Val Pro Val Tyr Ala His
    210                 215                 220
Val Ser Met Ile Asn Gly Asp Asp Gly Lys Lys Leu Ser Lys Arg His
225                 230                 235                 240
Gly Ala Val Ser Val Met Gln Tyr Arg Asp Asp Gly Tyr Leu Pro Glu
            245                 250                 255
Ala Leu Leu Asn Tyr Leu Val Arg Leu Gly Trp Ser His Gly Asp Gln
        260                 265                 270
Glu Ile Phe Thr Arg Glu Glu Met Ile Lys Tyr Phe Thr Leu Asn Ala
    275                 280                 285
Val Ser Lys Ser Ala Ser Ala Phe Asn Thr Asp Lys Leu Leu Trp Leu
290                 295                 300
Asn His His Tyr Ile
305
```

<210> SEQ ID NO 18
<211> LENGTH: 767
<212> TYPE: PRT
<213> ORGANISM: Escherichia coli

<400> SEQUENCE: 18

Phe Pro Met Arg Gly Asp Leu Ala Lys Arg Glu Pro Gly Met Leu Ala
1               5                   10                  15

Arg Trp Thr Asp Asp Leu Tyr Gly Ile Ile Arg Ala Ala Lys Lys
            20                  25                  30

Gly Lys Lys Thr Phe Ile Leu His Asp Gly Pro Pro Tyr Ala Asn Gly
            35                  40                  45

Ser Ile His Ile Gly His Ser Val Asn Lys Ile Leu Lys Asp Ile Ile
    50                  55                  60

Ile Lys Ser Lys Gly Leu Ser Gly Tyr Asp Ser Pro Tyr Val Pro Gly
65              70                  75                  80

Trp Asp Cys His Gly Leu Pro Ile Glu Leu Lys Val Glu Gln Glu Tyr
                85                  90                  95

Gly Lys Pro Gly Glu Lys Phe Thr Ala Ala Glu Phe Arg Ala Lys Cys
            100                 105                 110

Arg Glu Tyr Ala Ala Thr Gln Val Asp Gly Gln Arg Lys Asp Phe Ile
        115                 120                 125

Arg Leu Gly Val Leu Gly Asp Trp Ser His Pro Tyr Leu Thr Met Asp
130                 135                 140

Phe Lys Thr Glu Ala Asn Ile Ile Arg Ala Leu Gly Lys Ile Ile Gly
145                 150                 155                 160

Asn Gly His Leu His Lys Gly Ala Lys Pro Val His Trp Cys Val Asp
                165                 170                 175

Cys Arg Ser Ala Leu Ala Glu Ala Glu Val Glu Tyr Tyr Asp Lys Thr
            180                 185                 190

Ser Pro Ser Ile Val Ala Phe Gln Ala Val Asp Gln Asp Ala Leu Lys
        195                 200                 205

Thr Lys Phe Gly Val Ser Asn Val Asn Gly Pro Ile Ser Leu Val Ile
210                 215                 220

Trp Thr Thr Thr Pro Trp Thr Leu Pro Ala Asn Arg Ala Ile Ser Ile
225                 230                 235                 240

Ala Pro Asp Phe Asp Tyr Ala Leu Val Gln Ile Asp Gly Gln Ala Val
                245                 250                 255

Ile Leu Ala Lys Asp Leu Val Glu Ser Met Gln Arg Ile Gly Val Ser
            260                 265                 270

Asp Tyr Thr Ile Leu Gly Thr Val Lys Gly Ala Glu Leu Glu Leu Leu
        275                 280                 285

Arg Phe Thr His Pro Phe Met Asp Phe Asp Val Pro Ala Ile Leu Gly
290                 295                 300

Asp His Val Thr Leu Asp Ala Gly Thr Gly Ala Val His Thr Ala Pro
305                 310                 315                 320

Gly His Gly Pro Asp Asp Tyr Val Ile Gly Gln Lys Tyr Gly Leu Glu
                325                 330                 335

Thr Ala Asn Pro Val Gly Pro Asp Gly Thr Tyr Leu Pro Gly Thr Tyr
            340                 345                 350

Pro Thr Leu Asp Gly Val Asn Val Phe Lys Ala Asn Asp Ile Val Val
        355                 360                 365

Ala Leu Leu Gln Glu Lys Gly Ala Leu Leu His Val Glu Lys Met Gln
370                 375                 380

His Ser Tyr Pro Cys Cys Trp Arg His Lys Thr Pro Ile Ile Phe Arg
385                 390                 395                 400

Ala Thr Pro Gln Trp Phe Val Ser Met Asp Gln Lys Gly Leu Arg Ala
            405                 410                 415

Gln Ser Leu Lys Glu Ile Lys Gly Val Gln Trp Ile Pro Asp Trp Gly
            420                 425                 430

Gln Ala Arg Ile Glu Ser Met Val Ala Asn Arg Pro Asp Trp Cys Ile
            435                 440                 445

Ser Arg Gln Arg Thr Trp Gly Val Pro Met Ser Leu Phe Val His Lys
450                 455                 460

Asp Thr Glu Glu Leu His Pro Arg Thr Leu Glu Leu Met Glu Glu Val
465                 470                 475                 480

Ala Lys Arg Val Glu Val Asp Gly Ile Gln Ala Trp Trp Asp Leu Asp
            485                 490                 495

Ala Lys Glu Ile Leu Gly Asp Glu Ala Asp Gln Tyr Val Lys Val Pro
            500                 505                 510

Asp Thr Leu Asp Val Trp Phe Asp Ser Gly Ser Thr His Ser Ser Val
            515                 520                 525

Val Asp Val Arg Pro Glu Phe Ala Gly His Ala Asp Met Tyr Leu
530                 535                 540

Glu Gly Ser Asp Gln His Arg Gly Trp Phe Met Ser Ser Leu Met Ile
545                 550                 555                 560

Ser Thr Ala Met Lys Gly Lys Ala Pro Tyr Arg Gln Val Leu Thr His
            565                 570                 575

Gly Phe Thr Val Asp Gly Gln Gly Arg Lys Met Ser Lys Ser Ile Gly
            580                 585                 590

Asn Thr Val Ser Pro Gln Asp Val Met Asn Lys Leu Gly Ala Asp Ile
            595                 600                 605

Leu Arg Leu Trp Val Ala Ser Thr Asp Tyr Thr Gly Glu Met Ala Val
            610                 615                 620

Ser Asp Glu Ile Leu Lys Arg Ala Ala Asp Ser Tyr Arg Arg Ile Arg
625                 630                 635                 640

Asn Thr Ala Arg Phe Leu Leu Ala Asn Leu Asn Gly Phe Asp Pro Ala
            645                 650                 655

Lys Asp Met Val Lys Pro Glu Glu Met Val Val Leu Asp Arg Trp Ala
            660                 665                 670

Val Gly Cys Ala Lys Ala Ala Gln Glu Asp Ile Leu Lys Ala Tyr Glu
            675                 680                 685

Ala Tyr Asp Phe His Glu Val Val Gln Arg Leu Met Arg Phe Cys Ser
            690                 695                 700

Val Glu Met Gly Ser Phe Tyr Leu Asp Ile Ile Lys Asp Arg Gln Tyr
705                 710                 715                 720

Thr Ala Lys Ala Asp Ser Val Ala Arg Arg Ser Cys Gln Thr Ala Leu
            725                 730                 735

Tyr His Ile Ala Glu Ala Leu Val Arg Trp Met Ala Pro Ile Leu Ser
            740                 745                 750

Phe Thr Ala Asp Glu Val Trp Gly Tyr Leu Pro Gly Glu Arg Glu
            755                 760                 765

<210> SEQ ID NO 19
<211> LENGTH: 779
<212> TYPE: PRT
<213> ORGANISM: Escherichia coli

<400> SEQUENCE: 19

-continued

```
Ile Glu Ser Lys Val Gln Leu His Trp Asp Glu Lys Arg Thr Phe Glu
1               5                   10                  15

Val Thr Glu Asp Glu Ser Lys Glu Lys Tyr Tyr Cys Leu Ser Met Leu
            20                  25                  30

Pro Tyr Pro Ser Gly Arg Leu His Met Gly His Val Arg Asn Tyr Thr
        35                  40                  45

Ile Gly Asp Val Ile Ala Arg Tyr Gln Arg Met Leu Gly Lys Asn Val
50                  55                  60

Leu Gln Pro Ile Gly Trp Asp Ala Phe Gly Leu Pro Ala Glu Gly Ala
65                  70                  75                  80

Ala Val Lys Asn Asn Thr Ala Pro Ala Pro Trp Thr Tyr Asp Asn Ile
                85                  90                  95

Ala Tyr Met Lys Asn Gln Leu Lys Met Leu Gly Phe Gly Tyr Asp Trp
            100                 105                 110

Ser Arg Glu Leu Ala Thr Cys Thr Pro Glu Tyr Tyr Arg Trp Glu Gln
        115                 120                 125

Lys Cys Phe Thr Glu Leu Tyr Lys Lys Gly Leu Val Tyr Lys Lys Thr
130                 135                 140

Ser Ala Val Asn Trp Cys Pro Asn Asp Gln Thr Val Leu Ala Asn Glu
145                 150                 155                 160

Gln Val Ile Asp Gly Cys Cys Trp Arg Cys Asp Thr Lys Val Glu Arg
                165                 170                 175

Lys Glu Ile Pro Gln Trp Phe Ile Lys Ile Thr Ala Tyr Ala Asp Glu
            180                 185                 190

Leu Leu Asn Asp Leu Asp Lys Leu Asp His Trp Pro Asp Thr Val Lys
        195                 200                 205

Thr Met Gln Arg Asn Trp Ile Gly Arg Ser Glu Gly Val Glu Ile Thr
210                 215                 220

Phe Asn Val Lys Asp Tyr Asp Asn Thr Leu Thr Val Tyr Thr Thr Arg
225                 230                 235                 240

Pro Asp Thr Phe Met Gly Cys Thr Tyr Leu Ala Val Ala Ala Gly His
                245                 250                 255

Pro Leu Ala Gln Lys Ala Ala Glu Asn Asn Pro Glu Leu Ala Ala Phe
            260                 265                 270

Ile Asp Glu Cys Arg Asn Thr Lys Val Ala Glu Ala Glu Met Ala Thr
        275                 280                 285

Met Glu Lys Lys Gly Val Asp Thr Gly Phe Lys Ala Val His Pro Leu
290                 295                 300

Thr Gly Glu Glu Ile Pro Val Trp Ala Ala Asn Phe Val Leu Met Glu
305                 310                 315                 320

Tyr Gly Thr Gly Ala Val Met Ala Val Pro Gly His Asp Gln Arg Asp
                325                 330                 335

Tyr Glu Phe Ala Ser Lys Tyr Gly Leu Asn Ile Lys Pro Val Ile Leu
            340                 345                 350

Ala Ala Asp Gly Ser Glu Pro Asp Leu Ser Gln Gln Ala Leu Thr Glu
        355                 360                 365

Lys Gly Val Leu Phe Asn Ser Gly Glu Phe Asn Gly Leu Asp His Glu
370                 375                 380

Ala Ala Phe Asn Ala Ile Ala Asp Lys Leu Thr Glu Met Gly Val Gly
385                 390                 395                 400

Glu Arg Lys Val Asn Tyr Arg Leu Arg Asp Trp Gly Val Ser Arg Gln
                405                 410                 415
```

Arg Tyr Trp Gly Ala Pro Ile Pro Met Val Thr Leu Glu Asp Gly Thr
            420             425                 430

Val Met Pro Thr Pro Asp Asp Gln Leu Pro Val Ile Leu Pro Glu Asp
435                 440                 445

Val Val Met Asp Gly Ile Thr Ser Pro Ile Lys Ala Asp Pro Glu Trp
        450                 455                 460

Ala Lys Thr Thr Val Asn Gly Met Pro Ala Leu Arg Glu Thr Asp Thr
465                 470                 475                 480

Phe Asp Thr Phe Met Glu Ser Ser Trp Tyr Tyr Ala Arg Tyr Thr Cys
                485                 490                 495

Pro Glu Tyr Lys Glu Gly Met Leu Asp Ser Lys Ala Ala Asn Tyr Trp
            500                 505                 510

Leu Pro Val Asp Ile Tyr Ile Gly Gly Ile Glu His Ala Ile Met His
        515                 520                 525

Leu Leu Tyr Phe Arg Phe Phe His Lys Leu Met Arg Asp Ala Gly Met
    530                 535                 540

Val Asn Ser Asp Glu Pro Ala Lys Gln Leu Leu Cys Gln Gly Met Val
545                 550                 555                 560

Leu Ala Asp Ala Phe Tyr Tyr Val Gly Glu Asn Gly Glu Arg Asn Trp
                565                 570                 575

Val Ser Pro Val Asp Ala Ile Val Glu Arg Asp Glu Lys Gly Arg Ile
            580                 585                 590

Val Lys Ala Lys Asp Ala Ala Gly His Glu Leu Val Tyr Thr Gly Met
        595                 600                 605

Ser Lys Met Ser Lys Ser Lys Asn Asn Gly Ile Asp Pro Gln Val Met
    610                 615                 620

Val Glu Arg Tyr Gly Ala Asp Thr Val Arg Leu Phe Met Met Phe Ala
625                 630                 635                 640

Ser Pro Ala Asp Met Thr Leu Glu Trp Gln Glu Ser Gly Val Glu Gly
                645                 650                 655

Ala Asn Arg Phe Leu Lys Arg Val Trp Lys Leu Val Tyr Glu His Thr
            660                 665                 670

Ala Lys Gly Asp Val Ala Ala Leu Asn Val Asp Ala Leu Thr Glu Asp
        675                 680                 685

Gln Lys Ala Leu Arg Arg Asp Val His Lys Thr Ile Ala Lys Val Thr
    690                 695                 700

Asp Asp Ile Gly Arg Arg Gln Thr Phe Asn Thr Ala Ile Ala Ala Ile
705                 710                 715                 720

Met Glu Leu Met Asn Lys Leu Ala Lys Ala Pro Thr Asp Gly Glu Gln
                725                 730                 735

Asp Arg Ala Leu Met Gln Glu Ala Leu Leu Ala Val Val Arg Met Leu
            740                 745                 750

Asn Pro Phe Thr Pro His Ile Cys Phe Thr Leu Trp Gln Glu Leu Lys
        755                 760                 765

Gly Glu Gly Asp Ile Asp Asn Ala Pro Trp Pro
    770                 775

<210> SEQ ID NO 20
<211> LENGTH: 328
<212> TYPE: PRT
<213> ORGANISM: Escherichia coli

<400> SEQUENCE: 20

Ala Asn Asp Lys Ser Arg Gln Thr Phe Val Val Arg Ser Lys Ile Leu
1               5                   10                  15

Ala Ala Ile Arg Gln Phe Met Val Ala Arg Gly Phe Met Glu Val Glu
            20                  25                  30

Thr Pro Met Met Gln Val Ile Pro Gly Gly Ala Ser Ala Arg Pro Phe
        35                  40                  45

Ile Thr His His Asn Ala Leu Asp Leu Asp Met Tyr Leu Arg Ile Ala
    50                  55                  60

Pro Glu Leu Tyr Leu Lys Arg Leu Val Val Gly Gly Phe Glu Arg Val
65                  70                  75                  80

Phe Glu Ile Asn Arg Asn Phe Arg Asn Glu Gly Ile Ser Val Arg His
                85                  90                  95

Asn Pro Glu Phe Thr Met Met Glu Leu Tyr Met Ala Tyr Ala Asp Tyr
            100                 105                 110

His Asp Leu Ile Glu Leu Thr Glu Ser Leu Phe Arg Thr Leu Ala Gln
        115                 120                 125

Glu Val Leu Gly Thr Thr Lys Val Thr Tyr Gly Glu His Val Phe Asp
130                 135                 140

Phe Gly Lys Pro Phe Glu Lys Leu Thr Met Arg Glu Ala Ile Lys Lys
145                 150                 155                 160

Tyr Arg Pro Glu Thr Asp Met Ala Asp Leu Asp Asn Phe Asp Ala Ala
                165                 170                 175

Lys Ala Leu Ala Glu Ser Ile Gly Ile Thr Val Glu Lys Ser Trp Gly
            180                 185                 190

Leu Gly Arg Ile Val Thr Glu Ile Phe Asp Glu Val Ala Glu Ala His
        195                 200                 205

Leu Ile Gln Pro Thr Phe Ile Thr Glu Tyr Pro Ala Glu Val Ser Pro
210                 215                 220

Leu Ala Arg Arg Asn Asp Val Asn Pro Glu Ile Thr Asp Arg Phe Glu
225                 230                 235                 240

Phe Phe Ile Gly Gly Arg Glu Ile Gly Asn Gly Phe Ser Glu Leu Asn
                245                 250                 255

Asp Ala Glu Asp Gln Ala Glu Arg Phe Gln Glu Gln Val Asn Ala Lys
            260                 265                 270

Ala Ala Gly Asp Asp Glu Ala Met Phe Tyr Asp Glu Asp Tyr Val Thr
        275                 280                 285

Ala Leu Glu Tyr Gly Leu Pro Pro Thr Ala Gly Leu Gly Ile Gly Ile
290                 295                 300

Asp Arg Met Ile Met Leu Phe Thr Asn Ser His Thr Ile Arg Asp Val
305                 310                 315                 320

Ile Leu Phe Pro Ala Met Arg Pro
                325

<210> SEQ ID NO 21
<211> LENGTH: 388
<212> TYPE: PRT
<213> ORGANISM: Escherichia coli

<400> SEQUENCE: 21

Met Ile Arg Lys Leu Ala Ser Gly Leu Tyr Thr Trp Leu Pro Thr Gly
1               5                   10                  15

Val Arg Val Leu Lys Lys Val Glu Asn Ile Val Arg Glu Glu Met Asn
            20                  25                  30

Asn Ala Gly Ala Ile Glu Val Leu Met Pro Val Val Gln Pro Ser Glu
        35                  40                  45

Leu Trp Gln Glu Ser Gly Arg Trp Glu Gln Tyr Gly Pro Glu Leu Leu

```
            50                  55                  60
Arg Ile Ala Asp Arg Gly Asp Arg Pro Phe Val Leu Gly Pro Thr His
 65                  70                  75                  80

Glu Glu Val Ile Thr Asp Leu Ile Arg Asn Glu Leu Ser Ser Tyr Lys
                 85                  90                  95

Gln Leu Pro Leu Asn Phe Tyr Gln Ile Gln Thr Lys Phe Arg Asp Glu
                100                 105                 110

Val Arg Pro Arg Phe Gly Val Met Arg Ser Arg Glu Phe Leu Met Lys
            115                 120                 125

Asp Ala Tyr Ser Phe His Thr Ser Gln Glu Ser Leu Gln Glu Thr Tyr
130                 135                 140

Asp Ala Met Tyr Ala Ala Tyr Ser Lys Ile Phe Ser Arg Met Gly Leu
145                 150                 155                 160

Asp Phe Arg Ala Val Gln Ala Asp Thr Gly Ser Ile Gly Gly Ser Ala
                165                 170                 175

Ser His Glu Phe Gln Val Leu Ala Gln Ser Gly Glu Asp Asp Val Val
                180                 185                 190

Phe Ser Asp Thr Ser Asp Tyr Ala Ala Asn Ile Glu Leu Ala Glu Ala
            195                 200                 205

Ile Ala Pro Lys Glu Pro Arg Ala Ala Thr Gln Glu Met Thr Leu
210                 215                 220

Val Asp Thr Pro Asn Ala Lys Thr Ile Ala Glu Leu Val Glu Gln Phe
225                 230                 235                 240

Asn Leu Pro Ile Glu Lys Thr Val Lys Thr Leu Leu Val Lys Ala Val
                245                 250                 255

Glu Gly Ser Ser Phe Pro Leu Val Ala Leu Leu Val Arg Gly Asp His
                260                 265                 270

Glu Leu Asn Glu Val Lys Ala Gly Lys Leu Pro Gln Val Ala Ser Pro
            275                 280                 285

Leu Thr Phe Ala Thr Glu Glu Ile Arg Ala Val Val Lys Ala Gly
        290                 295                 300

Pro Gly Ser Leu Gly Pro Val Asn Met Pro Ile Pro Val Val Ile Asp
305                 310                 315                 320

Arg Thr Val Ala Ala Met Ser Asp Phe Ala Ala Gly Ala Asn Ile Asp
                325                 330                 335

Gly Lys His Tyr Phe Gly Ile Asn Trp Asp Arg Asp Val Ala Thr Pro
                340                 345                 350

Glu Ile Ala Asp Ile Arg Asn Val Val Ala Gly Asp Pro Ser Pro Asp
            355                 360                 365

Gly Gln Gly Thr Leu Leu Ile Lys Arg Gly Ile Glu Val Gly His Ile
        370                 375                 380

Phe Gln Leu Gly
385

<210> SEQ ID NO 22
<211> LENGTH: 429
<212> TYPE: PRT
<213> ORGANISM: Escherichia coli

<400> SEQUENCE: 22

Met Leu Asp Pro Asn Leu Leu Arg Asn Glu Pro Asp Ala Val Ala Glu
 1               5                  10                  15

Lys Leu Ala Arg Arg Gly Phe Lys Leu Asp Val Asp Lys Leu Gly Ala
            20                  25                  30
```

Leu Glu Glu Arg Arg Lys Val Leu Gln Val Lys Thr Glu Asn Leu Gln
            35                  40                  45

Ala Glu Arg Asn Ser Arg Ser Lys Ser Ile Gly Gln Ala Lys Ala Arg
 50                  55                  60

Gly Glu Asp Ile Glu Pro Leu Arg Leu Glu Val Asn Lys Leu Gly Glu
 65                  70                  75                  80

Glu Leu Asp Ala Ala Lys Ala Glu Leu Asp Ala Leu Gln Ala Glu Ile
                85                  90                  95

Arg Asp Ile Ala Leu Thr Ile Pro Asn Leu Pro Ala Asp Glu Val Pro
                100                 105                 110

Val Gly Lys Asp Glu Asn Asp Asn Val Glu Val Ser Arg Trp Gly Thr
                115                 120                 125

Pro Arg Glu Phe Asp Phe Glu Val Arg Asp His Val Thr Leu Gly Glu
                130                 135                 140

Met Tyr Ser Gly Leu Asp Phe Ala Ala Ala Val Lys Leu Thr Gly Ser
145                 150                 155                 160

Arg Phe Val Val Met Lys Gly Gln Ile Ala Arg Met His Arg Ala Leu
                165                 170                 175

Ser Gln Phe Met Leu Asp Leu His Thr Glu Gln His Gly Tyr Ser Glu
                180                 185                 190

Asn Tyr Val Pro Tyr Leu Val Asn Gln Asp Thr Leu Tyr Gly Thr Gly
                195                 200                 205

Gln Leu Pro Lys Phe Ala Gly Asp Leu Phe His Thr Arg Pro Leu Glu
                210                 215                 220

Glu Glu Ala Asp Thr Ser Asn Tyr Ala Leu Ile Pro Thr Ala Glu Val
225                 230                 235                 240

Pro Leu Thr Asn Leu Val Arg Gly Glu Ile Ile Asp Glu Asp Asp Leu
                245                 250                 255

Pro Ile Lys Met Thr Ala His Thr Pro Cys Phe Arg Ser Glu Ala Gly
                260                 265                 270

Ser Tyr Gly Arg Asp Thr Arg Gly Leu Ile Arg Met His Gln Phe Asp
                275                 280                 285

Lys Val Glu Met Val Gln Ile Val Arg Pro Glu Asp Ser Met Ala Ala
                290                 295                 300

Leu Glu Glu Met Thr Gly His Ala Glu Lys Val Leu Gln Leu Leu Gly
305                 310                 315                 320

Leu Pro Tyr Arg Lys Ile Ile Leu Cys Thr Gly Asp Met Gly Phe Gly
                325                 330                 335

Ala Cys Lys Thr Tyr Asp Leu Glu Val Trp Ile Pro Ala Gln Asn Thr
                340                 345                 350

Tyr Arg Glu Ile Ser Ser Cys Ser Asn Val Trp Asp Phe Gln Ala Arg
                355                 360                 365

Arg Met Gln Ala Arg Cys Arg Ser Lys Ser Asp Lys Lys Thr Arg Leu
                370                 375                 380

Val His Thr Leu Asn Gly Ser Gly Leu Ala Val Gly Thr Arg Leu Val
385                 390                 395                 400

Ala Val Met Glu Asn Tyr Gln Gln Ala Asp Gly Arg Ile Glu Val Pro
                405                 410                 415

Glu Val Leu Arg Pro Tyr Met Asn Gly Leu Glu Tyr Ile
                420                 425

<210> SEQ ID NO 23
<211> LENGTH: 401
<212> TYPE: PRT

<213> ORGANISM: Escherichia coli

<400> SEQUENCE: 23

```
Arg Asp His Arg Lys Ile Gly Lys Gln Leu Asp Leu Tyr His Met Gln
1               5                   10                  15

Glu Glu Ala Pro Gly Met Val Phe Trp His Asn Asp Gly Trp Thr Ile
            20                  25                  30

Phe Arg Glu Leu Glu Val Phe Val Arg Ser Lys Leu Lys Glu Tyr Gln
        35                  40                  45

Tyr Gln Glu Val Lys Gly Pro Phe Met Met Asp Arg Val Leu Trp Glu
    50                  55                  60

Lys Thr Gly His Trp Asp Asn Tyr Lys Asp Ala Met Phe Thr Thr Ser
65                  70                  75                  80

Ser Glu Asn Arg Glu Tyr Cys Ile Lys Pro Met Asn Cys Pro Gly His
                85                  90                  95

Val Gln Ile Phe Asn Gln Gly Leu Lys Ser Tyr Arg Asp Leu Pro Leu
            100                 105                 110

Arg Met Ala Glu Phe Gly Ser Cys His Arg Asn Glu Pro Ser Gly Ser
        115                 120                 125

Leu His Gly Leu Gly Arg Val Arg Gly Phe Thr Gln Asp Asp Ala His
    130                 135                 140

Ile Phe Cys Thr Glu Glu Gln Ile Arg Asp Glu Val Asn Gly Cys Ile
145                 150                 155                 160

Arg Leu Val Tyr Asp Met Tyr Ser Thr Phe Gly Phe Glu Lys Ile Val
                165                 170                 175

Val Lys Leu Ser Thr Arg Pro Glu Lys Arg Ile Gly Ser Asp Glu Met
            180                 185                 190

Trp Asp Arg Ala Glu Ala Asp Leu Ala Val Ala Leu Glu Glu Asn Asn
        195                 200                 205

Ile Pro Phe Glu Tyr Gln Leu Gly Glu Gly Ala Phe Tyr Gly Pro Lys
    210                 215                 220

Ile Glu Phe Thr Leu Tyr Asp Cys Leu Asp Arg Ala Ala Gln Cys Gly
225                 230                 235                 240

Thr Val Gln Leu Asp Phe Ser Leu Pro Ser Arg Leu Ser Ala Ser Tyr
                245                 250                 255

Val Gly Glu Asp Asn Glu Arg Lys Val Pro Val Met Ile His Arg Ala
            260                 265                 270

Ile Leu Gly Ser Met Glu Val Phe Ile Gly Ile Leu Thr Glu Glu Phe
        275                 280                 285

Ala Gly Phe Phe Pro Thr Trp Leu Ala Pro Val Gln Val Val Ile Met
    290                 295                 300

Asn Ile Thr Asp Ser Gln Ser Glu Tyr Val Asn Glu Leu Thr Gln Lys
305                 310                 315                 320

Leu Ser Asn Ala Gly Ile Arg Val Lys Ala Asp Leu Arg Asn Glu Lys
                325                 330                 335

Ile Gly Phe Lys Ile Arg Glu His Thr Leu Arg Arg Val Pro Tyr Met
            340                 345                 350

Leu Val Cys Gly Asp Lys Glu Val Glu Ser Gly Lys Val Ala Val Arg
        355                 360                 365

Thr Arg Arg Gly Lys Asp Leu Gly Ser Met Asp Val Asn Glu Val Ile
    370                 375                 380

Glu Lys Leu Gln Gln Glu Ile Arg Ser Arg Ser Leu Lys Gln Leu Glu
385                 390                 395                 400
```

Glu

<210> SEQ ID NO 24
<211> LENGTH: 264
<212> TYPE: PRT
<213> ORGANISM: Escherichia coli

<400> SEQUENCE: 24

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Ile Asn Met Gln
            20                  25                  30

Asp Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
            100                 105                 110

Lys Ser Ala Arg Tyr Ala Glu Asn Ile Asn Ala Gly Leu Phe Asp Tyr
        115                 120                 125

Pro Val Leu Met Ala Ala Asp Ile Leu Leu Tyr Gln Thr Asn Leu Val
    130                 135                 140

Pro Val Gly Glu Asp Gln Lys Gln His Leu Glu Leu Ser Arg Asp Ile
145                 150                 155                 160

Ala Gln Arg Phe Asn Ala Leu Tyr Gly Asp Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asp Asn Arg Asn Asn Val Ile Gly
        195                 200                 205

Leu Leu Glu Asp Pro Lys Ser Val Val Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln
            260

<210> SEQ ID NO 25
<211> LENGTH: 424
<212> TYPE: PRT
<213> ORGANISM: Escherichia coli

<400> SEQUENCE: 25

Met Ala Ser Ser Asn Leu Ile Lys Gln Leu Gln Glu Arg Gly Leu Val
1               5                   10                  15

Ala Gln Val Thr Asp Glu Glu Ala Leu Val Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala

```
            50                  55                  60
Gly His Lys Pro Val Ala Leu Val Gly Gly Ala Thr Gly Leu Ile Gly
 65                  70                  75                  80

Asp Pro Ser Phe Lys Ala Ala Glu Arg Lys Leu Asn Thr Glu Glu Thr
                 85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
            130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Lys
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 26
<211> LENGTH: 763
<212> TYPE: PRT
<213> ORGANISM: Escherichia coli

<400> SEQUENCE: 26
```

```
Met Glu Lys Thr Tyr Asn Pro Gln Asp Ile Glu Gln Pro Leu Tyr Glu
1               5                   10                  15

His Trp Glu Lys Gln Gly Tyr Phe Lys Pro Asn Gly Asp Glu Ser Gln
            20                  25                  30

Glu Ser Phe Cys Ile Met Ile Pro Pro Asn Val Thr Gly Ser Leu
        35                  40                  45

His Met Gly His Ala Phe Gln Gln Thr Ile Met Asp Thr Met Ile Arg
50                  55                  60

Tyr Gln Arg Met Gln Gly Lys Asn Thr Leu Trp Gln Val Gly Thr Asp
65                  70                  75                  80

His Ala Gly Ile Ala Thr Gln Met Val Val Glu Arg Lys Ile Ala Ala
                85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
            115                 120                 125

Met Arg Arg Leu Gly Asn Ser Val Asp Trp Glu Arg Glu Arg Phe Thr
    130                 135                 140

Met Asp Glu Gly Leu Ser Asn Ala Val Lys Glu Val Phe Val Arg Leu
145                 150                 155                 160

Tyr Lys Glu Asp Leu Ile Tyr Arg Gly Lys Arg Leu Val Asn Trp Asp
                165                 170                 175

Pro Lys Leu Arg Thr Ala Ile Ser Asp Leu Glu Val Glu Asn Arg Glu
            180                 185                 190

Ser Lys Gly Ser Met Trp His Ile Arg Tyr Pro Leu Ala Asp Gly Ala
    195                 200                 205

Lys Thr Ala Asp Gly Lys Asp Tyr Leu Val Val Ala Thr Thr Arg Pro
210                 215                 220

Glu Thr Leu Leu Gly Asp Thr Gly Val Ala Val Asn Pro Glu Asp Pro
225                 230                 235                 240

Arg Tyr Lys Asp Leu Ile Gly Lys Tyr Val Ile Leu Pro Leu Val Asn
                245                 250                 255

Arg Arg Ile Pro Ile Val Gly Asp Glu His Ala Asp Met Glu Lys Gly
            260                 265                 270

Thr Gly Cys Val Lys Ile Thr Pro Ala His Asp Phe Asn Asp Tyr Glu
    275                 280                 285

Val Gly Lys Arg His Ala Leu Pro Met Ile Asn Ile Leu Thr Phe Asp
    290                 295                 300

Gly Asp Ile Arg Glu Ser Ala Gln Val Phe Asp Thr Lys Gly Asn Glu
305                 310                 315                 320

Ser Asp Val Tyr Ser Ser Glu Ile Pro Ala Glu Phe Gln Lys Leu Glu
                325                 330                 335

Arg Phe Ala Ala Arg Lys Ala Val Val Ala Ile Asp Ala Leu Gly
            340                 345                 350

Leu Leu Glu Glu Ile Lys Pro His Asp Leu Thr Val Pro Tyr Gly Asp
    355                 360                 365

Arg Gly Gly Val Val Ile Glu Pro Met Leu Thr Asp Gln Trp Tyr Val
    370                 375                 380

Arg Ala Asp Val Leu Ala Lys Pro Ala Val Glu Ala Val Glu Asn Gly
385                 390                 395                 400

Asp Ile Gln Phe Val Pro Lys Gln Tyr Glu Asn Met Tyr Phe Ser Trp
                405                 410                 415

Met Arg Asp Ile Gln Asp Trp Cys Ile Ser Arg Gln Leu Trp Trp Gly
```

His Arg Ile Pro Ala Trp Tyr Asp Glu Ala Gly Asn Val Tyr Val Gly
            420                 425                 430

Arg Asn Glu Glu Glu Val Arg Lys Glu Asn Asn Leu Gly Ala Asp Val
    435                 440                 445

Ala Leu Arg Gln Asp Glu Asp Val Leu Asp Thr Trp Phe Ser Ser Ala
465                 470                 475                 480

Leu Trp Thr Phe Ser Thr Leu Gly Trp Pro Glu Asn Thr Asp Ala Leu
                485                 490                 495

Arg Gln Phe His Pro Thr Ser Val Met Val Ser Gly Phe Asp Ile Ile
            500                 505                 510

Phe Phe Trp Ile Ala Arg Met Ile Met Met Thr Met His Phe Ile Lys
    515                 520                 525

Asp Glu Asn Gly Lys Pro Gln Val Pro Phe His Thr Val Tyr Met Thr
530                 535                 540

Gly Leu Ile Arg Asp Asp Glu Gly Gln Lys Met Ser Lys Ser Lys Gly
545                 550                 555                 560

Asn Val Ile Asp Pro Leu Asp Met Val Asp Gly Ile Ser Leu Pro Glu
                565                 570                 575

Leu Leu Glu Lys Arg Thr Gly Asn Met Met Gln Pro Gln Leu Ala Asp
            580                 585                 590

Lys Ile Arg Lys Arg Thr Glu Lys Gln Phe Pro Asn Gly Ile Glu Pro
    595                 600                 605

His Gly Thr Asp Ala Leu Arg Phe Thr Leu Ala Ala Leu Ala Ser Thr
610                 615                 620

Gly Arg Asp Ile Asn Trp Asp Met Lys Arg Leu Glu Gly Tyr Arg Asn
625                 630                 635                 640

Phe Cys Asn Lys Leu Trp Asn Ala Ser Arg Phe Val Leu Met Asn Thr
                645                 650                 655

Glu Gly Gln Asp Cys Gly Phe Asn Gly Gly Glu Met Thr Leu Ser Leu
            660                 665                 670

Ala Asp Arg Trp Ile Leu Ala Glu Phe Asn Gln Thr Ile Lys Ala Tyr
    675                 680                 685

Arg Glu Ala Leu Asp Ser Phe Arg Phe Asp Ile Ala Ala Gly Ile Leu
690                 695                 700

Tyr Glu Phe Thr Trp Asn Gln Phe Cys Asp Trp Tyr Leu Glu Leu Thr
705                 710                 715                 720

Lys Pro Val Met Asn Gly Gly Thr Glu Ala Glu Leu Arg Gly Thr Arg
                725                 730                 735

His Thr Leu Val Thr Val Leu Glu Gly Leu Leu Arg Leu Ala His Pro
            740                 745                 750

Ile Ile Pro Phe Ile Thr Glu Thr Ile Trp Gln
    755                 760

<210> SEQ ID NO 27
<211> LENGTH: 287
<212> TYPE: PRT
<213> ORGANISM: Methanococcus jannaschii

<400> SEQUENCE: 27

Met Asp Glu Phe Glu Met Ile Lys Arg Asn Thr Ser Glu Ile Ile Ser
1               5                   10                  15

Glu Leu Arg Glu Val Leu Lys Lys Asp Glu Lys Ser Ala Leu Ile Gly
            20                  25                  30

Phe Glu Pro Ser Gly Lys Ile His Leu Gly His Tyr Leu Gln Lys Lys
            35                  40                  45

Met Ile Asp Leu Gln Asn Ala Gly Phe Asp Ile Ile Pro Leu Ala
 50                  55                  60

Asp Leu His Ala Tyr Leu Asn Gln Lys Gly Glu Leu Asp Glu Ile Arg
 65                  70                  75                  80

Lys Ile Gly Asp Tyr Asn Lys Lys Val Phe Glu Ala Met Leu Lys Ala
                 85                  90                  95

Lys Tyr Val Tyr Gly Ser Glu Phe Gln Leu Asp Lys Tyr Thr Leu Asn
                100                 105                 110

Val Tyr Arg Leu Ala Leu Lys Thr Thr Leu Lys Ala Arg Arg Ser Met
            115                 120                 125

Glu Leu Ile Ala Arg Glu Asp Glu Asn Pro Val Ala Glu Val Ile Tyr
130                 135                 140

Pro Ile Met Gln Val Asn Gly Cys His Tyr Lys Gly Val Asp Val Ala
145                 150                 155                 160

Val Gly Gly Met Glu Gln Arg Lys Ile Met Leu Ala Arg Glu Leu Leu
                165                 170                 175

Pro Lys Lys Val Val Cys Ile His Pro Val Leu Thr Gly Leu Asp Gly
            180                 185                 190

Glu Gly Lys Met Ser Ser Ser Gly Asn Phe Ile Ala Val Asp Asp Ser
            195                 200                 205

Pro Glu Glu Ile Arg Ala Phe Lys Lys Ala Tyr Cys Pro Ala Gly Val
210                 215                 220

Val Glu Gly Asn Pro Glu Ile Ala Lys Tyr Phe Leu Glu Tyr Pro Leu
225                 230                 235                 240

Thr Ile Lys Pro Glu Lys Phe Gly Gly Asp Leu Thr Val Asn Ser Tyr
                245                 250                 255

Glu Glu Ser Leu Phe Lys Asn Lys Glu Leu His Pro Met Asp Leu Lys
            260                 265                 270

Ala Val Ala Glu Glu Leu Ile Lys Ile Leu Glu Pro Ile Arg Lys
            275                 280                 285

<210> SEQ ID NO 28
<211> LENGTH: 539
<212> TYPE: PRT
<213> ORGANISM: Methanococcus jannaschii

<400> SEQUENCE: 28

Met Arg Phe Asp Pro Glu Lys Ile Lys Lys Asp Ala Lys Glu Asn Phe
 1               5                  10                  15

Asp Leu Thr Trp Asn Glu Gly Lys Lys Met Val Lys Thr Pro Thr Leu
            20                  25                  30

Asn Glu Arg Tyr Pro Arg Thr Thr Phe Arg Tyr Gly Lys Ala His Pro
            35                  40                  45

Val Tyr Asp Thr Ile Gln Lys Leu Arg Glu Ala Tyr Leu Arg Met Gly
 50                  55                  60

Phe Glu Glu Met Met Asn Pro Leu Ile Val Asp Glu Lys Glu Val His
 65                  70                  75                  80

Lys Gln Phe Gly Ser Glu Ala Leu Ala Val Leu Asp Arg Cys Phe Tyr
                 85                  90                  95

Leu Ala Gly Leu Pro Arg Pro Asn Val Gly Ile Ser Asp Glu Arg Ile
                100                 105                 110

Ala Gln Ile Asn Gly Ile Leu Gly Asp Ile Gly Asp Glu Gly Ile Asp
            115                 120                 125

```
Lys Val Arg Lys Val Leu His Ala Tyr Lys Lys Gly Lys Val Glu Gly
130                 135                 140

Asp Asp Leu Val Pro Glu Ile Ser Ala Ala Leu Glu Val Ser Asp Ala
145                 150                 155                 160

Leu Val Ala Asp Met Ile Glu Lys Val Phe Pro Glu Phe Lys Glu Leu
                165                 170                 175

Val Ala Gln Ala Ser Thr Lys Thr Leu Arg Ser His Met Thr Ser Gly
            180                 185                 190

Trp Phe Ile Ser Leu Gly Ala Leu Leu Glu Arg Lys Glu Pro Pro Phe
        195                 200                 205

His Phe Phe Ser Ile Asp Arg Cys Phe Arg Arg Glu Gln Gln Glu Asp
210                 215                 220

Ala Ser Arg Leu Met Thr Tyr Tyr Ser Ala Ser Cys Val Ile Met Asp
225                 230                 235                 240

Glu Asn Val Thr Val Asp His Gly Lys Ala Val Ala Glu Gly Leu Leu
                245                 250                 255

Ser Gln Phe Gly Phe Glu Lys Phe Leu Phe Arg Pro Asp Glu Lys Arg
            260                 265                 270

Ser Lys Tyr Tyr Val Pro Asp Thr Gln Thr Glu Val Phe Ala Phe His
        275                 280                 285

Pro Lys Leu Val Gly Ser Asn Ser Lys Tyr Ser Asp Gly Trp Ile Glu
290                 295                 300

Ile Ala Thr Phe Gly Ile Tyr Ser Pro Thr Ala Leu Ala Glu Tyr Asp
305                 310                 315                 320

Ile Pro Cys Pro Val Met Asn Leu Gly Leu Gly Val Glu Arg Leu Ala
                325                 330                 335

Met Ile Leu His Asp Ala Pro Asp Ile Arg Ser Leu Thr Tyr Pro Gln
            340                 345                 350

Ile Pro Gln Tyr Ser Glu Trp Glu Met Ser Asp Ser Glu Leu Ala Lys
        355                 360                 365

Gln Val Phe Val Asp Lys Thr Pro Glu Thr Pro Glu Gly Arg Glu Ile
370                 375                 380

Ala Asp Ala Val Val Ala Gln Cys Glu Leu His Gly Glu Glu Pro Ser
385                 390                 395                 400

Pro Cys Glu Phe Pro Ala Trp Glu Gly Glu Val Cys Gly Arg Lys Val
                405                 410                 415

Lys Val Ser Val Ile Glu Pro Glu Glu Asn Thr Lys Leu Cys Gly Pro
            420                 425                 430

Ala Ala Phe Asn Glu Val Val Thr Tyr Gln Gly Asp Ile Leu Gly Ile
        435                 440                 445

Pro Asn Thr Lys Lys Trp Gln Lys Ala Phe Glu Asn His Ser Ala Met
450                 455                 460

Ala Gly Ile Arg Phe Ile Glu Ala Phe Ala Ala Gln Ala Ala Arg Glu
465                 470                 475                 480

Ile Glu Glu Ala Ala Met Ser Gly Ala Asp Glu His Ile Val Arg Val
                485                 490                 495

Arg Ile Val Lys Val Pro Ser Glu Val Asn Ile Lys Ile Gly Ala Thr
            500                 505                 510

Ala Gln Arg Tyr Ile Thr Gly Lys Asn Lys Lys Ile Asp Met Arg Gly
        515                 520                 525

Pro Ile Phe Thr Ser Ala Lys Ala Glu Phe Glu
530                 535
```

```
<210> SEQ ID NO 29
<211> LENGTH: 215
<212> TYPE: PRT
<213> ORGANISM: Trypanosoma cruzi

<400> SEQUENCE: 29

Ala Pro Ala Ala Val Asp Trp Arg Ala Arg Gly Ala Val Thr Ala Val
1               5                   10                  15

Lys Asp Ser Gly Gln Cys Gly Ser Gly Trp Ala Phe Ala Ala Ile Gly
            20                  25                  30

Asn Val Glu Cys Gln Trp Phe Leu Ala Gly His Pro Leu Thr Asn Leu
        35                  40                  45

Ser Glu Gln Met Leu Val Ser Cys Asp Lys Thr Asp Ser Gly Cys Ser
    50                  55                  60

Ser Gly Leu Met Asp Asn Ala Phe Glu Trp Ile Val Gln Glu Asn Asn
65                  70                  75                  80

Gly Ala Val Tyr Thr Glu Asp Ser Tyr Pro Tyr Ala Ser Ala Thr Gly
                85                  90                  95

Ile Ser Pro Pro Cys Thr Thr Ser Gly His Thr Val Gly Ala Thr Ile
            100                 105                 110

Thr Gly His Val Glu Leu Pro Gln Asp Glu Ala Gln Ile Ala Ala Trp
        115                 120                 125

Leu Ala Val Asn Gly Pro Val Ala Val Cys Val Asp Ala Ser Ser Trp
    130                 135                 140

Met Thr Tyr Thr Gly Gly Val Met Thr Ser Cys Val Ser Glu Ser Tyr
145                 150                 155                 160

Asp His Gly Val Leu Leu Val Gly Tyr Asn Asp Ser His Lys Val Pro
                165                 170                 175

Tyr Trp Ile Ile Lys Asn Ser Trp Thr Thr Gln Trp Gly Glu Glu Gly
            180                 185                 190

Tyr Ile Arg Ile Ala Lys Gly Ser Asn Gln Cys Leu Val Lys Glu Glu
        195                 200                 205

Ala Ser Ser Ala Val Val Gly
    210                 215

<210> SEQ ID NO 30
<211> LENGTH: 215
<212> TYPE: PRT
<213> ORGANISM: Trypanosoma cruzi

<400> SEQUENCE: 30

Ala Pro Ala Ala Val Asp Trp Arg Ala Arg Gly Ala Val Thr Ala Val
1               5                   10                  15

Lys Asp Gln Gly Gln Cys Gly Ser Cys Trp Ala Phe Ser Ala Ile Gly
            20                  25                  30

Asn Val Glu Cys Gln Trp Phe Leu Ala Gly His Pro Leu Thr Asn Leu
        35                  40                  45

Ser Glu Gln Met Leu Val Ser Cys Asp Lys Thr Asp Ser Gly Cys Ser
    50                  55                  60

Gly Gly Leu Met Asn Asn Ala Phe Glu Trp Ile Val Gln Glu Asn Asn
65                  70                  75                  80

Gly Ala Val Tyr Thr Glu Asp Ser Tyr Pro Tyr Ala Ser Gly Glu Gly
                85                  90                  95

Ile Ser Pro Pro Cys Thr Thr Ser Gly His Thr Val Gly Ala Thr Ile
            100                 105                 110
```

-continued

```
Thr Gly His Val Glu Leu Pro Gln Asp Glu Ala Gln Ile Ala Ala Trp
        115                 120                 125

Leu Ala Val Asn Gly Pro Val Ala Val Ala Val Asp Ala Ser Ser Trp
        130                 135                 140

Met Thr Tyr Thr Gly Gly Val Met Thr Ser Cys Val Ser Glu Gln Leu
145                 150                 155                 160

Asp His Gly Val Leu Leu Val Gly Tyr Asn Asp Ser Ala Ala Val Pro
                165                 170                 175

Tyr Trp Ile Ile Lys Asn Ser Trp Thr Thr Gln Trp Gly Glu Glu Gly
            180                 185                 190

Tyr Ile Arg Ile Ala Lys Gly Ser Asn Gln Cys Leu Val Lys Glu Glu
        195                 200                 205

Ala Ser Ser Ala Val Val Gly
        210                 215
```